US006858210B1

(12) United States Patent
Marquis et al.

(10) Patent No.: US 6,858,210 B1
(45) Date of Patent: Feb. 22, 2005

(54) THERAPEUTIC AND DIAGNOSTIC DOMAIN 1 β₂GPI POLYPEPTIDES AND METHODS OF USING SAME

(75) Inventors: David M. Marquis, Encinitas, CA (US); Gilbert M. Iverson, Del Mar, CA (US); Edward J. Victoria, San Diego, CA (US); David S. Jones, San Diego, CA (US); Matthew D. Linnik, San Diego, CA (US)

(73) Assignee: La Jolla Pharmaceutical Co., San Diego, CA (US)

( * ) Notice: Subject to any disclaimer, the term of this patent is extended or adjusted under 35 U.S.C. 154(b) by 0 days.

(21) Appl. No.: 09/328,199

(22) Filed: Jun. 8, 1999

Related U.S. Application Data

(60) Provisional application No. 60/103,088, filed on Oct. 5, 1998, and provisional application No. 60/088,656, filed on Jun. 9, 1998.

(51) Int. Cl.⁷ ..................... A61K 39/00; C07N 14/435; G01N 33/564

(52) U.S. Cl. .............................. 424/185.1; 424/192.1; 424/193.1; 424/194.1; 435/975; 436/506; 436/69; 514/12; 514/13; 514/14; 514/15; 514/16; 514/17; 530/324; 530/315; 530/326; 530/327; 530/328; 530/329; 530/413

(58) Field of Search ..................... 530/324, 325–329, 530/413; 514/12; 424/185.1, 192.1, 193.1, 194.1; 435/975; 436/506, 69

(56) References Cited

U.S. PATENT DOCUMENTS

| | | | |
|---|---|---|---|
| 4,191,668 A | | 3/1980 | Katz |
| 4,650,675 A | | 3/1987 | Borel et al. |
| 4,751,181 A | | 6/1988 | Keene |
| 5,126,131 A | | 6/1992 | Dintzis et al. |
| 5,162,515 A | | 11/1992 | Conrad et al. |
| 5,268,454 A | | 12/1993 | Barstad et al. |
| 5,276,013 A | | 1/1994 | Conrad et al. |
| 5,344,758 A | | 9/1994 | Krilis et al. |
| 5,370,871 A | | 12/1994 | Dintzis et al. |
| 5,472,883 A | | 12/1995 | Matsuura et al. |
| 5,498,538 A | | 3/1996 | Kay et al. |
| 5,506,110 A | | 4/1996 | Matsuura et al. |
| 5,552,391 A | | 9/1996 | Coutts et al. |
| 5,606,047 A | | 2/1997 | Coutts et al. |
| 5,633,395 A | * | 5/1997 | Coutts et al. |
| 5,780,319 A | | 7/1998 | Maxfield Wilson et al. 436/518 |
| 5,859,213 A | | 1/1999 | Stefas et al. ............ 530/415 |
| 5,874,409 A | | 2/1999 | Victoria et al. |
| 5,998,223 A | * | 12/1999 | Matsuura et al. |
| 6,022,544 A | | 2/2000 | Dintzis et al. |
| 6,060,056 A | | 5/2000 | Coutts et al. |
| 6,207,160 B1 | | 3/2001 | Victoria et al. |
| 2001/0051351 A1 | | 12/2001 | Racis |
| 2002/0025321 A1 | | 2/2002 | Shoenfeld et al. |
| 2002/0110535 A1 | | 8/2002 | Jones |

FOREIGN PATENT DOCUMENTS

| | | |
|---|---|---|
| EP | 0 438 259 A1 | 7/1991 |
| EP | 0 442 724 A3 | 8/1991 |
| EP | 0 442 724 A2 | 8/1991 |
| EP | 0 498 658 A3 | 8/1992 |
| EP | 0 498 658 B1 | 8/1992 |
| EP | 0 498 658 A2 | 8/1992 |
| EP | 0 642 798 A2 | 3/1995 |
| EP | 0 730 155 A1 | 9/1996 |
| EP | 0 821 003 A1 | 1/1998 |
| WO | WO 86/04093 A1 | 7/1986 |
| WO | WO 87/00056 A1 | 1/1987 |
| WO | WO 88/09810 A1 | 12/1988 |
| WO | WO 89/09628 A1 | 10/1989 |
| WO | WO 91/10426 A1 | 7/1991 |
| WO | WO 91/15772 | 10/1991 |
| WO | WO 92/11029 A1 | 7/1992 |
| WO | WO 92/13558 A1 | 8/1992 |
| WO | WO 93/02093 A1 | 2/1993 |
| WO | WO 95/07073 A1 | 3/1995 |
| WO | WO 95/14231 A1 | 5/1995 |
| WO | WO 95/14231 | 5/1995 |
| WO | WO 96/04006 A1 | 2/1996 |
| WO | WO 96/04006 | 2/1996 |
| WO | WO 96/40197 A1 | 12/1996 |
| WO | WO 97/46251 A1 | 12/1997 |
| WO | WO 98/12133 A3 | 5/1998 |
| WO | WO 98/21233 A2 | 5/1998 |
| WO | WO 99/47925 | 9/1999 |
| WO | WO 99/64595 A1 | 12/1999 |
| WO | WO 00/01729 A3 | 1/2000 |
| WO | WO 00/01729 A2 | 1/2000 |
| WO | WO 00/20019 | 4/2000 |
| WO | WO 00/34231 A1 | 6/2000 |
| WO | WO 00/75105 | 12/2000 |
| WO | WO 01/18541 | 3/2001 |
| WO | WO 01/41813 | 6/2001 |
| WO | WO 01/79449 | 10/2001 |
| WO | WO 01/88088 | 11/2001 |
| WO | WO 02/27315 | 4/2002 |
| WO | WO 00/66715 A1 | 11/2002 |

OTHER PUBLICATIONS

Palkeyeua et al (USPTO Translation).*
Cruse et al pp. 102–103 Illustrated Dictionary of Immunology, 1995 CRC Press.*

(List continued on next page.)

*Primary Examiner*—David Saunders
(74) *Attorney, Agent, or Firm*—Morrison & Foerster LLP

(57) ABSTRACT

The present invention provides domain 1 β₂GPI polypeptides, polynucleotides encoding these polypeptides, mimetics of these polypeptides, and methods using domain 1 β₂GPI polypeptides and mimetics. Domain 1 of β₂GPI has been shown to bind to anti-cardiolipin (β₂GPI-dependent antiphospholipid) antibodies, which are associated with several pathologies, such as thrombosis and fetal loss. The domain 1 β₂GPI polypeptides may be used to detect β₂GPI-dependent antiphospholipid antibodies in a sample. The invention further provides methods of inducing tolerance using these domain 1 β₂GPI polypeptides.

104 Claims, 16 Drawing Sheets

OTHER PUBLICATIONS

Abaza et al. J. of Protein Chemistry, 11(5):433–444, 1992.*
Matsuura et al, J. of Immunology, 148:3885–91, 1992.*
Sequence Search—US–09–328–199–6–open.1 spt—US–09–328–199–8–open.1spt by PTO on GenCoreVersion 4.5 Compugen '93, Dec, 20, 2000.*
Arvieux et al. (1991). "Measurement of anti–phospholipid antibodies by ELISA using $\beta_2$–glycoprotein I as an antigen" *J. Immunol. Methods* 143:223–229.
Ausubel et al., eds. (1987). Current Protocols in Molecular Biology. Table of contents enclosed herewith.
Bakimer et al. (1992). "Induction of Primary Antiphospholipid Syndrome in Mice by Immunization with a Human Monoclonal Anticardiolipin Antibody (H–3)" *J. Clin. Invest.* 89:1558–1563.
Balaram. (1992). "The design and construction of synthetic protein mimics" *Pure & Appl. Chem.* 64:1061–1066.
Barbas et al. (1991). "Assembly of combinatorial antibody libraries on phage surfaces: The gene III site" *Proc. Natl. Acad. Sci. USA* 88:7978–7982.
Barlow et al. (1991). "Secondary Structure of a Complement Control Protein Module by Two–Dimensional $^1$ H NMR" *Biochem.* 30:997–1004.
Blank et al. (1991). "Induction of anti–phospholipid syndrome in naive mice wtih mouse lupus monoclonal and human polyclonal anti–cardiolipin antibodies" *Proc. Natl. Acad. Sci.* 88:3069–3073.
Borel et al. (1990). "A novel technique to link either proteins or peptides to gammaglobulin to construct tolerogens" *Immunol. Methods* 126:159–168.
Borel et al. (1995). "Food Allergens Transformed into Tolerogens" *Int. Arch. Allergy Immunol.* 107:264–267.
Borel et al. (1996). "Parenteral and Oral Administration of tolerogens: Protein–IgG Conjugates" *Ann. N.Y. Acad. Sci.* 778:80–87.
Burgess et al. (1995)."Comparison of the Effects of (2S, 3S)–2,3–Methanomethionine, (2R,3R)–2,3–Methanomethionine, and (2R,3R)–2,3–Methanophenylalainie on the Confrontations of Small Peptides" *J. Am. Chem. Soc.* 117:3808–3819.
Coligan et al., eds. (1991) *Current Protocols in Immunology*, Table of contents enclosed herewith.
Dumas et al. (1995). "Induction of tolerance by administration of hapten–immunoglobulin conjugates is associated with decreased IL–2 and IL–4 production" *Arch. Dematol. Res.* 287:123–128.
Freshney, ed. (1987). *Animal Cell Culture a practical approach.* Table of contents enclosed herewith.
Gacesa et al. (1994). *Vectors, Essential Data.* John Wiley & Sons.
Gait, ed. (1984). *Oligonucleotide Synthesis, a practical approach.* Table of contents enclosed herewith.
Galli et al. (1990). "Anticardiolipin antibodies (ACAA) directed not to cardiolipin but to a plasma protein cofactor" *Lancet* 335:1544–1547.
George et al. (1998). "Target recognition of $\beta_2$–Glycoprotein I ($\beta_2$GPI)–Dependent Anticardiolipin Antibodies: Evidence for Involvement of the Fourth Domain of $\beta_2$GPI in Antibody Binding" *J. Immunol.* 160:3917–3923.
Gharavi et al. (1987). "Anticardiolipin antibodies: isotype distribution and phospholipid specificity" *Ann. Rheum. Dis.* 46m:1–6.

Harris et al. (1983). "Anticardiolipin antibodies: detection by radioimmunoassay and association with thrombosis in systemic lupus erythematosus" *Lancet* 2:1211–1214.
Harris et al. eds. (1991). *Phospholipid–Binding Antibodies.* CRC Press: Boca Raton, FL. Table of Contents Only.
Hinds et al. (1991). "Synthesis Conformational Properties, and Antibody Recognition of Peptides Containing $\beta$–Turn Mimitecs based on $\alpha$–Alkylproline Derivatives" *Med. Chem.* 34:1777–1789.
Hruby et al. (1990). "Emerging approaches in the molecular design of receptor–selective peptide ligands: conformational, topographical and dynamic considerations" *Biochem. J.* 268:249–262.
Hruby et al. (1994). "Design of Novel Synthetic Peptides Including Cyclic Conformationally and Topographically Constrained Analogs" *Methods in Mol. Biol.* 35:201–240.
Hunt et al. (1993). "Identification of a region of $\beta_2$–glycoprotein I critical for Lipid binding and anti–cardiolipin antibody cofactor activity" *Proc. Natl. Acad. Sci. USA* 90:2141–2145.
Hunt et al. (1994). "The Fifth Domain of $\beta_2$–Glycoprotein I Contains a Phospholipid Binding Site (Cys281–Cys288) and a Region Recognized by Anticardiolipin Antibodies" *J. Immunol.* 152(2):653–659.
Ichinose et al. (1990) "Structure of transglutaminases" *J. Biol. Chem.* 265(23):13411–13414.
Igarashi et al. (1996). "Human $\beta_2$–Glycoprotein I as an Anticardiolipin Cofactor Determined Using Deleted Mutants Expressed by a Baculovirus System" *Blood* 87:3262–3270.
Iverson et al. (1998). "Anti–$\beta$2 glycoprotein I ($\beta$2GPI) autoantibodies recognize and epitope on the first domain of $\beta$2GPI" *Proc. Natl. Acad. Sci USA* 95:15542–15546.
Jakoby and Pastan eds. (1979). *Methods in Enzymology* Academic Press, Inc. Table of contents enclosed herewith. only.
Kunkel et al. (1987). "Rapid and Efficient Site–specific Mutagenesis without Phenotypic Selection" *Methods in Enzymology* 154:367–382.
Leung et al. (1989). "A method for random mutagenesis of a defined DNA segment using a modified polymerase chain reaction" *Technique* 1:11–15.
Lockshin et al. (1985). "Antibody to cardiolipin as a predictor of fetal distress or death in pregnant patients with systemic lupus erythematosus" *N. Engl. J. Med.* 313:152–156.
Lozier et al. (1984). "Complete amino acid sequence of human plasma $\beta_2$–glycoprotein I" *Proc. Natl. Acad. Sci.USA* 81:3640–3644.
Mahato et al. (1997). "Cationic Lipid–Based Gene Delivery Systems: Pharmaceutical Perspectives" *Pharm. Res.* 14(7):853–859.
Matsuura et al. (1994). "Anticardiolipin Antibodies Recognize $\beta_2$–Glycoprotein I Structure altered by Interfacing with an Oxygen Modified Solid Phase Surface" *J. Exp. Med.* 179:457–461.
McNeil et al. (1990). "Anti–phospholipid antibodies are directed against a complex antigen that includes a lipid–binding inhibitor of coagulation: $\beta_2$–Glycoprotein I (apolipoprotein H)" *Proc. Natl. Acad. Sci. USA* 87:4120–4124.
McNeil et al. (1991). "Immunology and Clinical Importance of Antiphospholipid Antibodies" in Advances in Immunology. vol. 49, Austen et al. eds., Academic Press, San Diego, CA, pp. 193–281.

Merrifield, R.B. (1963). "Solid Phase Peptide Synthesis. I. The Synthesis of a Tetrapeptide" *J. Am. Chem. Soc.* 85(14):2149–2154.

Miller and Calos, eds. (1987). "Gene Transfer Vectors for Mammalian Cells" in *Current Communications in Molecular Biology*. Table of contents enclosed herewith.

Mullis et al. eds. (1994). *PCR: The Polymerase Chain Reaction*. Table of contents enclosed herewith.

Norman et al. (1991). "Three–dimensional Structure of a Complement Control Protein Module in Solution" *J. Mol. Biol.* 219:717–725.

Posnett et al. (1988). "A Novel Method for Producing Anti–peptide Antibodies" *J. Biol. Chem.* 263:1719–1725.

Reber et al. (1995). "Multicenter Evaluation of Nine Commercial Kits for the Quantitation of anticardiolipin Antibodies" *Thrombosis and Haemostat.* 73:444–452.

Redd et al. (1997). "A Complex Composed of Tup1 and Ssn6 Represses Transcription in Vitro"*J. Biol. Chem.* 272:11193–11197.

Reid et al. (1989). "Structure–function relationships of the complement components" *Immunol.Today* 10:177–180.

Remington (1995). *Practice of The Science and Pharmacy* 19th Ed. Mack Publishing. Table of contents only.

Rose, K. et al. (1991). "Preparation of Well–Defined Protein Conjugates Using Enzyme–Assisted Reverse Proteolysis" *Bioconjugate Chemistry* 2:154–159.

Rose, K. et al. (1996). "Natural peptides as building blocks for the synthesis of large protein–like molecules with hydrazone and oxime linkages" *Bioconjugate Chemistry* 7:552–556.

Roubey (1996). "Immunology of the antiphospholipid antibody syndrome" *Arthritis Rheum.*39:1444 –1454.

Roubey et al. (1995). "Anticardiolipin' Autoantibodies Recognize $\beta_2$–Glycoprotein I in the Absence of Phospholipid"*J. Immun.* 154(2): 954–960.

Sambrook et al. (1989). *Molecular Cloning: A Laboratory Manual*, 2nd edition. Table of contents enclosed herewith. only.

Steinkasserer et al. (1991). "Complete nucleotide and deduced amino acid sequence of human $\beta_2$–glycoprotein I" *Biochem. J.* 277:387–391.

Tam (1989). "High–Density Multiple Antigen–Peptide System for Preparation of Antipeptide Antibodies" *Meth. Enz.* 168:7–15.

Toniolo et al. (1993). "Structures of Peptides from α–Amino Acids Methylated at the α–Carbon" *Biopolymers* 33:1061–1072.

Toniolo, C. (1990). "Conformationally resticted peptides through short–range cyclization" *Int'l. J. Peptide Protein Res.* 35:287–300.

Vaarala et al. (1986). "Anticardiolipin Response in Acute Infections" *Clin. Immunol. Immunopathol.* 41:8–15.

Valesini et al. (1992). "A new player in the antiphorspholipid syndrome: the $\beta_2$–glycoprotein I cofactor" *Autoimmunity* 14:105–110.

Vermylen et al. (1992). "Is the antiphospholipid syndrome caused by antibodies directed against physiological relevant phospholipid–protein complexes?" *J. Lab. Clin. Med.* 120:10–12.

Weir and Blackwell, eds. (1996). *Weir's Handbook of Experimental Immunology*. Table of contents enclosed herewith.

Ada. G.L. (1987). "The generation of cellular vs. humoral immunity," Chapter 3 in *Synthetic Vaccines*. R. Arnon ed., CRC Press, Inc.: Boca Raton, Florida, vol. 1, pp. 25–37.

Aichele, P. et al. (1994). "Peptide–induced T–cell tolerance to prevent autoimmune diabetes in a transgeneic mouse model," *Proc. Natl. Acad. Sci. USA* 91:444–448.

Arvieux, J. et al. (1993). "Platelet activating properties of murine monoclonal antibodies to $\beta_2$–glycoprotein I," *Thromb. Haemostas.* 70(2):336–341.

Balass, M. et al., (1993). "Identification of a hexapeptide that mimics a conformation–dependent binding site of acetylcholine receptor by use of a phage–epitope library," *Proc. Natl. Acad. Sci. USA* 90:10638–10642.

Brighton, T.A. and Chesterman, C.N. (1994). "Antiphospholipid antibodies and thrombosis" *Balliere's Clin. Haematol.* 7(3):541–557.

Cesareni, G. (1992). "Peptide display on filamentous phage capsids: A new powerful tool to study protein–ligand interaction" *FEBS Lett.* 307(1):66–70.

Cruse, J.M. and Lewis, R.E. (1995). *Illustrated Dictionary of Immunology*. CRC Press, Boca Ration, FL, p. 156.

Cwirla, S.E. et al (1990). "Peptides on phage: A vast library of peptides for identifying ligands," *Proc. Natl. Acad. Sci. USA* 87:6378–6382.

Del Papa, N. et al. (1998). "Human β2–glycoprotein I binds to endothelial cells through a cluster of lysine residues that are critical for anionic phosholipid binding and offers epitopes for anti–β2–glycoprotein I antibodies," *J. Immunology* 160(11): 5572–5578.

Dower, W.J. et al. (1988). "High efficiency transformation of *E. coli* by high voltage electroporation," *Nucleic Acid Res.* 16(13):6127–6145.

Efimov, V.A et al. (1993). "Synthesis of Conjugates of Oligonucleotides with Polyethyleneglycol," Plenum Publishing Corporation, pp. 464–468. Translanted from *Bioorganicheskaya Khimiya* 19(8): 800–804.

Elliott, J.I. (1992). "Anergy and suppression in B–cell responses," *Scand. J. Immunol.* 36:761–767.

Francis, M.J. et al. (1988). "Peptides with added T–cell epitopes can overcome genetic restriction of the immune response" In *Vaccines 88*. H. Ginsberg et al. eds. Cold Spring Harbor Laboratory, pp. 1–7.

Gharavi et al. (1996). "Induction of antiphospholipid antibodies by immunization with a 15–amino acid peptide spanning the phospholipid binding site of $\beta_2$glycoprotein, I," *J. Invest. Med.* 44:69A.

Haas, S.J. and Smith, G.P. (1993). "Rapid sequencing of viral DNA from filamentous bacteriophage," *BioTechniques* 15:422–423, 426, 428–429.

Habicht, G.S. et al. (1973). "Methods for the study of the cellular basis of immunological tolerance," Chapter 6 In *Immune Response at the Cellular Level*. T.P. Zacharia ed., Marcel Dekker, Inc.: New York, pp. 141–160, especially 142.

Hagihara, Y. et al. (1995). "Role of the N– and C–terminal domains of bovine $\beta_2$–glycoprotein I in its interaction with cardiolipin," *J. Biochemistry* 118(1):129–136.

Harris, E.N. (1990). "Antiphospholipid antibodies," *Brit. J. Haemotol.* 74:1–9.

Hasselaar, P. et al. (1990). "Crossreactivity of antibodies directed against cardiolipin, DNA, endothelial cells and blood platelets," *Thromb. Haemostas.* 63(2):169–173.

Hertler, A.A. (1988). "Human immune response to immunotoxins" In *Immunotoxins*. A.E. Frankel ed., Kluwer Academic Publishers: Boston, pp. 475–480.

Holmes, D.S. and Quigley, M. (1981) "A rapid boiling method for the preparation of bacterial plasmids," *Anal. Biochem.* 144:193–197.

Igarashi, M. et al. (1996). "Human $\beta^2$–Glycoprotein I as a anticoadiolipin cofactor determined using deleted mutants expressed by a baculovirus systems," *Blood* 87(8): 3262–3270.

Jones, D.S. et al. (1994) "Conjugates of double–stranded oligonucleotides with poly(ethylene glycol) and keyhole Limpet hemocyanin: a model for treating systemic lupus erythematosus," *Bioconjugate Chem.* 5(5):390–399.

Jones, D.S. et al. (1995). "Immunospecific reduction of antioligonucleotide antibody–forming cells with a tetrakis–oligonucleotide conjugate (LJP 394), a therapeutic candidate for the treatment of lupus nephritis," *J. Medicinal Chemistry* 38(12):2138–2144.

Kandiah, D.A. et al. (1995). "Epitope mapping studies of antiphospholipid antibodies and $\beta_2$–GPI using synthetic peptides," *Lupus* 4(Suppl 1):S7–S11.

Kato, H. and Enjoji, K. (1991). "Amino acid sequence and location of the disulfide bonds in bovine $\beta_2$ glycoprotein I: The presence of five sushi domains," *Biochem.* 30:11687–11694.

Lauer, S.A. et al. (1993). "Amino acid sequence of the region of $\beta_2$–glycoprotein 1 (gp1) which mediates binding of autoantibodies to the cardiolipin–gpl complex in humans," *Immunol.* 80:22–28.

Lenstra, J.A. et al. (1992). "Isolation of sequences from a random–sequence expression library that mimic viral epitopes," *J. Immunological Methods* 152:149–157.

Luzzago, A. et al. (1993). "Mimicking of discontinuous eptiopes by phage–displayed peptides, I. Epitope mapping of human H ferritin using a phage library of constrained peptides," *Gene* 128:51–57.

McCarty–Farid, G.A. (1993). "Antiphospholipid antibodies in systemic lupus erythematosus and Sjörgen's syndrome," *Current Opinion in Rheumatology* 5:596–603.

McConathy, W.J. and Alaupovic, P. (1986). "Isolation and characterization of other apolipoproteins," *Meth. Enzymol.* 128:297–310.

Moos, W.H. et al. (1993). "Recent advances in the generation of molecular diversity," *Ann. Reports Med. Chem.* 28:315–324.

Nonaka, M. et al. (1992). "Molecular cloning of mouse $\beta_2$–glycoprotein I and mapping of the gene to chromosome 11," *Genomics* 13:1082–1087.

Nossal, G.J. (1989). "Immunologic Tolerance" Chapter 19 In *Fundamental Immunology*. W.E. Paul ed., Raven Press, Ltd.: New York, pp. 571–586, especially 577–579.

Papalian, M. et al. (1980). "Reaction of systemic lupus erythematosus antinative DNA antibodies with native DNA fragments from 20 to 1,200 base pairs," *J. Clin. Invest.* 65:469–477.

Paul, W.E. ed. (1993). *Fundamental Immunology*, New York: Raven Press. 3rd Ed. The title page and table of contents are enclosed herewith. Title & Table of Contents considered only.

Petri, M. (1994). "Diagnosis of antiphospholipid antibodies," *Rheumatic Disease Clinics of North America* 20(2):443–469.

Powell, M. (1993). "Peptide stability in drug development: In vitro peptide degradation in plasma and serum," *Ann Reports Med. Chem.* 28:285–294.

Sanger, F. et al. (1977). "DNA sequencing with chain–terminating inhibitors," *Proc. Natl. Acad. Sci. USA* 74(12):5463–5467.

Scott, J.K. and Smith, G.P. (1990). "Searching for peptide ligands with an epitope library," *Science* 249:386–390.

Scott, J.K. (1994). "Identifying lead peptides from epitope libraries," Chapter 1 In *Biological Approaches to Rational Drug Design*. D.B. Weiner and W.V Williams eds., CRC Press:Boca, Raton, FL., pp. 1–27. The title page and table of contents are enclosed herewith.

Sehon, A.H. (1991). "Suppression of antibody responses by conjugates of antigens and monomethoxpoly(ethylene glycol)," *Advanced Drug Delivery Reviews* 6(2):203–217.

Sheng, Y. et al. (1996). "Site–directed mutagenesis of recombinant human $\beta_2$–glycoprotein I identifies a cluster of lysine residues that are critical for phospholipid binding and anticardiolipin antibody activity," *J. Immunol* 157(8):3744–3751.

Smith, G.P. and Scott, J.K. (1993). "Libraries of peptides and proteins displayed on filamentous phage," *Meth. Enzymol* 217:228–257.

Steinkasserer, A. et al. (1992). "Activity, disulphide mapping and structural modelling of the fifth domain of human $\beta_2$–glycoprotein I," *FEBS Lett.* 313(2):193–197.

Vuilleumier, S. and Mutter, M. (1992). "Antigen mimicry with synthetic peptides," Chapter 3 In *Structure of Antigens*. M.H.V. Regenmortel ed., CRC Press:Boca Raton, Fl. vol. 1, pp. 43–54.

Wagenknecht, D.R. and McIntyre, J.A. (1993). "Changes in $\beta_2$–glycoprotein I antigenicity induced by phospholipid binding," *Thromb. Haemostas* 69(4):361–365.

Wang, M. et al. (1995). "Epitope specificity of monoclonal anti–$\beta_2$–glycoprotein I antibodies derived from patients with the antiphospholipid syndrome," *J. Immunol.* 155(3):1629–1636.

Jones, J.V. et al. (Sep. 9–12, 1992). "Antigenic Specificity of Anticardiolipin Antibodies Appears to Depend on Conformation of $\beta_2$–Glycoprotein I," *Proc. 5th International. Symposium Antiphospholipid Antibodies*, Sponsored by University of Texas Health Science Center at San Antonio, Hyatt Regency San Antonio, Texas (Abstract S5) (4 pages total).

U.S. patent application Ser. No. 09/457,607 filed Dec. 8, 1999. "Valency Platform Molecules Comprising Carbamate Linkages."

U.S. Application No. pending filed Nov. 28, 2000. "Methods of Treating Lupus Based on Antibody Affinity and Screening Methods and Compositions for Use Thereof."

Blank, M. et al. (1999). "Prevention of Experimental Antiphospholipid Syndrome and Endothelial Cell Activation by Synthetic Peptides," *Proc. Natl. Acad. Sci. USA Immunology* 96: 5164–5168.

Jones, D. S. et al. (1999) "Multivalent Thioether–Peptide Conjugates: B Cell Tolerance of an Anti–Peptide Immune Response," *Bioconjugate Chemistry* 10: 480–488.

Pal 'Keeva, E.A. (1996). "Synthesis and Antigenic Properties of Peptide Fragments of $\beta_2$–Glycoprotein–I," *Bioorg. Khim.* 22(9): 678–685. (English language abstract at end of article).

George, J. et al. (1998). "Target Recognition of Beta2–Glycoprotein I ($\beta_2$GPI)–Dependent Anticardiolipin Antibodies: Evidence for Involvement of the Fourth Domain of $\beta_2$GPI in Antibody Binding," *Journal of Immunology* 160(8):3917–3923.

GenBank No. X57847, (Feb. 17, 1997). "*H. sapiens* ApoH mRNA for Apolipoprotein H (beta–2–glycoprotein I)," located at <http://www.ncbi.nlm.nih.gov/entrez/query.fcgi?cmd=Retrieve&db=nucleotide&list_uids=28813&dopt=GenBank&term=X57847&qty=1, on Nov. 21, 2003, 2 pages.

Bakimer, R. et al. (1992). "Induction of primary antiphospholipid syndrome in mice by immunization with a human monoclonal anticardiolipin antibody (H–3)" *J. Clin. Invest.* 89:1558–1563.

Blank, M. et al., (1991). "Induction of anti–phospholipid syndrome in naive mice with mouse lupus monoclonal and human polyclonal anti–cardiolipin antibodies" *Proc. Natl. Acad. Sci. USA* 88:3069–3073.

Branks, M. J. et al., (2000). "Tolerance Activity and Pharmacokinetics of Multivalent $\beta_2$GPI Domain One Conjugates in an Immunized Animal Model," *Abstract presented at 9th International Symposium on Antiphospholipid Antibodies*, Sep. 12–16, 2000, Tours, France, located at <http://ljpc.com/abstract _$2000_{13}$ tolerance.html> on Jan. 19, 2004, 1 page.

Cockerill, K.A. et al., (1999). "Development of an Antigen–Specific B–Cell Toleragen for the Treatment of Antiphospholipid Syndrome" *Abstract presented at 25th Annual Conference of La Jolla Immunologists, La Jolla, CA, Nov. 8–9, 1999*, located at <http://ljpc.com/abstract_1999_development_antigen.html> on Feb. 26, 2004, 1 page.

Cockerill, K.A. et al., (2003). "In Vivo Characterization of Bioconjugate B Cell Toleragens With Specificity for AutoAntibodies in Antiphospholipid Syndrome," *Abstract published in Int. Immunopharmacol 3(12):1667–1675, also located at <http://ljpc.com/abstract$_{13}$ 2003_html>on Jan. 19, 2004, 1 page.

Coutts, S.M. et al., (1995). "Synthetic Mimotopes of $\beta_2$–GPI–Specific Anti–Cardiolipin Antibodies" *Abstract presented at Australasian Society of Clinical Immunology and Allergy and Immunology Society Meeting, Sydney, Australia*, Oct. 30–Nov. 3, 1995, located at <http://ljpc.com/abstract_1995_synthetic mino.html> on Jan. 19, 2004, 1 page.

Coutts, S.M. et al., (1996). "Pharmacological Intervention in Antibody Mediated Disease," *Lupus* 5(2):158–159. *Conference held during the 6th Annual Meeting of The Australian Society of Clinical Immunology in Conjunction with the 6th Biennale Meeting of The Transpacific Allergy and Immunology Society*, in Sydney, Australia, on Oct. 1995.

Galli, M. et al., (1990). "Anticardiolipin antibodies (ACA) directed not to cardiolipin but to a plasma protein cofactor," *Lancet* 335:1544–1547.

Guerin, J. et al., (2002). "Heparin Inhibits the Binding of β2–Glycoprotein I to Phospholipids And Promotes the Plasmin–Mediated Inactivation of This Blood Protein: Elucidation of the Consequences of the Two Biological Events in Patients With The Anti–Phospholipid Syndrome," *J. Biol. Chem.* 277(4):2644–2649.

Horizon, A. et al., (2003). "Results of a Randomized, Placebo Controlled, Double Blind Phase 1/2 Clinical Trial (RCT) to Assess The Safety And Tolerability of LJP 1082 In Patients With Antiphospholipid Syndrome," *Abstract presented at the 67th Annual Meeting of the American College of Rheumatology*, Orlando, Florida, on Oct. 23–28, 2003, located at <http://ljpc.com/abstract/abstracts_2003_04.html> on Jan. 19, 2004, 2 pages.

Hunt, J. et al., (1994). "The fifth domain of β–glycoprotein I contains a phospholipid binding site (cys281–cys288) and a region recognized by anticardiolipin antibodies" *J. Immunol.* 152:653–659.

Iverson, M. G. et al. (1998). "A Chemically Defined, Toleragen–Based Approach for Targeting Anti–$\beta_2$–glycoprotein I Antibodies," *Abstract published in Lupus* 7 (Suppl. 2): S166–S170, located at <http://ljpc.com/abstract/abstracts_1998_chemically.html> on Jan. 19, 2004, 1 page.

Iverson, M. G. et al. (1998). "Anti–$\beta_2$ glycoprotein I (β2GPI) Autoantibodies Recognize an Epitope on the First Domain of β2GPI," *Proc Natl Acad Sci USA* 95:15542–15546.

Iverson, M. G. et al. (2002). "Use of Single Point Mutations in Domain I of $\beta_2$–Glycoprotein I to Determine Fine Antigenic Specificity of Antiphospholipid Autoantibodies" published in *The J. Immunol.* 169(12):7097–7103, abstract located at <http://www.ljpc.com/abstracts/abstract_2002_09.html> on Jan. 29, 2004, 1 page.

Iverson, M. G. et al., (2000). "Use of Single Point Mutations in Domain 1 of $\beta_2$GPI to Determine Fine Antigenic Specificity of Antiphospholipid Autoanibodies" *Abstract presented at 9th International Symposium on Antiphospholipid Antibodies*, Sep. 12–16, 2000, Tours, France, *also presented at the 12th Annual Conference of the La Jolla Immunologists*, La Jolla, California, on Oct. 24–25, 2000, located at http://www.ljpc.com/abstracts/abstract/_2000_single_point.html> on Jan. 29, 2004, 1 page.

Iverson, M. G. et al., (2001). "Use of Mutations in Domain 1 and Domain 4 of $\beta_2$GPI to Determine Fine Antigenic Specificity of Antiphospholipid Autoantibodies," *Abstract presented at 18th Congress of International Society on Thrombosis and Haemostasis*, Paris, France, on Jul. 6–12, 2001; *also presented at 27th Annual conference of La Jolla Immunologists*, La Jolla, CA, on Oct. 23–24, 2001, located at <http://www.lipc.com/abstracts/abstract_2001_07.html> on Jan. 29, 2004, 1 page.

Iverson, M. G. et al., (2002). "The Orientation of β2–Glycoprotein 1 (β2–GPI) on the Plate is Important for the Binding of Anti–β2–GPI Autoantibodies by ELISA," *Abstract presented a the 1st Tutzing Antiphospholipid Conference*, Bavaria, Germany, on Apr. 22–25, 2002, located at <http://www.ljpc.com/abstracts/abstract/_2002_07.html> on Jan. 29, 2004, 1 page.

Iverson, M. G. et al., (2002). "Use of Mutations in Domain 1 and Domain 4 of β2GPI to Determine Fine Antigenic Specificity of Antiphospholipid Autoantibodies," *Abstract presented at 3rd International Congress on Autoimmunity*, Geneva, Switzerland, on Feb. 20–24, 2002, located at <http://www.ljpc.com/abstracts/abstract_2002_03.html> on Jan. 29, 2004, 1 page.

Izumi, T. et al., (2002). "Anti–$\beta_2$–Glycoprotein I Antibody–Mediated Inhibition of Activated protein C Requires Binding of $\beta_2$–Glycoprotein I to Phospholipids," *Abstract published in Thrombosis and Haemostasis* 88(4):620–626, located at <http://www.ljpc.com/abstracts/abstract$_{13}$ 2002_11.html> on Jan. 29, 2004, 1 page.

Jones, D. S. et al. (1998). "Synthesis of a Cyclic–Thioether Peptide which Binds Anti–Cardiolipin Antibodies," *abstract published in Tetrahedron Letters* 39:6107–6110, located at <http://www.ljpc.com/abstracts/abstract_1998_synthesis.html> on Jan. 29, 2004, 1 page.

Jones, D.S. et al. (1999). "Multivalent Thioether–Peptide Conjugates: B Cell Tolerate of an Anti–Peptide Immune Response," *Abstract published in Bioconjugate Chem.* 10(3):480–488, located at <http://www.ljpc.com/abstracts/abstracts_1999_multivalent.html> on Feb. 26, 2004, 1 page.

Jones, D. S. et al. (2000). "A Convenient Synthesis of N–(tert–butyloxycarbonyl) Aminooxy Ethers," *Tetrahedron Letters* 41:1531–1533.

Jones, D. S. et al. (2001). "Synthesis of LJP 993, a Multivalent Conjugate of the N–Terminal Domain of $\beta_2$GPI and Suppression of and Anti–$\beta_{13}$ GPI Immune Response" *Absract published in Bioconjugate Chem.* 12:1012–1020, located at <http://www.ljpc.com/abstracts/abstract_2001_15.html> on Jan. 29, 2004, 1 page.

Jones, D. S. et al., (1995). "Synthetic Peptides with Binding Specificity for Antiphospholipid Antibodies," *Abstract presented at The Western Biotech Conference*, San Diego, CA, on Oct. 18–21, 1995, located at <http://www.jlpc.com/abstracts/abstract_1995_synthetic_peptides.html> on Jan. 29, 2004, 1 page.

Jones, D.S. et al., (2001). "Synthesis of a Tetravalent Conjugate of the First Domain of $\beta_2$GPI: Site Specific Attachment of a Protein to a Multivalent Platform," *Abstract present at The 221st ACS National Meeting*, San Diego, CA, on Apr. 1–5, 2001, located at <http://www.ljpc.com/abstracts/abstract_2001_06.html> on Jan. 29, 2004, 1 page.

Kandiah, D.A. et al. (1998). "Current Insights into the "Antiphospholipid" Syndrome: Clinical, Immunological, and Molecular Aspects" *Abstract published in The Advances in Immunology* 70:507–563, located at <http://www.ljpc.com/abstracts/abstract_1998_insights.html> on Jan. 29, 2004, 2 pages.

La Jolla Pharmaceutical Company Press Release (Apr. 25, 2002). "La Jolla Pharmaceutical Reports New Data at Tutzing Medical Conference on Antibody–Mediated Thrombosis," located at <http://www.ljpc.com/pressrelease/0425_02.html> on Feb. 26, 2004, 2 pages.

La Jolla Pharmaceutical Company Press Release (Oct. 27, 2002). "La Jolla Pharmaceutical Announces Results of Phase I/II Trial in Antibody–Mediated Thrombosis Patients at ACR," located at <http://www.ljpc.com/pressrelease/1027_02.html> on Feb. 26, 2004, 3 pages.

La Jolla Pharmaceutical Company Press Release (Oct. 3, 2002). "La Jolla Pharmaceutical Presents at 10th International Congress on Antiphospholipid Antibodies," located at <http://www.ljpc.com/pressrelease/1003_02.html> on Feb. 26, 2004, 2 pages.

Linnik, M. D. (1999). "Development of A B Cell Toleragen to Eliminate Pro–Thrombotic Antibodies in Antiphospholipid Syndrome," *Abstract presented at IBC's 10th Anniversary International Symposium*—AATD '99 (Advances in Anticoagulant, Antithrombotic and Thrombolytic Drugs), Boston, MA, Oct. 3–7, 1999, <http://www.ljpc.com/abstracts/abstract$_{13}$ 1999_development_bcell.html> on Jan. 29, 2004, 1 page.

Linnik, M. D. et al., (1998). "Antiphospholipid Antibodies Recognize an Epitope in Domain 1 of $\beta_2$–Glycoprotein I," *Abstract presented at 24th Annual Conference of La Jolla Immunologists*, La Jolla, CA, on Nov. 17–18, located at <http://www.ljpc.com/abstracts/abstract_1998_antiphos.html> on Jan. 29, 2004, 1 page.

Linnik, M. D. et al., (1999). "Antiphospholipid Antibodies against Domain 1 of $\beta_2$–GPI Promote Clotting by Inhibiting the Inactivation of Factor VA," *Abstract presented at The 2nd International Congress on Autoimmunity*, Tel Aviv, Israel, on Mar. 7–12, 1999, located at <http://www.ljpc.com/abstracts/abstract_1999_antiphos_against.html> on Jan. 29, 2004, 1 page.

Linnik, M. D. et al., (1999). "Antiphospholipid Antibodies Promote Clotting by Inhibiting the Inactivation of Factor Va," *Abstract presented at Keystone Symposia on B Lymphocyte Biology and <Disease*, Taos, New Mexico, on Feb. 8–14, 1999, located at <http://www.ljpc.com/abstracts/abstract_1999_antiphos_promote.html> on Jan. 29, 2004, 1 page.

Linnik, M. D. et al., (2001). "A Novel Therapeutic Approach for Treating Antiphospholipid Syndrome based on Tolerizing Anti–$\beta$2–GPI B Cells," *Abstract presented at 26th International Stroke Conference*, Fort Lauderdale, Florida, Feb. 14–16, 2001, located at <http://ljpc.com/abstracts/abstract_2001_01.html> on Jan. 29, 2004, 1 page.

Linnik, M. D. et al., (2003). "Domain Specificity of Autoantibodies to $\beta$2–Glycoprotein I in Patients With Antiphospholipid Syndrome Enrolled in a Phase 1/2 Trial With LJP 1082," *Abstract present at The 67th Annual Meeting of the American College of Rheumatology*, Orlando, Florida, on Oct. 23–28, 2003, located at <http://ljpc.com/abstracts/abstract_2003_08.html> on Jan. 29, 2004, 1 page.

Marquis, D. et al., (1998). "$\beta_2$GPI–Dependent Anticardiolipin Autoantibodies Recognize an Epitope on the First Domain of $\beta_2$GPI," *Abstract presented at The 8th International Symposium on Antiphspholipid Antibodies*, Sapporo, Japan, on Oct. 6–9, 1998, located at <http://ljpc.com/abstracts/abstract_1998_b2_GPI.html> on Jan. 29, 2004, 1 page.

McNeeley, P. A. et al. (2001). "$\beta_2$–glycoprotein I–dependent Anticardiolipin Antibodies Preferentially Bind the Amino Terminal Domain of $\beta_2$–glycoprotein I," *published in Thrombosis and Haemostasis 86:590–595, located at <http://ljpc.com/abstracts/abstract_2001_14.html>* on Jan. 29, 2004, 1 page.

McNeeley, P. A. et al., (1998). "APS Patient Sera Preferentially Recognize the First Domain of $\beta_2$–Glycoprotein I" *Abstract presented at The 8th International Symposium on Antiphospholipid Antibodies*, Sapporo, Japan, Oct. 6–9, 1998, located at <http://ljpc.com/abstracts/abstract_aps_patient.html> on Jan. 29, 2004, 1 page.

McNeeley, P. A. et al., (2002). "Domain 1-specific anti-β₂GPI Antibodies from APS Patients Contribute to Lupus Anticoagulant Activity," *Abstract presented at The 1st Tutzing Antiphospholipid Conference*, Bavaria, Germany, on Apr. 22–25, 2002, located at <http://ljpc.com/abstracts/abstract_2002_06.html> on Jan. 29, 2004, 1 page.

McNeil, P.H. et al., (1990). "Anti–phospholipid antibodies are directed against a complex antigen that includes a lipid–binding inhibitor of cogulation: β2–glycoprotein I (apoliprotein H)" *Proc. Natl. Acad. Sci.* 87:4120–4124.

McNeil, P. H. et al., (1991). "Immunology and clinical importance of antiphospholipid antibodies" Adv. Immunol., Dixon, F. J. ed., Academic Press, Inc., 49: 193–280.

Reber, G. et al., (1995). "Multicenter evaluation of nine commerical kits for the quantitation of anticardiolipin antibodies" *Thrombosis and Haemostat.* 73(3):444–452.

Roubey et al., (1996). "Comparison of an enzyme–linked immunosorbent assay for antibodies to β2–glycoprotein I and a conventional anticardiolipin immunoassay" *Arthritis & Rheumatism* 39(9):1606–1607.

Sem, D.S. et al. (1998). "Structural Characterization and Optimization of Antibody–Selected Phage Library Mimotopes of an Antigen Associated with Autoimmune Recurrent Thrombosis," *published in Biochemistry* 37:16069–16081, located at <http://ljpc.com/abstcts/abstract_2000_pharmacokinetics.html> on Jan. 29, 2004, 1 page.

Sem, D. S. et al., (1996). "Solution Structure of a Peptide from a Phage Display Library using Anti–Cardiolipin Antibody: A β₂GPI Epitope Mimic," *Abstract presented at The American Society for Biochemistry and Molecular Biology Meeting*, New Orleans, Louisiana, on Jun. 2–6, 1996, located at <http://ljpc.com/abstracts/abstract_1996_solution.html> on Jan. 29, 2004, 1 page.

Smith, E. M. et al., (1998). "Regions in Domain 1 of β₂GPI that are Important in the Binding of Anti–Cardiolipin Autoantibodies," *Abstract presented at The 8th International Symposium on Antiphospholipid Antibodies*, Sapporo, Japan, Oct. 6–9, 1998, located at <http://ljpc.com/abstracts/abstract_1998 regions.html> on Jan. 29, 2004, 1 page.

Smith, E. M. et al., (1999). "Single Point Mutations in Domain 1 of β₂–Glycoprotein I Decrease Binding of Antiphospholipid Antibodies," *Abstract presented at The 25th Annual Conference of La Jolla Immunologists*, La Jolla, California, on Nov. 8–9, 1999, located at <http://ljpc.com/abstracts/abstract_1999_single.html> on Jan. 29, 2004, 1 page.

Smith, E. M. et al., (2000). "Pharmacokinetics and Potency of Toleragenic Compounds: Screening of Candidate Compounds for the Treatment of Antiphospholipid Syndrome," *Abstract presented at The 26th Annual Conference of La Jolla Immunologists*, La Jolla, CA, on Oct. 24–25, 2000, located at <http://ljpc.com/abstracts/abstract_2000_pharmacokinetics.html> on Jan. 29, 2004, 1 page.

Steinkasserer, V. et al., (1991). "Complete nucleotide and deduced amino acid sequence of human β2–glycoprotein I" *Biochem. J.* 277:387–391.

Valesini et al., "A new player in the antiphospholipid syndrome: the β2 glycoprotein cofactor" Autoimmunity (1992) 14:105–110.

Vermylen, J. et al., (1992). "Is the antiphospholipid syndrome caused by antibodies directed against physiologically relevant phospholipid–protein complexes!" *J. Clin. Lab. Med.* 120:10–12.

Victoria, E. J. et al., "Screening of Random Peptide Phage Display Libraries with Anticardiolipin Antibodies," *Abstract presented at The Western Biotech Conference*, San Diego, California, on Oct. 18–21, 1995, located at <http://ljpc.com/abstracts/abstract_1995_screening.html> on Jan. 29, 2004, 1 page.

Yang, CD(1997). "The Fifth Domain of b2–Glycoprotein I Contains Antigenic Epitopes Recognized by Anticardiolipin Antibodies Derived From Patients With the Antiphospholipid Syndrome," *APLAR Journal of Rheumatology* 1(2):96–100.

Yu, L. et al. (1998). "A Simple and Efficient Method for the Syntheses of Thioether Cyclic Peptides," published in *Tetrahedron Letters* 39: 6633–6636, located at <http://ljpc.com/abstracts/abstract_1998_method.html> on Jan. 29, 2004, 1 page.

* cited by examiner

| | | | | | | | | | | | | | | | | | | |
|---|---|---|---|---|---|---|---|---|---|---|---|---|---|---|---|---|---|---|
| 1 | | | | | | | | | 10 | | | | | | | | | 20 |
| GGA | CGG | ACC | TGT | CCC | AAG | CCA | GAT | GAT | TTA | CCA | TTT | TCC | ACA | GTG | GTC | CCG | TTA | AAA | ACA |
| gly | arg | thr | cys | pro | lys | pro | asp | asp | leu | pro | phe | ser | thr | val | val | pro | leu | lys | thr |

1 ........ 10 .......... 20
GGA CGG ACC TGT CCC AAG CCA GAT GAT TTA  CCA TTT TCC ACA GTG GTC CCG TTA AAA ACA
gly arg thr cys pro lys pro asp asp leu  pro phe ser thr val val pro leu lys thr 30                                          40
TTC TAT GAG CCA GGA GAA GAG ATT ACG TAT  TCC TGC AAG CCG GGC TAT GTG TCC CGA GGA
phe tyr glu pro gly glu glu ile thr tyr  ser cys lys pro gly tyr val ser arg gly 50                                          60
GGG ATG AGA AAG TTT ATC TGC CCT CTC ACA  GGA CTG TGG CCC ATC AAC ACT CTG AAA TGT
gly met arg lys phe ile cys pro leu thr  gly leu trp pro ile asn thr leu lys cys 70                                          80
ACA CCC AGA GTA TGT CCT TTT GCT GGA ATC  TTA GAA AAT GGA GCC GTA CGC TAT ACG ACT
thr pro arg val cys pro phe ala gly ile  leu glu asn gly ala val arg tyr thr thr 90                                         100
TTT GAA TAT CCC AAC ACG ATC AGT TTT TCT  TGT AAC ACT GGG TTT TAT CTG AAT GGC GCT
phe glu tyr pro asn thr ile ser phe ser  cys asn thr gly phe tyr leu asn gly ala 110                                         120
GAT TCT GCC AAG TGC ACT GAG GAA GGA AAA  TGG AGC CCG GAG CTT CCT GTC TGT GCT CCC
asp ser ala lys cys thr glu glu gly lys  trp ser pro glu leu pro val cys ala pro 130                                         140
ATC ATC TGC CCT CCA CCA TCC ATA CCT ACG  TTT GCA ACA CTT CGT GTT TAT AAG CCA TCA
ile ile cys pro pro pro ser ile pro thr  phe ala thr leu arg val tyr lys pro ser 150                                         160
GCT GGA AAC AAT TCC CTC TAT CGG GAC ACA  GCA GTT TTT GAA TGT TTG CCA CAA CAT GCG
ala gly asn asn ser leu tyr arg asp thr  ala val phe glu cys leu pro gln his ala 170                                         180
ATG TTT GGA AAT GAT ACA ATT ACC TGC ACG  ACA CAT GGA AAT TGG ACT AAA TTA CCA GAA
met phe gly asn asp thr ile thr cys thr  thr his gly asn trp thr lys leu pro glu 190                                         200
TGC AGG GAA GTA AAA TGC CCA TTC CCA TCA  AGA CCA GAC AAT GGA TTT GTG AAC TAT CCT
cys arg glu val lys cys pro phe pro ser  arg pro asp asn gly phe val asn tyr pro 210                                         220
GCA AAA CCA ACA CTT TAT TAC AAG GAT AAA  GCC ACA TTT GGC TGC CAT GAT GGA TAT TCT
ala lys pro thr leu tyr tyr lys asp lys  ala thr phe gly cys his asp gly tyr ser 230                                         240
CTG GAT GGC CCG GAA GAA ATA GAA TGT ACC  AAA CTG GGA AAC TGG TCT GCC ATG CCA AGT
leu asp gly pro glu glu ile glu cys thr  lys leu gly asn trp ser ala met pro ser 250                                         260
TGT AAA GCA TCT TGT AAA TTA CCT GTG AAA  AAA GCC ACT GTG GTG TAC CAA GGA GAG AGA
cys lys ala ser cys lys leu pro val lys  lys ala thr val val tyr gln gly glu arg 270                                         280
GTA AAG ATT CAG GAA AAA TTT AAG AAT GGA  ATG CTA CAT GGT GAT AAA GTT TCT TTC TTC
val lys ile gln glu lys phe lys asn gly  met leu his gly asp lys val ser phe phe 290                                         300
TGC AAA AAT AAG GAA AAG AAG TGT AGC TAT  ACA GAG GAT GCT CAG TGT ATA GAT GGC ACT
cys lys asn lys glu lys lys cys ser tyr  thr glu asp ala gln cys ile asp gly thr 310                                         320
ATC GAA GTC CCC AAA TGC TTC AAG GAA CAC  AGT TCT CTG GCT TTT TGG AAA ACT GAT GCA
ile glu val pro lys cys phe lys glu his  ser ser leu ala phe trp lys thr asp ala TCC GAT GTA AAG CCA TGC
ser asp val lys pro cys

```
1                                                           10
GGA CGG ACC TGT CCC AAG CCA GAT GAT CCA TTT TCC ACA GTG GTC CCG TTA AAA ACA
gly arg thr cys pro lys pro asp asp pro phe ser thr val val pro leu lys thr
                                                                         20

TTC TAT GAG CCA GGA GAA GAG ATT ACG TAT TCC TGC AAG CCG GGC TAT GTG TCC CGA GGA
phe tyr glu pro gly glu glu ile thr tyr ser cys lys pro gly tyr val ser arg gly
                              30                                            40

GGG ATG AGA AAG TTT ATC TGC CCT CTC ACA GGA CTG TGG CCC ATC AAC ACT CTG AAA TGT
gly met arg lys phe ile cys pro leu thr gly leu trp pro ile asn thr leu lys cys
                              50                           60                80
                                                    70

ACA CCC AGA GTA
thr pro arg val
```

THERAPEUTIC AND DIAGNOSTIC DOMAIN 1 $\beta_2$GPI POLYPEPTIDES AND METHODS OF USING SAME

CROSS-REFERENCE TO RELATED APPLICATIONS

This application claims the priority benefit of U.S. provisional patent application Ser. No. 60/088,656, filed Jun. 9, 1998 and U.S. provisional patent application Ser. No. 60/103,088, filed Oct. 5, 1998. The priority applications are hereby incorporated herein by reference in their entirety.

STATEMENT OF RIGHTS TO INVENTIONS MADE UNDER FEDERALLY SPONSORED RESEARCH (Not applicable)

TECHNICAL FIELD

This invention relates to polypeptides and methods for diagnosing and treating antiphospholipid antibody-associated pathologies, particularly those pathologies associated with $\beta_2$GPI-dependent antiphospholipid antibodies. More specifically, the invention relates to domain 1 $\beta_2$GPI polypeptides, domain 1 $\beta_2$GPI polypeptide mimetics, domain 1 $\beta_2$GPI polynucleotides, and methods using the polypeptides, especially for detection and for use as toleragens.

BACKGROUND

Antiphospholipid (aPL) antibodies is the term generally given to describe autoantibodies that are associated with thrombosis, recurrent fetal loss and thrombocytopenia as the primary anti-phospholipid syndrome (APS) as well as autoimmune diseases such as systemic lupus erythematosus (SLE). Harris et al. (1983) Lancet 2:1211–1214; and Lockshin et al. (1985) N. Engl. J. Med. 313:152–156. APS may be primary, or secondary, meaning that it is associated with other conditions, primarily SLE. PHOSPHOLIPID-BINDING ANTIBODIES (Harris et al., eds., CRC Press, Boca Raton, Fla., 1991; McNeil et al. ADVANCES IN IMMUNOLOGY, Vol. 49, pp. 193–281 (Austen el al., eds., Academic Press, San Diego, Calif., 1991)). aPL antibodies include so-called anticardiolipin (aCL) autoantibodies, which are discussed below. aPL antibodies (including aCL antibodies) are detected in many conditions but only the $\beta_2$GPI-dependent antiphospholipid antibodies found in association with autoimmune disease require the presence of the phospholipid binding serum protein, $\beta_2$GPI. Vaarala et al. (1986) Clin. Immunol. Immunopathol. 41:8–15.

Approximately 30% of patients possessing persistent aPL antibodies have 1<suffered a thrombic event. The presence of aPL antibodies defines a group of patients within SLE who display a syndrome of clinical features consisting of one or more of thrombosis, thrombocytopenia (TCP), and fetal loss. The risk of this syndrome in SLE overall is around 25%; this risk increases to 40% in the presence of aPL antibodies and decreases to 15% in their absence. Because aPL antibodies were thought to be directed at phospholipids in plasma membranes, it has been postulated that they may exert direct pathogenic effects in vivo by interfering with hemostatic processes that take place on the phospholipid membranes of cells such as platelets or endothelium. In patients with APS, the fact that aPL (including aCL) antibodies appear to be the only risk factor present is further evidence that these antibodies have a direct pathogenic role. Induction of APS by passive transfer of mice with human aPL antibodies is the best evidence yet that aPL antibodies are directly pathogenic. Bakimer et al. (1992) J. Clin. Invest. 89:1558–1563; Blank et al. (I 991) Proc. Natl. Acad. Sci. 88:3069–3073. Estimates vary but in about 15% of all stroke patients, aPL antibodies are thought to be an important contributing factor.

The clear correlation between presence of these antibodies with a number of disorders compels their detection and measurement. However, measurement of aPL antibodies in the clinical environment is still an imperfect art and therefore presents significant problems. A commercially available set of standard antisera (APL Diagnostics, Inc., Louisville, Ky.) allow generation of a standard curve for comparison of assays performed in various laboratories. A great deal of inconsistency exists, however, between the results obtained at these laboratories regarding the exact GPL and MPL, the unit of measurement for IgG and IgM antiphospholipid antibodies, respectively, ratings for given sera and the levels of GPL and MPL that are categorized as high (80 or greater), medium (20–80), low (10–20) or normal (0–10). The available commercial kits vary greatly in the values assigned to the commercially available standards. Reber et al. (1995) Thrombosis and Haemostat. 73:444–452.

The exact nature of the antigenic specificity of aPL autoantibodies is controversial, and is reflected in the evolving nomenclatures used for these antibodies. At first these autoantibodies were thought to be directed against anionic phospholipids, hence the name "anticardiolipin antibodies". Gharavi et al. (1987) Ann. Rheum. Dis. 46 m: 1–6. It then became apparent that $\beta_2$GPI played an important role in the antigenic specificity of aPL (including aCL) antibodies. Vermylen et al (1992) J. Lab. Clin. Med. 120:10; McNeil et al. (1990) Proc. Natl. Acad Sci. USA 87:41204124. These observations indicate that these antibodies are more properly called "$\beta_2$GPI-dependent antiphospholipid autoantibodies", which is the term used in this specification.

The reports that $\beta_2$GPI played a role, as a cofactor, in the binding of $\beta_2$GPI-Us dependent antiphospholipid antibody coupled with some reports that $\beta_2$GPI-dependent antiphospholipid antibodies could bind $\beta_2$GPI itself has led to conflicting interpretations as to the nature of the antigenic site recognized by these antibodies. However, the role $\beta_2$GPI played has remained unclear, and several explanations have been suggested. Some groups have concluded that $\beta_2$GPI-dependent antiphospholipid antibodies recognize a complex antigen that includes both $\beta_2$GPI and anionic phospholipid, whereas others have observed $\beta_2$GPI-dependent antiphospholipid binding to $\beta_2$GPI in the absence of phospholipid. McNeil et al. (1990) Proc. Natl. Acad Sci. USA 87:4120–4124; Galli et al. (1990) Lancet 335:1544; Roubey et al (1995) J. Immun. 154(2): 954–960; Arvieux et al. (1991) J. Immunol. Methods 143:223. A number of explanations have been offered to explain these differences. Galli et al. postulate that because $\beta_2$GPI dependent antiphospholipid antibodies are low affinity antibodies to $\beta_2$GPI they require engagement of both combining sites on a given IgG molecule by a multivalent solid phase antigen. Galli et al. (1990). They further argue that under certain conditions, for example gamma irradiation of microtiter wells, that sufficient $\beta_2$GPI can be immobilized to allow for these low affinity antibodies to bind. Others argue that a cryptic epitope, recognized by $\beta_2$GPI-dependent antiphospholipid antibodies, is generated when $\beta_2$GPI binds to either gamma irradiated well or to wells coated with cardiolipin. Matsuura et al. (1994) J. Exp. Med. 179:457.

$\beta_2$GPI is a 50 kilodalton plasma glycoprotein that displays several properties ° defining an anti-coagulant, such as inhibition of contact activation of the intrinsic coagulation pathway, platelet prothrombinase activity, and ADP-induced platelet activation. Roubey (1996) *Arthritis Rheum.* 39:1444; Valesinit et al. (1992) *Autoimmunity* 14:105. The amino acid sequence of $\beta_2$GPI has been determined. Lozier et al. (1984) *Proc. Natl. Acad. Sci. USA* 81:3640; Steinkasserer et al. (1991) *Biochem. J.* 277:387. $\beta_2$GPI is composed of five homologous domains. Four of them are composed of approximately 60 amino acids that contain highly conserved cystines, prolines and tryptophans. Lozier et al. (1984) *Proc. Natl. Acad Sci. USA* 81:3640; Steinkasserer et al. (1991) *Biochem. J.* 277:387–391. This protein structural motif was first described in $\beta_2$GPI and is characterized by its length, independent folding, and by a framework with the homologous location of four half-cystine residues involved in the formation of two internal disulfide bridges; two prolines; two phenylalanine, tyrosine or histidine residues; two glycines; and one leucine or valine.

These repeating motifs were designated as sushi structures because of their shape or are sometimes referred to as short consensus repeats. Reid et al. (1989) *Immunol. Today* 10:177; Ichinose et al. (1990) *J. Biol. Chem.* 265:13411–14. The fifth domain contains 82 amino acid residues and 6 half-cystines.

In addition to the above-discussed controversy surrounding the nature of the antigenic specificity of $\beta_2$GPI-dependent antiphospholipid antibodies, there has been considerable controversy regarding the nature and location of epitopes recognized by $\beta_2$GPI-dependent antiphospholipid antibodies in $\beta_2$GPI. It has been suggested that the phospholipid-binding site of $\beta_2$GPI is located in the fifth domain. Hunt et al. (1993) *Proc. Natl. Acad. Sci. USA* 90:2141. Hunt et al. also reported on the structural differences between an active form of $\beta_2$GPI and an inactive form of $\beta_2$GPI that lacked $\beta_2$GPI-dependent antiphospholipid cofactor activity and concluded that the putative epitope for $\beta_2$GPI-dependent antiphospholipid antibodies was most likely to be in the fifth domain of $\beta_2$GPI. Hunt et al. (1994) *J. Immunol.* 152:653–659. Other groups have used recombinant $\beta_2$GPI proteins to attempt to locate the antigenic site of $_2$GPI-dependent antiphospholipid antibodies. Two of these groups produced $\beta_2$GPI mutant proteins from which various domains had been deleted in a baculovirus expression system. Both groups concluded that the epitope for $\beta_2$GPI-dependent antiphospholipid antibodies was cryptic and that domain 4 may be dominantly involved in the exposure of the epitope. Igarashi et al. (1996) *Blood* 87:3262–3270; George et al. (1998) *J. Immunol.* 160:3917–3923. Another group expressed $\beta_2$GPI mutant proteins from which various domains had been deleted in *Escherichia coli* and concluded that domain 5 contained epitopes recognized by $\beta_2$GPI-dependent antiphospholipid antibodies. Yang et al. (1997) *APLAR J. Rheumatol.* 1:96–100.

There is a serious need for improved detection systems and toleragens for $\beta_2$GPI-dependent antiphospholipid antibody-mediated conditions.

All references cited herein are incorporated by reference in their entirety.

DISCLOSURE OF THE INVENTION

The invention provides domain 1 $\beta_2$GPI polypeptides, polynucleotides encoding these polypeptides, mimetics of domain 1 $\beta_2$GPI polypeptides, compositions, and methods using these polypeptides, polynucleotides, and mimetics.

Accordingly, in one aspect, the invention provides polypeptides comprising a domain 1 $\beta_2$GPI polypeptide, wherein the polypeptide specifically binds to a $\beta_2$GPI-dependent antiphospholipid antibody, wherein it is understood that the polypeptide does not consist of the amino acid sequence of intact $\beta_2$GPI, as depicted in FIG. 1 (SEQ ID NO: I), and further does not consist of domains 1, 2, and 3 or domains 1, 2, 3 and 4 of $\beta_2$GPI. In some embodiments, the polypeptide comprises fragments of domain 1, such as are shown in Table 1. In other embodiments, the polypeptide comprises a conformational epitope. In yet other embodiments, the polypeptide consists of domain 1.

In another aspect, the invention provides a polypeptide comprising a domain $\beta_2$GPI polypeptide, wherein the polypeptide lacks a (detectable) T cell epitope, said T cell epitope capable of activating T cells in an individual having $_2$GPI dependent antiphospholipid antibodies.

The invention also provides conjugates, fusions, and/or polymeric forms of any of the domain 1 $\beta_2$GPI polypeptide(s) (or polypeptides comprising $\beta_2$GPI polypeptide(s)). In preferred embodiments, a domain 1 $\beta_2$GPI polypeptide(s) (particularly those lacking a T cell epitope) is conjugated to an appropriate multi-valent platform molecule, which may be proteinaceous or non-proteinacecous.

In another aspect, the invention provides polynucleotides (including isolated naturally-occurring and non-naturally occurring polynucleotides) encoding any of the polypeptide embodiments of this invention. The polynucleotides may be isolated, in cloning or expression vectors, and/or in suitable host cells.

In another aspect, the invention provides mimetics of a domain 1 GPI polypeptide, said mimetics able to specifically bind to an antibody which specifically binds to a domain 1 $\beta_2$GPI polypeptide (i.e., a mimetic shares an epitope with a domain 1 $\beta_2$GPI polypeptide). A mimetic may be a polypeptide or any of a number of substances which are described herein, including organic and inorganic molecules. A mimetic may or may not contain a T cell epitope, said T cell epitope capable of activating T cells in an individual having $\beta_2$GPI dependent antiphospholipid antibodies.

In another aspect, the invention provides compositions comprising any of the polypeptide, polynucleotide and/or mimetic embodiments described herein. In some embodiments, the compositions also contain a pharmaceutically acceptable excipient. In some embodiments, an effective amount of the polypeptide or polypeptide is contained within a composition, wherein an effective amount is an amount sufficient to induce tolerance. In some embodiments (for detection purposes), an effective amount is an amount sufficient to detect an antibody that binds to a domain 1 $\beta_2$GPI polypeptide (or mimetic).

In another aspect, the invention provides methods for detection of a $\beta_2$GPI-dependent antiphospholipid antibody (or an antibody that specifically binds to a domain 1 $\beta_2$GPI polypeptide(s)) in a sample comprising (a) contacting antibody in the sample with a domain 1 $\beta_2$GPI polypeptide(s) (or a polypeptide comprising a domain 1 $\beta_2$GPI polypeptide(s) or a domain 1 $\beta_2$GPI mimetic(s)) under conditions that permit the formation of a stable antigen-antibody complex; and (b) detecting stable complex formed in step (a), if any.

In another aspect, the invention provides methods of inducing tolerance in an individual which comprise administering an effective amount of a domain 1 $\beta_2$GPI polypeptide(s) to an individual, particularly a domain 1 $\beta_2$GPI polypeptide(s) that lacks a T cell epitope, wherein an effective amount is an amount sufficient to induce tolerance.

BRIEF DESCRIPTION OF THE DRAWINGS

FIG. 1 depicts the nucleotide (SEQ ID NO:1) and amino acid (SEQ ID NO:2) sequence of β$_2$GPI. Numbers above the lines indicate amino acid positions.

FIG. 2 depicts the nucleotide (SEQ ID NO:3) and amino acid (SEQ ID NO:4) sequence of domain 1 of β$_2$GPI. Numbers above the lines indicate amino acid positions.

MODES FOR CARRYING OUT THE INVENTION

Figure 3:
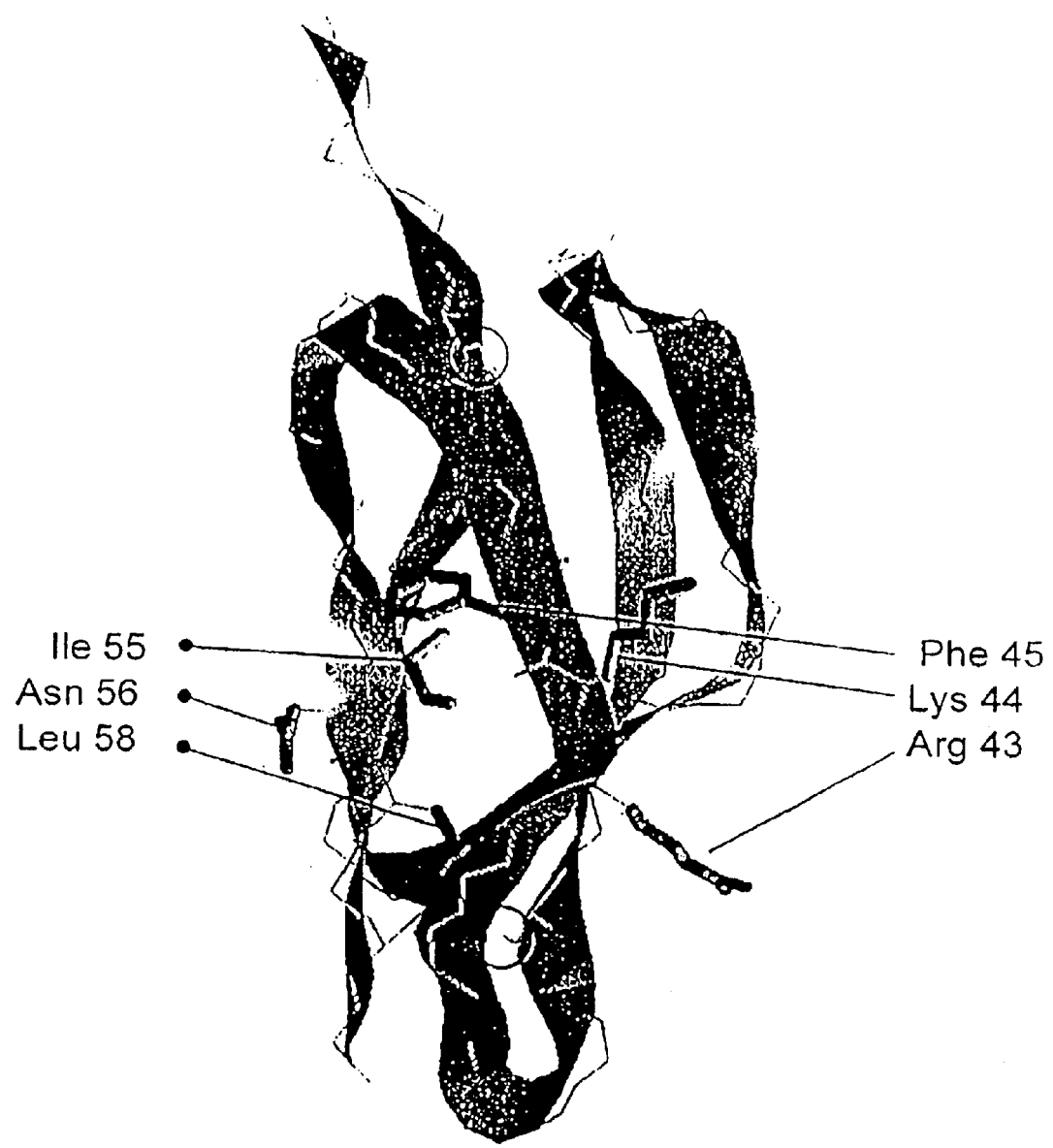
FIG. 3 is a model of the tertiary structure of domain 1 of β$_2$GPI, including key amino acids in binding to β$_2$GPI-dependent antiphospholipid antibody.

We have discovered that domain 1 of β$_2$GPI specifically binds to β$_2$GPI-dependent antiphospholipid antibody (i.e., contains an epitope(s) of a β$_2$GPI-dependent antiphospholipid antibody). This finding is especially significant in view of the existing literature which described only domains 5 and 4 as important for this binding. See, e.g., George et al. (1998) and Yang et al. (1997). We have also discovered that domain 1 of β$_2$GPI binds to β$_2$GPI-dependent antiphospholipid antibodies from at least 100 different β$_2$GPI-dependent antiphospholipid antibodies which is especially significant and important for the detection/diagnostic context as well as the toleragen context, as domain 1 β$_2$GPI polypeptide(s) may thus be useful for a broad range of the population carrying β$_2$GPI-dependent antiphospholipid antibodies. Further, we have found that particular peptides of domain 1 (described herein) appear to bind to β$_2$GPI-dependent antiphospholipid antibody specifically.

Accordingly, the invention provides polypeptides comprising domain 1 β$_2$GPI polypeptides (including isolated domain 1) which bind specifically to a 2GPI-dependent antiphospholipid antibody. The invention also provides polypeptides consisting essentially of domain 1 β$_2$GPI polypeptides which bind specifically to a β$_2$GPI-dependent antiphospholipid antibody. The polypeptides of the invention are useful for detection of $\beta_2$GPI-dependent antiphospholipid antibody (in the diagnostic, prognostic, and/or monitoring context), and are also useful as toleragens. In some embodiments, particularly in the toleragen context, the $\beta_2$GPI polypeptide(s) lacks a T cell epitope and/or is in multivalent form, such as conjugated to a platform molecule. The invention also provides polynucleotides encoding $\beta_2$GPI polypeptide(s). Such polynucleotides may be used for producing $\beta_2$GPI polypeptide(s), whether in vitro or in vivo. The invention also provides mimetics of a domain 1 $\beta_2$GPI polypeptide(s), which share recognition (i.e., epitope) with a $\beta_2$GPI-dependent antiphospholipid antibody. The invention also provides compositions comprising domain 1 $\beta_2$GPI polypeptide(s), polynucleotides encoding domain 1 $\beta_2$GPI polypeptide(s), and/or mimetic(s). The invention further provides methods using $\beta_2$GPI polypeptide(s) and/or mimetic(s), such as for detection or inducing tolerance (i.e., the induction of B cell tolerance).

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991).

Definitions

A "$\beta_2$GPI domain 1 polypeptide" is a polypeptide that specifically binds a $\beta_2$GPI-dependent antiphospholipid antibody and has at least five contiguous amino acids depicted in FIG. 2. (SEQ. ID. NO:4; domain 1). A $\beta_2$GPI domain 1 polypeptide can be shown to bind specifically to a 52GPI-dependent antiphospholipid antibody using standard assays known in the art, such as competitive inhibition assays, which are described herein as well as in the art. The term "$\beta_2$GPI domain 1 polypeptide" encompasses various embodiments (many of which are described herein), including, but not limited to, SEQ ID NO:4; fragments of SEQ ID NO:4; extensions, insertions, and/or deletions of SEQ ID NO:4; sequence variants of SEQ ID NO:4. Thus, the term "$\beta_2$GPI domain 1 polypeptide" is meant to describe a class of domain 1-based molecules which exhibit the requisite functionality. As such, a $\beta_2$GPI domain 1 polypeptide may have at least 5 (as noted above), at least 6, at least 10, at least 12, at least 15, at least 20, at least 25, at least 30, at least 40, and/or at least 60 contiguous amino acids shown in FIG. 2 (SEQ ID NO:4). A $\beta_2$GPI domain 1 polypeptide may also comprise different regions of domain 1, such that collectively these regions are able to specifically bind a $\beta_2$GPI-dependent antiphospholipid antibody (such as in producing a conformational epitope). As discussed below, in some embodiments, a "$\beta_2$GPI domain 1 polypeptide" also lacks a (any) detectable T cell epitope. For purposes of this invention, the T cell epitope is defined as capable of activating T cells in an individual with $\beta_2$GPI dependent antiphospholipid antibodies.

A polypeptide that "specifically binds" to an antibody is a term well understood in the art, and methods to determine such specific binding are also well known in the art. A molecule is said to exhibit "specific binding" if it reacts or associates more frequently, more rapidly, with greater duration and/or with greater affinity with a particular cell or substance than it does with alternative cells or substances. An antibody "specifically binds" to a target if it binds with greater affinity, avidity, more readily, and/or with greater duration than it binds to other substances.

A "$\beta_2$GPI dependent antiphospholipid antibody" is any antibody which specifically binds to $\beta_2$GPI. As discussed above, the nomenclature used in the clinical arts and the literature employ alternative designations for these antibodies, such as "aPL" and "aCL" antibodies, which are included in the definition of the term "4$_2$GPI-dependent antiphospholipid antibody", as long as the requisite binding property is present (i.e., the terms "aPL" and "aCL" antibodies include $\beta_2$GPI-dependent antiphospholipid antibodies). As clearly indicated in the definition of "antibody" provided herein, a "$\beta_2$GPI-dependent antiphospholipid antibody" encompasses fragments that contain the variable region, such as Fab fragments, as long as the ability to specifically bind $\beta_2$GPI is preserved. As discussed below, it is understood that specific binding to any $\beta_2$GPI-dependent antiphospholipid antibody is sufficient, although it may be preferable for a $\beta$2GPI domain 1 polypeptide to bind to more than one, preferably at least two, preferably at least five, more preferably at least ten, even more preferably at least 20 different $\beta_2$GPI-dependent antiphospholipid antibodies.

An "antibody" (interchangeably used in plural form) is an immunoglobulin molecule capable of specific binding to a target, such as a polypeptide, through at least one antigen recognition site, located in the variable region of the immunoglobulin molecule. As used herein, the term encompasses not only intact antibodies, but also fragments thereof (such as Fab, Fab', F(ab')$_2$, Fv), single chain (ScFv), mutants thereof, fusion proteins, humanized antibodies, and any other modified configuration of the immunoglobulin molecule that comprises an antigen recognition site of the required specificity.

"Intact $\beta_2$GPI" refers to the amino acid sequence of the entire molecule of $\beta_2$GPI (depicted in FIG. 1 and SEQ ID NO:2). The polynucleotide and polypeptide sequences of 2GPI are also publicly available in the literature and in GeneBank (Accession No. X58100).

A "fusion polypeptide" is a polypeptide comprising regions in a different position than occurs in nature. The regions may normally exist in separate proteins and are brought together in the fusion polypeptide, or they may normally exist in the same protein but are placed in a new arrangement in the fusion polypeptide. A fusion polypeptide may also arise from polymeric forms, whether linear or branched, of domain 1 $\beta_2$GPI polypeptide(s).

A "T cell epitope" is a term well understood in the art and means a binding site for a T cell, more specifically, a polypeptide sequence or chemical structure that activates a T cell(s). Methods of determining the presence of T cell epitopes are also well known in the art and are described herein. It is understood that, over time, more sensitive assays may be developed to detect the presence of T cell epitopes, and that specifying the lack of T cell epitopes is dependent on the type of detection system used. For purposes of this invention, "lacking" a T cell epitope is taken to mean that a T cell epitope is not detectable using standard assays in the art, particularly as of the initial filing date of this application. It is also understood that, for purposes of this invention, a "T cell epitope" is one that is capable of stimulating T cells in an individual who has $\beta_2$GPI-dependent antiphospholipid antibodies.

The terms "polynucleotide" and "nucleic acid", used interchangeably herein, refer to a polymeric form of nucleotides of any length, either ribonucleotides or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be a oligodeoxynucleoside phosphoramidate (P-NH2) or a mixed phosphoramidate-phosphodiester oligomer. A phosphorothiate linkage can be used in place of a phosphodiester linkage. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

"Naturally occurring" refers to an endogenous polynucleotide or polypeptide sequence, i.e., one found in nature. The term includes alleles and allelic forms of the encoded protein, as well as full-length as processed polynucleotides and polypeptides. Processing can occur in one or more steps, and these terms encompass all stages of processing. Conversely, a "non-naturally occurring" sequence refers to all other sequences, i.e., ones which do not occur in nature, such as recombinant sequences.

A "host cell" includes an individual cell or cell culture which can be or has been a recipient for vector(s) or for incorporation of polynucleotides and/or proteins. Host cells include progeny of a single host cell, and the progeny may not necessarily be completely identical (in morphology or in genomic of total DNA complement) to the original parent cell due to natural, accidental, or deliberate mutation. A host cell includes cells transfected in vivo with a polynucleotide(s) of this invention.

"Transformation" or "transfection" refers to the insertion of an exogenous polynucleotide into a host cell, irrespective of the method used for the insertion, for example, lipofection, transduction, infection or electroporation. The exogenous polynucleotide may be maintained as a non-integrated vector, for example, a plasmid, or alternatively, may be integrated into the host cell genome.

As used herein, the term "mimetic" (also termed an "analog") means a biological or chemical compound which specifically binds to a $\beta_2$GPI-dependent antiphospholipid antibody to which a domain 1 $\beta_2$GPI polypeptide binds specifically. A "mimetic" shares an epitope, or binding specificity, with a domain 1 $\beta_2$GPI polypeptide. A mimetic may be any chemical substance which exhibits the requisite binding properties, and thus may be, for example, a simple or complex organic or inorganic molecule; a polypeptide; a polynucleotide; a carbohydrate; a lipid; a lipopolysaccharide; a lipoprotein, or any combination of the above, including, but not limited to, a polynucleotide-containing polypeptide; a glycosylated polypeptide; and a glycolipid. The term "mimetic" encompasses the term "mimotope", which is a term well known in the art.

An "individual" is a vertebrate, preferably a mammal, more preferably a human. Mammals include, but are not limited to, farm animals, sport animals, pets, primates, mice and rats.

"B cell anergy" is a term well understood in the art and means unresponsiveness of those B cells requiring T cell help to produce and secrete antibody and includes, but is not limited to, clonal deletion of immature and/or mature B cells and/or the inability of B cells to produce antibody.

"Inducing tolerance" means a reduction and/or stabilization of the extent of an immune response to an immunogen. An "immune response" may be humoral and/or cellular, and may be measured using standard assays known in the art. For purposes of this invention, the immune response is generally reflected by the presence of 1$\beta_2$GPI-dependent antiphospholipid antibodies. Quantitatively the reduction (as measured by reduction in antibody production) is at least about 25%, more preferably at least about 50%, more preferably at least about 75%, more preferably at least about 90%, even more preferably at least about 95%, and most preferably 100%. It is understood that the tolerance is antigen-specific, and applies for purposes of the invention to those individuals having $\beta_2$GPI-dependent antiphospholipid antibodies. "Inducing tolerance" also includes slowing and/or delaying the rate of increase of antibody level.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides. The term "biological sample" encompasses a clinical sample, and also includes cells in culture, cell supernatants, cell lysates, serum, plasma, biological fluid, and tissue samples.

A "stable complex" formed between any two or more components in a biochemical reaction, refers to a duplex or complex that is sufficiently long-lasting to persist between formation of the duplex or complex and subsequent detection, including any optional washing steps or other manipulation that may take place in the interim.

An "isolated" or "purified" polypeptide or polynucleotide is one that is substantially free of the materials with which it is associated in nature. By substantially free is meant at least 50%, preferably at least 70%, more preferably at least 80%, even more preferably at least 90% free of the materials with which it is associated in nature.

A polynucleotide is said to "encode" a polypeptide if, in its native state or when manipulated by methods well known to those skilled in the art, it can be transcribed and/or translated to produce the polypeptide or a fragment thereof. For purposes of this invention, and to avoid cumbersome referrals to complementary strands, the anti-sense (or complementary) strand of such a polynucleotide is also said to encode the sequence; that is, a polynucleotide sequence that "encodes" a polypeptide includes both the conventional coding strand and the complementary sequence (or strand).

An "effective amount" (when used in the toleragenic context) is an amount sufficient to effect beneficial or desired clinical results. An effective amount can be administered in one or more administrations. For purposes of this invention, an effective amount of a domain 1 $\beta_2$GPI polypeptide(s) is an amount sufficient to induce tolerance, particularly with respect to $\beta_2$GPI-dependent antiphospholipid antibodies. In terms of treatment, an "effective amount" of a domain 1 $\beta_2$GPI polypeptide(s) is an amount sufficient to palliate, ameliorate, stabilize, reverse, slow or delay progression of a $\beta_2$GPI-dependent antiphospholipid-associated disease state (i.e., a state in which $\beta_2$GPI-dependent antiphospholipid antibodies indicate potential or actual pathology). Detection and measurement of indicators of efficacy are generally based on measurement of $\beta_2$GPI-dependent antiphospholipid antibody and/or clinical symptoms associated with the disease state, such as arterial or venous thrombosis, fetal loss, transient ischemic attack, cerebrovascular accidents, amaurosis fugax (monocular vision), autoimmune hemolytic anemia, cardiac valve lesions, myocardial infarction, thrombocytopenia, and migraine conditions.

As used herein "valency platform molecule" means a nonimmunogenic molecule containing sites which allow the attachment of a discreet number of polypeptides (in this invention, domain 1 $\beta_2$GPI polypeptides) and/or mimetic(s).

"Nonimmunogenic", when used to describe the valency platform molecule, means that the valency platform molecule fails to elicit an immune response, and/or fails to elicit a sufficient immune response, when it is administered by itself to an individual. The degree of acceptable immune response depends on the context in which the valency platform molecule is used, and may be empirically determined.

As used herein "pharmacophore" means the three dimensional orientation and chemical properties of key groups involved in binding of a domain 1 $\beta_2$GPI polypeptide to the antibody target.

Domain 1 $\beta_2$GPI Polypeptides of the Invention

The invention provides domain 1 $\beta_2$GPI polypeptide(s). As described above, a domain 1 $\beta_2$GPI polypeptide (a) contains at least five (or more) contiguous amino acids of FIG. 2 (SEQ ID NO:4), which depicts domain 1; and (b) specifically binds to a $\beta_2$GPI-dependent antiphospholipid antibody (i.e., one or more $\beta_2$GPI-dependent antiphospholipid antibodies). A model of the three-dimensional structure of domain 1 $\beta_2$GPI is presented in FIG. 3 (based on actual structure of factor H1 sushi domain 16 as determined by nmr (Norman et al. (1991) *J. Mol. Biol.* 219:717; Barlow et al. (1991) *Biochem.* 30:997), and residues which may be involved in structural integrity and/or antibody binding, as determined by mutagenesis studies, including those presented herein, are indicated. With respect to all polypeptide embodiments of the invention, it is understood that the polypeptides of the invention do not include native, intact $\beta_2$GPI, or any other previously isolated and characterized form of $\beta_2$GPI, such as domain deletion mutants (i.e., domains 1, 2, 3; domains 1, 2, 3, 4).

In one embodiments, the invention includes a domain 1 $\beta_2$GPI polypeptide containing (or, in some embodiments, consisting of or consisting essentially of) a domain 1 $\beta_2$GPI polypeptide, provided that the polypeptide does not consist of (a) intact $\beta_2$GPI (SEQ ID NO:2), (b) domains 1, 2, and 3; or (c) domains 1, 2, 3, and 4.

In one embodiment, the invention includes a polypeptide consisting of (or, in some embodiments, consisting essentially of) the amino acid sequence shown in FIG. 2 (SEQ ID NO:4), which represents domain 1. We have shown that only those domain deletion $\beta_2$GPI polypeptides containing domain 1 are able to specifically bind to a $\beta_2$GPI-dependent antiphospholipid antibody, and that domain 1 alone is able to bind a $\beta_2$GPI-dependent antiphospholipid antibody, as described in Example 1. For purposes of this invention, domain 1 of $\beta_2$GPI is generally about amino acid 1 to about amino acid 64 of $\beta_2$GPI (FIG. 1). Alternatively, and also for purposes of this invention, domain 1 (and accordingly a domain 1 $\beta_2$GPI polypeptide of the invention) may range from (a) about the first cysteine to about the fourth cysteine (when determined from the N-terminus); (b) about the N terminus to about the fifth cysteine (more precisely, the last amino acid before the fifth cysteine); (c) about the first cysteine to about the fifth cysteine. In some embodiments, an additional cysteine may be added in any suitable position, to serve as a reactive group for conjugation. Accordingly, a additional cysteine (which in some embodiments is the fifth cysteine of $\beta_2$GPI) may be included in any position, particularly near or at the C terminus or N terminus. A domain 1 $\beta_2$GPI polypeptide may also comprise (or consist of, or consist essentially of) any of the following: (a) amino acid 1 to amino acid 59 of SEQ ID NO:4; (b) amino acid 2 to amino acid 60 of SEQ ID NO:4; (c) amino acid 2 to amino acid 63 of SEQ ID NO:4; (d) amino acid 1 to amino acid 66 of SEQ ID NO: 1; (e) amino acid 4 to amino acid 66 of SEQ ID NO: 1; (e about amino acid 1 to about amino acid 60 of SEQ ID NO:4; (g) about amino acid 1 to about amino acid 66 of SEQ ID NO:1 We have found that domain 1 $\beta_2$GPI polypeptides which contain the fifth cysteine are particularly convenient for conjugation (discussed below). For those embodiments containing (comprising) the first four cysteines of $\beta_2$GPI, it is understood that, generally, the amino acid sequence between the cysteines should be such that the appropriate disulfide bridges are formed, while the amino acid sequences flanking the cysteines (i.e., the N terminus and C terminus amino acids) may be any sequence (as long as the requisite structure which allows binding to antibody is preserved).

In other embodiments, the invention includes a polypeptide comprising any of the polypeptides shown in Table 1 (SEQ ID NOS:5–11). Our experiments (described in Example 3) demonstrate that these polypeptides are able to bind specifically to a $\beta_2$GPI-dependent antiphospholipid antibody.

With respect to all polypeptide embodiments of this invention, the polypeptide(s) specifically binds to a $\beta_2$GPI-dependent antiphospholipid antibody. Specific binding to a $\beta_2$GPI-dependent antiphospholipid antibody may be determined using standard techniques in the art, such as competitive binding assays. For example, microtiter plates may be coated with $\beta_2$GPI (whether naturally-occurring or recombinant, as long as the recombinant molecule displays the requisite binding properties), and test polypeptide added in varying concentrations. Affinity purified $\beta_2$GPI-dependent antiphospholipid antibody is then added, and binding allowed to occur. The amount of bound antibody is determined by detection systems such as alkaline phosphatase conjugated anti-human IgG, or radioactivity. Specific binding is indicated by the ability of the test polypeptide to compete for binding to $\beta_2$GPI. Examples 1 and 3 provide exemplary assays for detection of competitive binding. Specific binding may also be determined by direct binding assays, which are known in the art and exemplified in Examples 1 and 3.

It is understood that, for purposes of this invention, the domain 1 $\beta_2$GPI polypeptide need only bind to one $_2$GPI-dependent antiphospholipid antibody, although it may be desirable (for example, in the detection context), for the domain 1 β$_2$GPI polypeptide to bind to more than one β$_2$GPI-dependent antiphospholipid antibody. The source of the β$_2$GPI-dependent antiphospholipid antibody is generally from an individual, and the antibody sequence may vary from individual to individual. It is also understood that specifically binding to a β$_2$GPI-dependent antiphospholipid antibody may be demonstrated by using a fragment or other recombinant product of a β$_2$GPI-dependent antiphospholipid antibody, such as an Fab fragment, or single chain variable region constructs (scFv), which are known in the art.

Accordingly, in some embodiments, a domain 1 β$_2$GPI polypeptide binds to more than one β$_2$GPI-dependent antiphospholipid antibody (i.e., at least 2, at least 5, at least 10, at least 20, at least 50 or more). These embodiments are especially useful for detection, as these polypeptide(s) may be used to detect over a broader spectrum of individuals who may carry a $\beta_2$GPI-dependent antiphospholipid antibody.

TABLE 1

Fragments of domain 1 which specifically bind to $\beta_2$GPI-dependent antiphospholipid antibody

| Sequence | SEQ ID NO: |
|---|---|
| CTPRVC | 5 |
| FSTVVP | 6 |
| KPDDLP | 7 |
| GRTCPK | 8 |
| TLKCTP | 9 |
| ICPLTG | 10 |
| FICPLT | 11 |
| ITYSCK | 12 |

In some embodiments, a domain 1 $\beta_2$GPI polypeptide contains a sushi structure. "Sushi domain" is understood by those in the art and is generally characterized by (a) containing certain residues (such as proline, phenylalanine, tryosine, glycine, leucine, valine and/or histidine) which coil the polypeptide chain into a circular structure; (b) generally having a molecular weight of approximately 6 kD; and (c) containing a β folded structure. Ichmose et al. (1990) *J. Biol. Chem.* 1265:13411.

It is also understood that a domain 1 $\beta_2$GPI polypeptide may bind to $\beta_2$GPI-dependent antiphospholipid antibody via a conformational epitope(s). Accordingly, in some embodiments, a domain 1 $\beta_2$GPI polypeptide comprises (a) amino acids 55, 56, and 58 (ile; asn; leu) of FIG. 3 (amino acids 55, 56, and 58 of SEQ ID NO:4); (b) amino acids 43–45 (arg; lys; phe) of FIG. 3 (amino acids 43 to 45 of SEQ ID NO:4); (c) amino acids 40 to 45 of SEQ ID NO:4 (gly; gly; met; arg; lys; phe), preferably amino acids 38–44 of FIG. 3 (amino acids 38 to 44 of SEQ ID NO:4); and/or (d) amino acid 19 (lys) of FIG. 3 (amino acid 19 of SEQ ID NO:4), preferably (a) and (b); preferably (a) and (c); preferably (b) and (c); preferably (a) and (d); preferably (b) and (d); preferably (c) and (d); preferably (a), (b) and (d); preferably (a), (c) and (d); preferably (b), (c) and (d); preferably (a), (b) and (c); preferably (a), (b), (c) and (d). We have found through our mutagenesis studies that these amino acids may be critical for binding, either collectively or individually.

The size of a domain 1 $\beta_2$GPI polypeptide (or a polypeptide comprising a domain 1 $\beta_2$GPI polypeptide may vary widely, as long as the requisite functionality (based on specific binding to a $\beta_2$GPI-dependent antiphospholipid antibody) is met. For example, the length required to effect specific binding to a $\beta_2$GPI-dependent antiphospholipid antibody could be as small as, for example, a 5-mer amino acid sequence. Our data has shown amino acid sequences as small as a 6-mer can specifically bind to a $\beta_2$GPI-dependent antiphospholipid antibody (Example 3).

In some embodiments, the domain 1 $\beta_2$GPI polypeptide(s) (and the polypeptide comprising or consisting essentially of a domain 1 $\beta_2$GPI polypeptide(s)) is less than about 350 amino acids in length, preferably less than about 300 amino acids in length, preferably less than about 250 amino acids in length, preferably less than about 200 amino acids in length, preferably less than about 160 amino acids in length, preferably less than about 150 amino acids in length, preferably less than about 125 amino acids in length, preferably less than about 115 amino acids in length, preferably less than about 110 amino acids in length, preferably less than about 100 amino acids in length, preferably less than about 75 amino acids in length, preferably less than about 60 amino acids in length, preferably less than about 50 amino acids in length, preferably less than about 25 amino acids in length, preferably less than about 15 amino acids in length, preferably less than about 10 amino acids in length.

It is understood that a domain 1 $\beta_2$GPI polypeptide(s) may be associated with, conjugated with, and/or connected to other domain 1 $\beta_2$GPI polypeptide(s) (whether these domain 1 $\beta_2$GPI polypeptide(s) are the same or different), as well as other domains of $\beta_2$GPI. Accordingly, the invention encompasses polymeric forms of domain 1 $\beta_2$GPI polypeptide(s). As used herein, a polymeric form of a domain 1 $\beta_2$GPI polypeptide contains a plurality (i.e., more than 1) domain 1 $\beta_2$GPI polypeptide(s). In one embodiment, linear polymers of domain 1 $\beta_2$GPI polypeptides are provided. In another embodiment, branched polymers of domain 1 $\beta_2$GPI polypeptides are provided. In other embodiments, the invention provides (a) a plurality of domain 1 $\beta_2$GPI polypeptide(s); (b) a polypeptide comprising a domain 1 $\beta_2$GPI polypeptide and one or more other domains of $\beta_2$GPI. Examples of such embodiments include, are not limited to, a domain 1 $\beta_2$GPI polypeptide(s) conjugated with (a) domain 2; (b) domain 3; (c) domain 5; (e) domains 3, 4 and 5; (f) domains 4 and 5. These domains are understood by those in the art and are generally as follows (from the N terminus): domain 2, about amino acid 65 to about amino acid 120; domain 3, about amino acid 121 to about amino acid 181; domain 4, about amino acid 182 to about amino acid 244; domain 5, about amino acid 245 to about amino acid 326 (C terminus).

In another embodiment, domain 1 $\beta_2$GPI multiple antigen peptides (Maps) are provided. Maps have a small immunologically inert core having radially branching lysine dendrites, onto which a number of domain 1 $\beta_2$GPI polypeptides can be anchored (i.e., covalently attached). Posnett et al. (1988) *J. Biol. Chem.* 263:1719–1725; Tam (1989) *Meth. Enz.* 168:7–15. The result is a large macromolecule having a high molar ratio of domain 1 $\beta_2$GPI polypeptides to core. Maps are useful, efficient antigens for assays such as ELISA, and may also be useful for multivalent presentation, such as in the toleragenic context. Maps can be made synthetically and can be obtained commercially (Quality Controlled Biochemicals, Inc. Hopkinton, Mass.). In a typical Map system, a core matrix is made up of three levels of lysine and eight amino acids for anchoring domain 1 $\beta_2$GPI polypeptides. The Map may be synthesized by any method known in the art, for example a solid-phase method, for example, R. B. Merrifield (1963) *J. Am. Chem. Soc.* 85:2149.

It is understood that any branched structure, such as cyclodextrin, may be used. The branched structure may be, but need not be, small. In the context of inducing tolerance, the platform should not act as a T cell independent antigen.

It is also understood that certain sequence variations may be introduced into a domain 1 $\beta_2$GPI polypeptide(s) which may preserve or enhance its reactivity. Accordingly, the invention includes modifications to domain 1 $\beta_2$GPI polypeptide(s) which do not significantly affect their properties as well as variants which have enhanced activity. These variant and modified sequences are collectively denoted as "functionally equivalent variants", which may have the same, enhanced, or diminished binding when compared to another domain 1 $\beta_2$GPI polypeptide(s), and are denoted "equivalent" because they maintain the ability to specifically bind to a $\beta_2$GPI-dependent antiphospholipid antibody. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or use of chemical analogs, including alpha-methyl amino acid substitutions, non-protein naturally occurring amino acids (such as canavanine, DL methionine sulfoxide, delta-hydroxylysine hydrochloride, and aminoisobutyric acid), and unnatural amino acids. Amino acid residues which can be conservatively substituted for one another include but are not limited to: glycine/alanine; valine/isoleucine/leucine; asparagine/glutamine; aspartic acid/glutamic acid; serine/threonine; lysine/arginine; and phenylalanine/tyrosine. These polypeptides also include glycosylated and nonglycosylated polypeptides, as well as polypeptides with other post-translational modifications, such as, for example, glycosylation with different sugars, acetylation, and phosphorylation. Preferably, the amino acid substitutions would be conservative, i.e., the substituted amino acid would possess similar chemical properties as that of the original amino acid. Such conservative substitutions are known in the art, and examples have been provided above.

It is understood that certain amino acid variations (such as substitutions) may or may not affect binding of a domain 1 $\beta_2$GPI polypeptide to $\beta_2$GPI-dependent antiphospholipid antibodies in the same manner, or to the same degree. Further, the nature of the substitute amino acid(s) could affect the manner and/or degree of binding. For example, we have found that substituting a glycine residue for an arginine residue at position 43 (amino acid 43 of SEQ ID NO:4) causes loss of ability to bind to antibody in some patient's sera, while others are unchanged (and still others have changed (i.e., intermediate) ability to bind. As another example, substitution of a lysine or threonine for the methionine at position 42 does not appear to affect binding (in the patients we have tested); however, if a valine is substituted for methionine at position 42 binding appears to be abolished in all patients.

In addition to the twenty naturally-occurring amino acids and their homoanalogs and noranalogs, several other classes of alpha amino acids can be employed in the present invention. Examples of these other classes include d-amino acids, NA-alkyl amino acids, alpha-alkyl amino acids, cyclic amino acids, chimeric amino acids, and miscellaneous amino acids. These non-natural amino acids have been widely used to modify bioactive polypeptides to enhance resistance to proteolytic degradation and/or to impart conformational constraints to improve biological activity. Hruby et al. (1990) *Biochem. J.* 268:249–262; Hruby et al. (1995) *Methods in Mol. Biol.* 35:201–240.

The most common $N^{a}$-alkyl amino acids are the $N^{a}$-methyl amino acids, such as $N^{a}$-methyl cysteine (nC), $N^{a}$-methyl glycine (nG), $N^{a}$-methyl leucine (nL), $N^{a}$-methyl lysine (nK), and N-methyl valine (nV). Examples of alpha-alkyl amino acids include alpha-methyl alanine (mA), alpha-aminoisobutyric acid (aiB), alpha-methyl proline (mP), alpha-methyl leucine (mL), alpha-methyl valine (mV), alpha-methyl-alpha-aminobutyric acid (tv), diethylglycine (deG), diphenylglycine (dpG), and dicyclohexyl glycine (dcG). Balaram (1992) *Pure & Appl. Chem.* 64:1061–1066; Toniolo et al. (1993) *Biopolymers* 33:1061–1072; Hinds et al. (1991) *Med. Chem.* 34:1777–1789.

Examples of cyclic amino acids include I-amino-1-cyclopropane carboxylic acid (cG), 1-amino-1-cyclopentane carboxylic acid (Ac5c), 1-amino-1-cyclohexane carboxylic acid (Ac6c), aminoindane carboxylic acid (ind), tetrahydroisoquinoline carboxylic acid (Tic), and pipecolinic acid (Pip). C. Toniolo (1990) *Int'l. J. Peptide Protein Res.* 35:287–300; Burgess et al. (1995) *J. Am. Chem. Soc.* 117:3808–3819. Examples of chimeric amino acids include penicillamine (Pe), combinations of cysteine with valine, 4R- and 4S-mercaptoprolines (Mpt), combinations of homocysteine and proline and 4R- and 4S-hydroxyprolines (hyP) and a combination of homoserine and proline. Examples of miscellaneous alpha amino acids include basic amino acid analogs such as omithine (Or), $N^{\epsilon}$-methyl lysine (mK), 4-pyridyl alanine (pyA), 4-piperidino alanine (piA), and 4-aminophenylalanine; acidic amino acid analogs such as citrulline (Cit), and 3-hydroxyvaline; aromatic amino acid analogs such as 1-naphthylalanine (1-Nal), 2-naphthylalanine (2-Nal), phenylglycine (pG), 3,3-diphenylalanine (dpA), 3-(2-thienyl)alanine (Thi), and halophenylalanines (e.g., 2-fluorophenylalanine and 4-chlorophenylalanine); hydrophobic amino acid analogs such as t-butylglycine (i.e., tertiary leucine (tL)), 2-aminobutyric acid (Abu), cyclohexylalanine (Cy), 4-tetrahydropyranyl alanine (tpA), 3,3-dicyclohexyl alanine (dcA), and 3,4-dehydroproline.

In addition to alpha-amino acids, others such as beta amino acids can also be used in the present invention. Examples of these other amino acids include 2-aminobenzoic acid (Abz), β-aminopropanoic acid (P-Apr), γ-aminobutyric acid (γ-Abu), and 6-aminohexanoic acid (ϵ-Ahx). Carboxylic acids such as 4-chlorobutyric acid (By) and 3-chloropropionic acid (Pp) have also been used as the first residue on the N-terminal in the synthesis of cyclic thioether peptides.

Other methods of modification including using coupling techniques known in the art, including, but not limited to, enzymatic means, oxidative substitution and chelation. Modification can be used, for example, for attachment of labels for immunoassay, such as the attachment of radioactive moieties for radioimmunoassay. Modified domain 1 $\beta_2$GPI polypeptide(s) are made using established procedures in the art and can be screened using standard assays known in the art, some of which are described herein and in the examples.

The invention also encompasses fusion proteins comprising one or more ($\beta_2$GPI domain 1 polypeptides. For purposes of this invention, a $\beta_2$GPI domain 1 fusion protein contains one or more $\beta_2$GPI polypeptides and another amino acid sequence to which it is not attached in the native molecule, for example, a heterologous sequence or a homologous sequence from another region, such as another domain of $\beta_2$GPI. Useful heterologous sequences include, but are not limited to, sequences that provide for secretion from a host cell, enhance immunological reactivity, or facilitate the coupling of the polypeptide to an immunoassay support or a carrier. For instance, a $\beta_2$GPI polypeptide can be fused with a heterologous sequence which facilitates purification. Examples of such sequences are known in the art and include those encoding epitopes such as Myc, HA (derived from influenza virus hemagglutinin), His-6, or FLAG. Other heterologous sequences that facilitate purification are derived from proteins such as glutathione S-transferase (GST), maltose-binding protein (MBP), or the Fc portion of immunoglobulin.

A domain 1 $\beta_2$GPI polypeptide may or may not contain a T cell epitope. For detection purposes, a domain 1 $\beta_2$GPI polypeptide may or may not contain a T cell epitope(s), since the primary use of the polypeptide in this context is for detection of $\beta_2$GPI-dependent antiphospholipid antibody, which is independent of the presence of T cell epitopes. In the toleragen context, however, a domain 1 $\beta_2$GPI polypeptide lacks a (any) detectable T cell epitope(s) with respect to an individual who has $\beta_2$GPI-dependent antiphospholipid antibodies. Thus, in some embodiments, a domain 1 $\beta_2$GPI polypeptide does not contain (i.e., lacks) a T cell epitope (and, accordingly, a polypeptide comprising a domain 1 $\beta_2$GPI polypeptide does not contain a T cell epitope).

Methods for detecting the presence of a T cell epitope are well known in the art. For example, various assays which detect T cell proliferation (such as thymidine incorporation) may be used. The presence of T cell epitopes can also be determined by measuring secretion of T cell-derived lymphokines by methods well known in the art. Polypeptides that fail to induce statistical significant incorporation of thymidine above background (i.e., generally p less than 0.05 using standard statistical methods) are generally considered to lack T cell epitopes, although it will be appreciated that the quantitative amount of thymidine incorporation may vary, depending on the polypeptide being tested. Generally, a stimulation index below about 2–3, more preferably less than about 1, indicates lack of T cell epitopes. Location and content of T cell epitopes are determined empirically.

In the toleragen context, a domain 1 $\beta_2$GPI polypeptide preferably binds specifically to a $\beta_2$GPI-dependent antiphospholipid antibody on the surface a B cell (i.e., binds to a surface antibody on a B cell, wherein the antibody is able to specifically bind a $\beta_2$GPI-dependent antiphospholipid epitope). This binding, especially in conjunction with cross linking, is thought to trigger B cell anergy. It is understood that, because by definition a domain 1 $\beta_2$GPI polypeptide is able to specifically bind a $\beta_2$GPI-dependent antiphospholipid antibody, it would be expected that any domain 1 $\beta_2$GPI polypeptide would likewise be capable of binding to a surface $\beta_2$GPI-dependent antiphospholipid antibody on a B cell.

As discussed below (and above in discussing polymeric forms), preferably, in the toleragen context, a domain 1 $\beta_2$GPI polypeptide is presented in a multi-valent form, whether via a polymeric form and/or conjugated to an appropriate valency platform molecule.

Preparation of Polypeptides of this Invention

The polypeptides of this invention can be made by procedures known in the art. The polypeptides can be produced by recombinant methods (i.e., single or fusion polypeptides) or by chemical synthesis. Polypeptides, especially shorter polypeptides up to about 50 amino acids, are conveniently made by chemical synthesis. Methods of chemical synthesis are known in the art and are commercially available. For example, a polypeptide could be produced by an automated polypeptide synthesizer employing the solid phase method. Polypeptides can also be made by chemical synthesis using techniques known in the art.

Polypeptides can also be made by expression systems, using recombinant methods. The availability of polynucleotides encoding polypeptides permits the construction of expression vectors encoding intact (i.e., native) polypeptide, functionally equivalent fragments thereof, or recombinant forms. A polynucleotide encoding the desired polypeptide, whether in fused or mature form, and whether or not containing a signal sequence to permit secretion, may be ligated into expression vectors suitable for any convenient host. Both eukaryotic and prokaryotic host systems can be used. The polypeptide is then isolated from lysed cells or from the culture medium and purified to the extent needed for its intended use. Purification or isolation of the polypeptides expressed in host systems can be accomplished by any method known in the art. For example, cDNA encoding a polypeptide intact or a fragment thereof can be operatively linked to a suitable promoter, inserted into an expression vector, and transfected into a suitable host cell. The host cell is then cultured under conditions that allow transcription and translation to occur, and the desired polypeptide is recovered. Other controlling transcription or translation segments, such as signal sequences that direct the polypeptide to a specific cell compartment (i.e., for secretion), can also be used. Examples of prokaryotic host cells are known in the art and include, for example, *E. coli* and *B. subtilis*. Examples of eukaryotic host cells are known in the art and include yeast, avian, insect, plant, and animal cells such as COS7, HeLa, CHO and other mammalian cells. Yeast systems include *Saccharomyces cerevisiae, Schizosaccharomyces pombe*, and *Pichia pastoris.*

For example, to express a $\beta_2$GPI domain 1 polypeptide in *Pichia pastoris* (using, for instance, strains SMD 1168 and SMD1168H), a full-length cDNA encoding $\beta_2$GPI is used as a PCR template to create domain 1 gene fragments with a reconstituted Kex2 signal peptide cleavage site at the amino terminus. The fragments are cloned into the expression vector pPICZalpha (Invitrogen Corp.), which is linearized with the restriction enzymes Xho I and Sal I. The constructed genes replace the native domain 1 signal peptide with the yeast alpha-factor signal peptide, and terminate at selected amino acids at the carboxy terminus.

When using an expression system to produce $\beta_2$GPI polypeptides, it is often preferable to construct a fusion protein that facilitates purification. Examples of components for these fusion proteins include, but are not limited to, myc, HA, FLAG, His-6, glutathione S-transferase, maltose binding protein or the Fc portion of immunoglobulin. These methods are known in the art. See, for example, Redd et al. (1997) *J. Biol. Chem.* 272:11193–11197. Techniques known in the art may be employed to remove unwanted amino acids from fusions, such as His-6. For example, carboxypeptidase A may be used to eliminate carboxyterminal amino acid Carboxypeptidase A stops at amino acids proline or arginine. For convenience of purification, solid phase carboxypeptidase A (Sigma) may be used.

Preferably, especially if used for diagnostic purposes, the polypeptides are at least partially purified or isolated from other cellular constituents. Preferably, the polypeptides are at least 50% pure. In this context, purity is calculated as a weight percent of the total protein content of the preparation. More preferably, the proteins are 50–75% pure. More highly purified polypeptides may also be obtained and are encompassed by the present invention. For clinical use, the polypeptides are preferably highly purified, at least about 80% pure, and free of pyrogens and other contaminants. Methods of protein purification are known in the art and are not described in detail herein.

In some systems, especially some recombinant systems, for embodiments which contain an extra (fifth) cysteine, or a cysteine which is to be reduced (in order to, for example, conjugate the polypeptide to a platform molecule), the initial product may comprise low molecular weight mixed disulfides, in which the fifth (or extra, reactive) cysteine is covalently linked to other, relatively low molecular weight moiety or moieties. In these instances, selective reduction of the extra cysteine is desired (while maintaining other disulfide bonds). Such selective reduction may be accomplished by using a solid phase reductant agent, such as DTT, on a solid support, such as acrylamide (such as REDUCTACRYL by CalBiochem, San Diego).

Further, in systems which are designed and/or used to produce a domain 1 $\beta_2$GPI polypeptide with an extra cysteine (i.e., the cysteine is to serve as a reactive group), it may be desirable to make the polypeptide such that an additional amino acid or acids follow the extra cysteine in the sequence, to protect the cysteine during synthesis and/or production.

Preferably, especially if the polypeptide is to be conjugated to a platform (discussed below), chemical synthesis is used. Chemical synthesis permits modification of the N or C terminus, which facilitates conjugation to a platform molecule.

When producing a domain 1 $\beta_2$GPI polypeptide, such as those which have an additional cysteine in addition to the four cysteines of domain 1 (which form disulfide linkages), conditions should be selected to promote correct disulfide bridge formation. As an example, a reduced polypeptide is denatured by dissolving in 6 M guanidinium hydrochloride (GnHCl) to yield a concentration of 0.5 mg/ml. Folding is achieved by dialysis at room temperature against the following renaturant buffer: 0.1 M GnHCl, 0.5 mM Tris-HCl and 1 mM EDTA, pH 8.5. To assist correct disulfide bridges formation, a mixture of 0.3 mM and 3 mM of respectively oxidized and reduced glutathione is added. The reaction mixture is monitored by HPLC and the different products analyzed by mass spectrometry. In our experiments, after 5 hours of cyclization, analytical HPLC showed approximately 65% conversion of which 50% had the correct mass (Mw=7260) and ~15% existing as a glutathione adduct (Mw=7567). The folded protein lacking glutathionine is then purified by reverse phase HPLC.

Conjugates of Domain 1 $\beta_2$GPI Polypeptide(s)

The invention also provides conjugates of domain 1 $\beta_2$GPI polypeptide(s). In some embodiments, domain 1 $\beta_2$GPI polypeptide(s) can be conjugated with carrier or label. A number of techniques for obtaining such linkage are known in the art and need not be described in detail herein. Any carrier can be used which is safe and does not itself induce the production of antibodies harmful to the host. Suitable carriers are typically large, slowly metabolized macromolecules such as proteins; polysaccharides, such as latex functionalized sepharose, agarose, cellulose, cellulose beads and the like; polymeric amino acids, such as polyglutamic acid, polylysine, and the like; amino acid copolymers; and inactive virus particles or attenuated bacteria, such as Salmonella. Especially useful protein substrates are serum albumins, keyhole limpet hemacyanin, immunoglobulin molecules, thyroglobulin, ovalbumin, tetanus toxoid, and other proteins well known to those of skill in the art.

Labels are known in the art and need not be described in detail herein. There are many different labels and methods of labeling known to those of ordinary skill in the art. Examples of the types of labels which can be used in the present invention include enzymes, radioisotopes, fluorescent compounds, colloidal metals, chemiluminescent compounds, and bioluminescent compounds. Those of ordinary skill in the art will know of other suitable labels, or will be able to ascertain such, using routine experimentation. Furthermore, the binding of these labels to polypeptides of the invention can be done using standard techniques common to those of ordinary skill in the art.

Domain 1 $\beta_2$GPI polypeptide(s) (most preferably lacking a T cell epitope) may be conjugated to a non-immunogenic valency platform molecule (also termed "platform"), which enhances presentation of the domain 1 $\beta_2$GPI polypeptide(s). U.S. Pat. Nos. 5,162,515; 5,276,013; 5,552,391. A platform may be proteinaceous or non-proteinaceous (i.e., organic). Examples of proteinaceous platforms include, but are not limited to, albumin, gammaglobulin, immunoglobulin (IgG) and ovalbumin. Borel et al. (1990) *Immunol. Methods* 126:159–168; Dumas et al. (1995) *Arch. Dematol. Res.* 287:123–128; Borel et al. (1995) *Int. Arch. Allergy Immunol.* 107:264–267; Borel et al. (1996) *Ann. N.Y. Acad. Sci.* 778:80–87. Most preferably, a platform is multi-valent (i.e., contains more than one binding, or linking, site). Preferably, a multi-valent platform contains at least two, more preferably at least 3, more preferably at least 5, more preferably at least 7, more preferably at least 10, even more preferably at least 12, even more preferably at least 15 linking sites. It is understood, however, that in the context of inducing tolerance (i.e., when a platform is used in conjunction with an appropriate domain 1 $\beta_2$GPI polypeptide to effect immunotolerance), depending on the nature of the domain 1 $\beta_2$GPI polypeptide(s) employed and the particular condition, any of a number of linking sites may be sufficient. It is also understood that a platform is not a T cell independent antigen.

Preferred valency platform molecules are biologically stabilized, i.e., they exhibit an in vivo excretion half-life often of hours to days to months to confer therapeutic efficacy, and are preferably composed of a synthetic single chain of defined composition. They generally have a molecular weight in the range of about 200 to about 200,000, preferably about 200 to about 50,000 (or less, such as 30,000). Examples of valency platform molecules within the present invention are polymers (or are comprised of polymers) such as polyethylene glycol (PEG), poly-D-lysine, polyvinyl alcohol, polyvinylpyrrollidone, D-glutamic acid and D-lysine (in a ratio of 3:2). Preferred polymers are based on polyethylene glycols (PEGs) having a molecular weight of about 200 to about 8,000. Other molecules that may be conjugated to domain 1 $\beta_2$GPI polypeptide(s) are albumin and IgG.

Other preferred valency platform molecules suitable for use within the present invention are the chemically-defined, non-polymeric valency platform molecules such as those disclosed in co-owned U.S. Pat. No. 5,552,391. In contrast to previously described, more traditional platforms, these platforms have the advantage of having a homogeneous (i.e., uniform) molecular weight (as opposed to polydisperse molecular weight), and are thus "chemically defined". Accordingly, it is understood that a population of conjugates using these platforms comprise a platform of homogeneous molecular weight or are substantially monodisperse (i.e., have a narrow molecular weight distribution). A measure of the breadth of distribution of molecular weight of a sample (such as a composition and/or population of platform molecules) of a platform molecule is the polydispersity of the sample. Polydispersity is used as a measure of the molecular weight homogeneity or nonhomogeneity of a polymer sample. Polydispersity is calculated by dividing the weight average molecular weight (Mw) by the number average molecular weight (Mn). The value of Mw/Mn is unity for a perfectly monodisperse polymer. Polydispersity (Mw/Mn) is measured by methods available in the art, such as gel permeation chromatography. The polydispersity (Mw/Mn) of a sample of platform molecules is preferably less than 2, more preferably, less than 1.5, or less than 1.2, less than 1.07, less than 1.02, or, e.g., about 1.05 to 1.5 or about 1.05 to 1.2. Typical polymers generally have a polydispersity of 2–5, or in some cases, 20 or more. Advantages of the low polydispersity property of the valency platform molecules include improved biocompatibility and bioavailability since the molecules are substantially homogeneous in size, and variations in biological activity due to wide variations in molecular weight are minimized. The low polydispersity molecules thus are pharmaceutically optimally formulated and easy to analyze. Further there is controlled valency of the population of molecules in the sample.

Examples of preferred homogeneous chemically-defined valency platform molecules suitable for use within the present invention include derivatized 2,2'-ethylenedioxydiethylamine (EDDA) and triethylene glycol (TEG). Other examples of preferred homogeneous, chemically defined platforms are described below as well as in the art. In other embodiments, a domain 1 $\beta_2$GPI polypeptide(s) is conjugated to albumin, IgG, and/or PEG.

Additional suitable valency platform molecules include, but are not limited to, tetraaminobenzene, heptaaminobetacyclodextrin, tetraaminopentaerythritol, 1,4,8,11-tetraazacyclotetradecane (Cyclam) and 1,4,7,10-tetraazacyclododecane (Cyclen).

In general, these platforms are made by standard chemical synthesis techniques. PEG must be derivatized and made multivalent, which is accomplished using standard techniques. Some substances suitable for conjugate synthesis, such as PEG, albumin, and IgG are available commercially.

Conjugation of a domain 1 $\beta_2$GPI polypeptide(s) to a valency platform molecule may be effected in any number of ways, typically involving one or more crosslinking agents and functional groups on the polypeptide and valency platform molecule. Platforms and domain 1 $\beta_2$GPI polypeptide(s) must have appropriate linking groups. Linking groups are added to platforms using standard synthetic chemistry techniques. Linking groups may be added to a domain 1 $\beta_2$GPI polypeptide(s) using either standard solid phase synthetic techniques or recombinant techniques. Recombinant approaches may require post-translational modification in order to attach a linker, and such methods are known in the art.

As an example, polypeptides contain amino acid side chain moieties containing functional groups such as amino, carboxyl, or sulfhydryl groups that serve as sites for coupling the polypeptide to the platform. Residues that have such functional groups may be added to the polypeptide if the polypeptide does not already contain these groups. Such residues may be incorporated by solid phase synthesis techniques or recombinant techniques, both of which are well known in the peptide synthesis arts. When the polypeptide has a carbohydrate side chain(s), functional amino, sulfhydryl and/or aldehyde groups may be incorporated therein by conventional chemistry. For instance, primary amino groups may be incorporated by reaction with ethylenediamine in the presence of sodium cyanoborohydride, sulfhydryls may be introduced by reaction of cysteamine dihydrochloride followed by reduction with a standard disulfide reducing agent, while aldehyde groups may be generated following periodate oxidation. In a similar fashion, the valency platform molecule may also be derivatized to contain functional groups if it does not already possess appropriate functional groups.

Polypeptides can also be site specifically modified at their C-termini by a process called reverse proteolysis. Essentially, reverse proteolysis uses proteolytic enzymes to catalyze amide bond fomation by using conditions which drive the reaction in that direction. Polypeptides have been modified using reverse proteolysis to attach hydrazide containing linkers (Rose, K. et al., Bioconjugate Chemistry 1991, 2, 154–159) or aminooxy containing linkers (Rose, K. et al., Bioconjugate Chemistry 1996, 7, 552–556) at their C-termini via amide bonds. Such modified polypeptides can be reacted to form hydrazone or oxime linkages to other molecules of interest which contain aldehyde or ketone groups. In addition other linkers, such as sulfhydryl containing linkers could concieveably be attached via reverse proteolysis.

Hydrophilic linkers of variable lengths are useful for connecting polypeptides (or other bioactive molecules) to valency platform molecules. Suitable linkers include linear oligomers or polymers of ethylene glycol. Such linkers include linkers with the formula $R^1S(CH_2CH_2O)_n CH_2CH_2O(CH_2)_mCO_2R^2$ wherein n=0–200, m=1 or 2, $R^1$=H or a protecting group such as trityl, $R^2$=H or alkyl or aryl, e.g., 4-nitrophenyl ester. These linkers are useful in connecting a molecule containing a thiol reactive group such as haloacyl, maleiamide, etc., via a thioether to a second molecule which contains an amino group via an amide bond. These linkers are flexible with regard to the order of attachment, i.e., the thioether can be formed first or last.

As discussed above, domain 1 $\beta_2$GPI polypeptide(s) may be conjugated to any of a number of suitable platforms by any of a number of ways. In a preferred embodiment, the tetra-bromoacetyl platform PIZ/IDA/TEG-$\beta_2$GPI domain 1 is used. Other preferred embodiments aare in the Examples.

Derivatives of the PIZ/IDA/TEG (PITG) platform can be prepared as shown below.

Examples of Compatible Cross-linking Groups on PITG Platform

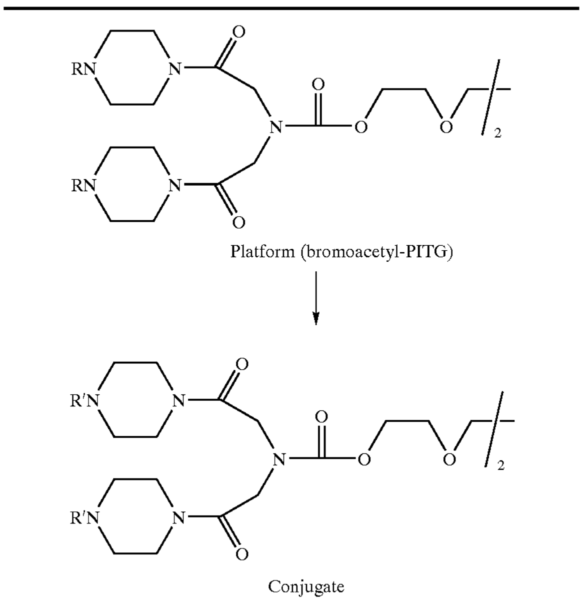

| Platform | Domain 1 polypeptide | Conjugate |
| --- | --- | --- |
| R = $XCH_2CO$ | D1-SH | R' = D1-$SCH_2CO$ |

By way of example of a conjugate embodiment, a domain 1 $\beta_2$GPI polypeptide(s) is prepared with a thiol linker at the N terminus by solid phase peptide synthesis or by recombinant methods. The linker can be cysteine or an SH containing moiety. The modified polypeptide may then be alkylated by a suitably derivatized platform (such as bromoacetyl or iodoacetyl).

In some embodiments, a domain 1 $\beta_2$GPI polypeptide is conjugated via a sulfhydryl group (thiol, or SH), for example, on a cysteine, resulting in a thioether linkage in the conjugate. In some embodiments, this reactive cysteine is provided by including the fifth cysteine of $\beta_2$GPI (Example 5).

In some embodiments, conjugates are formed via an oxime linkage. An oxime linkage may be formed by reacting, for example, a carbonyl group such as an aldehyde or ketone on a domain 1 $\beta_2$GPI polypeptide with a platform that contains an aminooxy reactive group, such as aminooxy, aminooxyacetyl, and aminooxyalkyl. The aminooxy groups can be on triethylene glycol or hexyl chains; however any chain comprising carbon, oxygen, nitrogen or sulfur atoms would suffice as long as is terminates in $—ONH_2$.

To make these conjugates, a domain $\beta_2$GPI polypeptide is selectively modified to generate an aldehyde or ketone moiety at a specific position on the polypeptide, such as the N terminus. Second, the polypeptide is reacted with a multivalent platform which contains aminooxy groups to form oxime linkages between the platform and the polypeptide.

The N-terminus of the domain 1 $\beta_2$GPI polypeptide can be converted to an aldehyde or a ketone by a transamination reaction, which is known in the art. Generally, the transamination reaction converts the N-terminal carbon-nitrogen single bond to a carbon oxygen double bond. A glycine at the N-terminus reacts to form a glyoxyl group, an aldehyde. Most other amino acids react to form a ketone by virtue of the amino acid side chain.

Another way to generate an glyoxyl group at the N-terminus is to oxidize an N-terminal serine or threonine with sodium periodate. This oxidation cleaves the carbon-carbon bond between the hydroxyl and amino groups of the N-terminal serine or threonine providing a glyoxyl group.

In some embodiments, multivalent platforms containing aminooxylacetyl (AOA) reactive groups may be produced to connect the selectively modified polypeptides to the platforms. Aminooxylacetyl (AOA) groups can be conveniently attached to multivalent platforms containing amine groups by acylation with a N-protected aminooxyacetyl group followed by protecting group removal. However, reaction of glyoxyl polypeptides with AOA-derivitized platforms proceeds slowly, taking several days to form oxime linkages between the polypeptide and the platform. Example 5 describes synthesis of conjugate compound 44, which entailed attaching a transaminated $\beta_2$GPI domain 1 polypeptide to a aminoacetylated tetrameric platform. The invention includes this conjugate.

In other embodiments, platforms containing aminooxy alkyl reactive groups may be used. Aminooxyalkyl groups are defined as an aminooxy group on a first carbon, wherein the first carbon is preferably not directly attached to an electron withdrawing group such as a second carbon which is part of a carbonyl group. We have observed that aminooxy alkyl groups react more readily with ketones and aldehydes to form oximes than aminooxyacetyl groups. The aminooxyacetyl group appears to be generally less reactive than other aminooxy groups (aminooxyalkyl groups) which are not adjacent to a carbonyl. The carbonyl of the aminooxyacetyl group is thought to cause a lowering of reactivity due to electron withdrawing effects. More information regarding these platforms and conjugates is found in the Examples and in commonly owned U.S. patent application Ser. No. 09/724,822. Conjugate compound 45, described in Example 5, was synthesized by attaching a transaminated $\beta_2$GPI domain 1 polypeptide to an aminooxy tetrameric platform. The invention includes this conjugate, as well as those $\beta_2$GPI domain 1 polypeptide oxime conjugates which arise from AO-based synthesis.

Polynucleotides of the Invention

The invention also provides polynucleotides (including isolated naturally-occuring and non-naturally occurring polynucleotides) encoding a domain 1 $\beta_2$GPI polypeptide(s). Such polynucleotides are useful for, for example, production of domain 1 $\beta_2$GPI polypeptide(s). Production of domain 1 $\beta_2$GPI polypeptide(s) may be effected using standard techniques the art such as recombinant cloning/expression vectors and protein purification methods. If production is to occur in vivo, an appropriate expression system is used, such as those listed below. With knowledge of the amino acid sequence of a domain 1 $\beta_2$GPI polypeptide(s) (which is obtained using standard protein sequencing techniques), a polynucleotide can be designed which encodes for that particular amino acid sequence. Polynucleotides may be synthesized or obtained (when appropriate) from genomic or cDNA sequences.

The invention also includes cloning vectors and expression vectors containing any of the polynucleotides described above. These vectors are well known in the art (e.g., those for use in vitro, bacterial, mammalian, yeast and insect expression systems) and need not be described herein. See, for example, Gacesa and Ramji, *Vectors*, John Wiley & Sons (1994).

The invention also includes host cells that contain (i.e., are transformed with, or comprise) any of the polynucleotides and/or vectors described herein. Both prokaryotic and eukaryotic host cells may be used. Prokaryotic hosts include bacterial cells, for example *E. coli, B. subtilis*, and mycobacteria. Among eukaryotic hosts are fungi (including yeast), insect, avian, plant and mammalian cells. Host systems are known in the art and need not be described in detail herein. The host cells of this invention can be used, inter alia, as repositories of the polynucleotides described above and/or vehicles for production of domain 1 $\beta_2$GPI polypeptide(s) polynucleotides and/or polypeptides. They may also be used as vehicles for in vivo delivery of domain 1 $\beta_2$GPI polypeptide(s).

Domain 1 $\beta_2$GPI Mimetics of the Invention

The invention also provides domain 152GPI mimetics (or analogs), which specifically bind to a $\beta_2$GPI-dependent antiphospholipid antibody to which a domain 1 $\beta_2$GPI polypeptide (including entire domain 1) specifically binds (i.e., the mimetic shares an epitope specific for a $\beta_2$GPI-dependent antiphospholipid antibody with a domain 1 $\beta_2$GPI polypeptide(s)). Put another way, the mimetic mimics an epitope in domain 1 (i.e., competitively binds to $\beta_2$GPI-dependent antiphospholipid antibody in the presence of a domain 1 $\beta_2$GPI polypeptide(s)). The mimetic(s) may be any of a number of chemical substances, as described above. Depending on their chemical nature, mimetics of the invention may be produced using standard techniques in the chemical and biochemical (including biotechnology) arts. These mimetics may be used in detection and/or as toleragens. When used as a toleragen, a mimetic(s) lacks a detectable T cell epitope.

Mimetics of the invention may be identified using conventional techniques. For example, candidate molecules may be screened to determine whether they (a) bind specifically to $\beta_2$GPI-dependent antiphospholipid antibodies and/or (b) lack T cell epitopes (i.e., fail to elicit a T cell response or T cell-associated activity). Determination of either or both of these activities have been described in the art and herein. Screening of candidate polypeptide mimetics may be accomplished using phage display methods (including micropanning) known in the art (see Example 3). The following is a summary description of some of these techniques.

Various assays have been developed with varying degrees of stringency in order to identify the best epitopes from an epitope library screen. The assays are listed here in order of increasing stringency: Biopanning<Micropanning<Phage-Capture ELISA<Phage ELISA=Colony Blot=Peptide ELISA.

"Biopanning" describes the technique wherein affinity-purified $\beta_2$GPI-dependent antiphospholipid antibody and phage bearing random peptide inserts are allowed to mix, following which antibody-specific recovery captures the bound phage. The phage confer tetracycline resistance to *E. Coli* that are propagated in a tetracycline-containing medium and then isolated. Multiple rounds of biopanning enrich the number of immunospecific phage in a sample. Phage are always recovered at the end of three to five rounds of selection but may represent only sequences that are nonspecifically bound at low affinities for the selecting antibodies. A method for further evaluating these phage (micropanning) is required.

Micropanning provides an estimation of the relative strength of binding of the phage to the $\beta_2$GPI-dependent antiphospholipid antibody. Micropanning is carried out following three or more rounds of biopanning and uses the same antibody as employed in the biopanning method. The method consists of dilution of the phage from the last round of biopanning and analyzing fifty or more of these clones by micropanning. Micropanning is accomplished by growing each clone to a similar density and then incubating dilute phage at an optimal single concentration in microtitration wells previously coated with a constant amount of antibody. The optimal single concentration of phage is that concentration most likely to reveal the widest range of micropanning scores (from 0 to 4+) and, thus, permit the greatest discrimination among the clones being tested. It is based on the micropanning behavior of six randomly selected clones where the score is determined at each of several concentrations of phage obtained by serial dilution. Following the incubation with antibody, the unbound phage are washed away and the amount of bound phage is used as an indication of the affinity of the phage insert for the antibody. The amount of bound phage is determined by elution with mild acid followed by neutralization and infection of *E. coli*. The number of infected E. coli are then quantitated by plating the microorganisms on agar plates containing tetracycline and then determining colony densities achieved by each clone.

The phage-capture ELISA test was developed to provide an intermediate level assay to bridge the gap between the relatively low stringency of the micropanning assay and the high stringency of the phage- or peptide-ELISA assays. Preliminary studies show that some antibody preparations give too many positive clones by micropanning but none by phage-ELISA or peptide-ELISA. The limitation of the phage-ELISA described below is that only five copies of p-III are located on each phage and even with a large number of phage coated on a well, few copies of the insert are represented and detection requires that the antibody have a very high affinity for the insert. With the phage-capture ELISA, the signal is amplified many times which facilitates the detection of lower affinity, stable interactions between the antibody and the insert.

The phage-capture ELISA consists of the following steps. Microtitration wells are coated with $\beta_2$GPI-dependent antiphospholipid antibody and phage clones are added as in the micropanning assay. Unbound phage are washed away and the amount of bound phage is quantitated using an enzyme-conjugated goat antiserum which binds the phage. Phage screened using phage-capture ELISA react with many aPL antibodies and provide a strong signal in subsequent ELISA assays. This intermediate level of sensitivity allows for greater efficiency in the peptide synthesis effort since few micropanning-positive phage are phage-capture ELISA positive. As a result, peptides synthesized from positive phage-capture ELISA phage are generally immunoreactive.

Phage-ELISA method of selection requires very tight binding of the insert to the screening antibody. Phage are directly coated onto wells of a microtitration plate and incubated with the screening antibody. Following washes to remove unbound antibody, an anti-human IgG alkaline phosphatase conjugate is added to bind any GPI-dependent antiphospholipid antibodies bound to the phage. $\beta_2$GPI-dependent antiphospholipid antibodies are then detected by adding a colorimetric substrate to the well which will react with alkaline phosphatase according to methods well known in the art.

Colony blot assay allows large-scale colony screening of *E. coli* infected by biopanned phage. This procedure is an alternative to phage-ELISA for identifying immunoreactive clones and exhibits a comparable level of sensitivity without requiring culturing of individual phage clones prior to testing. In this assay, E. coli infected with phage from a round of biopanning are spread on a large diameter nitrocellulose (NC) membrane and cultured overnight on the surface of an agar plate containing tetracycline. Barbas et al. (1991) *Proc. Natl. Acad. Sci. USA* 88:7978–7982. Each colony results from infection by phage containing identical sequences. Several replicate transfer blots on NC are made using this NC "master" and are allowed to grow on the surface of an agar plate. Following the chemical and enzymatic disruption of phage-infected colonies on the blots, the phage may be probed by the techniques commonly used in Western blotting, i.e., staining or immunoblotting. Blots that have been blocked may be incubated with the screening aPL antibody. Following washes to remove unbound antibody, an anti-human IgG horseradish peroxidase conjugate is added to bind to any $\beta_2$GPI-dependent antiphospholipid-antibody that is bound to phage. The addition of a calorimetric substrate allows one to localize the discrete colonies in the master plate which represent immunospecific phage that may be cloned for further study.

Following DNA sequencing to determine the peptide insert sequences of the best-reacting phage in the assays described above, the corresponding peptides are made using standard Fmoc peptide chemistry as is well known in the art. For the peptide-ELISA assay, the peptides can be made, for example, as branched tetravalent molecules, i.e., each molecule has four copies of the insert. Such a molecule can coat the well of a microtitration plate and still have epitopes exposed to the solution to allow binding by an antibody. The tetravalent peptides are synthesized by incorporating lysines as branch points at the first two couplings analogous to the methods used for Maps, discussed above. Posnett et al. (1988). A spacer consisting of glycine-serine-glycine-serine is added on each arm after the lysines and then the insert, including the framework amino acids found in the phage, proline-glycine at the carboxyl terminus and alanine-glycine-proline at the amino terminus. All amino acids in this synthesis are added one at a time using standard Fmoc methods.

These peptides are then assayed by ELISA which is carried out by coating the peptides on microtitration wells and then assaying their reactivity with aPL antibody in a standard ELISA format. In practice, the peptides usually bind very strongly to the original screening antibody and show some cross-reactivity with other $\beta_2$GPI-dependent antiphospholipid antibodies. Controls of non-$\beta_2$GPI-dependent antiphospholipid antibodies are included to eliminate nonspecific binding peptides.

A peptide competitive binding ELISA determines whether two peptides bind the same population of antibodies in a given individual's serum and quantitates relative binding affinity to the $\beta_2$GPI-dependent antiphospholipid antibodies. In this assay, various monomeric peptides compete with tetravalent peptides coated on a microtitration plate well. To perform the assay, the peptides to be evaluated are synthesized as monomers, i.e., without the lysine branches employed in the synthesis of the tetravalent peptides, using standard Fmoc chemistry. The monomeric peptides are then purified and dissolved at known concentrations. Wells of a microtitration plate are coated with a tetravalent peptide known to bind to the $\beta_2$GPI-dependent antiphospholipid antibody. Serial dilutions of the monomeric peptides are incubated with a constant dilution of the $\beta_2$GPI-dependent antiphospholipid antibody. The dilution of the $\beta_2$GPI-dependent antiphospholipid antibody was previously determined by titering the antibody against the tetravalent peptide and selecting a dilution on the downslope of the titration curve. After incubating the antibody and monomeric peptides for one hour, the antibody/peptide solutions are added to the microtitration wells and a standard calorimetric ELISA is performed. The concentration of each monomeric peptide that decreases binding of the $\beta_2$GPI-dependent antiphospholipid antibody with the tetravalent peptide is determined by plotting the calorimetric readings obtained for each well. The 50% inhibition point is used as the measure of the relative strength of binding for the monomeric peptides.

A variation of this assay uses microtitration plates coated with $\beta_2$GP-1/cardiolipin instead of tetravalent peptide and tests the ability of monomeric peptides to block the binding of $\beta_2$GPI-dependent antiphospholipid antibody to the epitope(s) on $\beta_2$GPI/CL. In this assay, IgG-depleted human serum at an optimized concentration is used as a source of $\beta_2$GPI. The monomeric peptides at several concentrations are incubated with an optimized concentration of $\beta_2$GPI-dependent antiphospholipid antibody in a manner analogous to the assay which employs tetravalent peptide as a plate substrate. Following the incubation of $\beta_2$GPI-dependent antiphospholipid/peptide in ($\beta_2$GPI/CL) plates, antibody binding and the peptide concentration required for 50% inhibition is determined at half-maximal absorbance as in the tetravalent assay.

An additional variation of this assay tests the ability of monomeric peptides to block the binding of $\beta_2$GPI-dependent antiphospholipid antibody to $\beta_2$GPI coated directly on the wells of Nunc Maxisorp microtitration plates. In this variation, the use of cardiolipin is omitted and instead of fish gelatin, the reagent diluent and blocker used is nonfat milk.

Another variation of this assay tests the ability of multivalent domain 1 $\beta_2$GPI polypeptide conjugates toleragen molecules or domain 1$\beta_2$GPI polypeptide monomers to block the binding in serum or plasma of $\beta_2$GPI-dependent antiphospholipid antibody to $\beta_2$GPI coated directly on the wells of Nunc Maxisorp microtitration plates. No cardiolipin is employed in the assay. Nonfat milk plus the detergent Tween-80 are used in both the blocking and reagent diluent solutions.

The desired epitope for tolerance induction should have as strong an interaction with as many of the $\beta_2$ GPI dependent antiphospholipid antibodies as possible but not contain any unnecessary residues. In order to deduce the minimum constitution of an epitope, mimetics of each peptide are made (i) that lack given residues, for example, the framework residues at the carboxyl and/or amino termini are deleted, or (ii) in which amino acid substitutions have been made which differ from sequences found in the epitope library screen. These amino acid substitutions may be either natural, e.g., isoleucine for leucine, or unnatural, e.g., alpha methyl proline for proline. The effect of these deletions and/or substitutions are then measured via peptide-competition ELISA.

The invention also includes conjugates of a mimetic(s), compositions comprising a mimetic(s), kits comprising a mimetic(s), and polynucleotides encoding any polypeptide mimetic(s). How to make and use these embodiments has been described in previous sections, and the principles and techniques presented likewise apply to mimetics.

Compositions of the Invention

The present invention further provides compositions comprising domain 1 $\beta_2$GPI polypeptides (including all polypeptide embodiments described above, such as fusions, polymeric polypeptides, and conjugates), as well as compositions comprising polynucleotides encoding domain 1 $\beta_2$GPI and compositions comprising mimetic(s). These compositions are especially useful for administration to those individuals who may benefit from induction of tolerance. The compositions are also useful as reagents in detection systems.

Generally, the compositions of the invention for use in inducing tolerance comprise an effective amount of a domain 1 $\beta_2$GPI polypeptide(s) (or mimetic(s)), preferably in a pharmaceutically acceptable excipient, and may be in various formulations. As is well known in the art, a pharmaceutically acceptable excipient is a relatively inert substance that facilitates administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonperenteral drug delivery are set forth in *Remington's Pharmaceutical Sciences* 19th Ed. Mack Publishing (1995).

Generally, these compositions are formulated for administration by injection (e.g., intraperitoneally, intravenously, subcutaneously, intramuscularly, etc.). Accordingly, these compositions are preferably combined with pharmaceutically acceptable vehicles such as saline, Ringer's solution, dextrose solution, and the like. Generally, the conjugate will normally constitute about 0.01% to 10% by weight of the formulation due to practical, empirical considerations such as solubility and osmolarity. The particular dosage regimen, i.e., dose, timing and repetition, will depend on the particular individual and that individual's medical history. Generally, a dose of about 1 $\mu$g to about 100 mg conjugate/kg body weight, preferably about 100 $\mu$g to about 10 mg/kg body weight, will be given weekly. Empirical considerations, such as the half life, generally will contribute to determination of the dosage. Other appropriate dosing schedules may be as frequent as daily or 3 doses per week, or one dose per week, or one dose every two to four weeks, or one dose on a monthly or less frequent schedule depending on the individual or the disease state. Repetitive administrations, normally timed according to B cell turnover rates, may be required to achieve and/or maintain a state of humoral anergy. Such repetitive administrations generally involve treatments of about 1 µg to about 10 mg/kg body weight or higher every 30 to 60 days, or sooner, if an increase in antibody GPL score is detected. Alternatively, sustained continuous release formulations of the compositions may be indicated for some pathologies. Various formulations and devices for achieving sustained release are known in the art.

Other formulations include suitable delivery forms known in the art including, but not limited to, carriers such as liposomes. Mahato et a!. (1997) *Pharm. Res.* 14:853–859. Liposomal preparations include, but are not limited to, cytofectins, multilamellar vesicles and unilamellar vesicles.

In some embodiments, more than one domain 1 $\beta_2$GPI polypeptide(s) (or mimetic(s)) may be present in a composition. Such compositions may contain at least one, at least two, at least three, at least four, at least five different domain 1 $\beta_2$GPI polypeptide(s). Such "cocktails", as they are often denoted in the art, may be particularly useful in treating a broader range of population of individuals. They may also be useful in being more effective than using only one (or fewer than are contained in the cocktail) domain 1 $\beta_2$GPI polypeptide(s).

The compositions may be administered alone or in conjunction with other forms of agents that serve to enhance and/or complement the effectiveness of a domain 1 $\beta_2$GPI polypeptide(s), including, but not limited to, anti-helper T cell treatments. Such treatments usually employ agents that suppress T cells such as steroids or cyclosporin.

Appropriate individuals to receive such compositions may be identified using clinical parameters known in the art, such as determination of GPL scores of $\beta_2$GPI-dependent antiphospholipid antibodies, determination of presence of $\beta_2$GPI-dependent antiphospholipid antibodies particularly associated with disease state(s), and/or symptoms of $\beta_2$GPI-dependent antiphospholipid-associated pathologies. Preferably, the individual is human. With respect to $\beta_2$GPI-dependent antiphospholipid antibody, a GPL score of at least about 10, preferably at least about 20, more preferably at least about 40 may indicate administration of any of these compositions. This score is based on the presently commercially available assay which is a solid phase $\beta_2$GPI-dependent antiphospholipid antibody ELISA (e.g., Inova (San Diego); Theratest (Chicago); APL Diagnostics (Louisville)). Also indicated for administration of these compositions are those individuals who have a family history of any $\beta_2$GPI-dependent antiphospholipid antibody-associated disorder (i.e., disease), or those individuals who are considered having a "normal" GPL score but who have displayed an increasing GPL score over a period of time.

Generally, efficacy of administering any of these compositions is adjudged by measuring any change in the clinical parameters described above, particularly the $\beta_2$GPI-dependent antiphospholipid GPL score. However, measurement of any parameter that is thought or has been shown to be associated with the condition being treated is suitable.

With respect to those compositions which may be used as reagents (such as in detection assays), these compositions generally comprise an amount of a domain 1 $\beta_2$GPI polypeptide(s) (i.e., one or more polypeptide) sufficient to effect detection. These amounts are readily determined empirically. These compositions may further comprise a substance, such as a buffer, to effect detection. These compositions may also optionally be complexed to a detection matrix, such as solid phase (e.g., in an immunoaffinity column).

Kits Comprising $\beta_2$GPI Domain 1 Polypeptide(s)

The invention also provides kits containing (i.e., comprising) one or more domain 1 $\beta_2$GPI polypeptide(s) (or one or more domain 1 $\beta_2$GPI polypeptide(s) mimetic) and, optionally, antibodies to domain 1 $\beta_2$GPI polypeptide(s) as a standard, preferably diagnostic kits for detection of $\beta_2$GPI-dependent antiphospholipid antibody. Diagnostic and monitoring procedures using domain 1 $\beta_2$GPI polypeptide(s) of this invention can be performed by diagnostic laboratories, experimental laboratories, practitioners, or private individuals. Kits embodied by this invention include those that allow someone to conduct an assay for the presence of antibodies to domain 1 $\beta_2$GPI polypeptide(s), such as any of those disclosed herein, thus detecting an/or quantitating those antibodies. The kits embodied by this invention also include kits that allow detection of antibodies to domain 12GPI polypeptide(s) in, for example, ex vivo or in vivo transfected cells. Accordingly, the invention includes a kit containing domain 1 $\beta_2$GPI polypeptide(s) for detection and/or quantification of an anti-domain 1$\beta_2$GPI polypeptide(s) antibody, preferably a $\beta_2$GPI-dependent antiphospholipid antibody, in a biological sample. The kits of this invention are in suitable packaging, and may optionally provide additional components that are useful in the procedure. These optional components include, but are not limited to, buffers, capture reagents, developing reagents, labels, reacting surfaces, means for detection, control samples, instructions, and interpretive information.

Any appropriate means for detecting binding of the antibodies may be employed (and provided in the kits) such as a labeled anti-human antibody, when the presence of human $\beta_2$GPI-dependent antiphospholipid antibodies is tested, wherein the label may be an enzyme, fluorophore, chemiluminescent material radioisotope, coenzyme. Generally, the label used will be an enzyme.

In addition to detecting $\beta_2$GPI-dependent antiphospholipid antibodies, a 2GPI polypeptide(s) (or one or more domain 1$\beta_2$GPI polypeptide(s) mimetic) may be a component of a kit for detecting coagulation (clotting). Such a kit would enable detection of a role (if any) of $\beta_2$GPI-dependent antiphospholipid antibodies in mediating the thrombosis pathway. For example, $\beta_2$GPI-dependent antiphospholipid antibodies delays the inactivation of activated Factor Va by activated protein C or activate the tissue factor coagulation pathway. We have found that domain 1 specific anti-02GPI antibodies delay the inactivation of Factor Va as discussed in Example 11. A domain 1 $\beta_2$GPI polypeptide(s) (and/or mimetic(s)) may be useful in discriminating $\beta_2$GPI-dependent antiphospholipid antibody-mediated effects from other mechanisms influencing the inactivation of Factor Va or the activation of the tissue factor pathway. In addition, domain 1 $\beta_2$GPI polypeptide(s) (and/or mimetic(s)) may be useful in other functional coagulation (such as thrombosis) assays in which $\beta_2$GPI-dependent antiphospholipid antibodies or serum or plasma from individuals influences the outcome of the specific coagulation assay. For example, if the presence of a domain 1 $\beta_2$GPI polypeptide(s) (and/or mimetic(s)) alters the outcome of a coagulation assay (when compared to the results of such an assay in the absence of a domain 1 $\beta_2$GPI polypeptide(s) (and/or mimetic(s)), $\beta_2$GPI-dependent antiphospholipid antibodies are implicated in the clotting pathway. This information could be especially valuable in assessing potential specific treatments.

Methods Using Domain 1 β₂GPI Polypeptides (and Domain 1 β₂GPI Polypeptide Mimetics)

The invention also provides methods using a domain 1 β₂GPI polypeptide(s) (and/or a domain 1 β₂GPI polypeptide mimetic(s)), which are applicable in a detection and/or a therapeutic context. Accordingly, the invention encompasses methods using the β₂GPI polypeptide(s) of the invention (and/or domain 1 β₂GPI polypeptide mimetic(s) of the invention) to detect suitable targets in a biological sample. Procedures for conducting diagnostic (i.e., detection) tests using polypeptides are extensively known in the art and are routine for a practitioner of ordinary skill. Generally, to perform a diagnostic (i.e., detection) method of this invention, one of the polypeptides or mimetics of this invention (generally as a composition) is provided as a reagent to detect a target with which it reacts in a biological sample. The target is supplied by obtaining a suitable biological sample from an individual for whom the diagnostic parameter is to be measured. If desired, the target may be partially purified from the sample or amplified before the assay is conducted. The invention also provides methods of purifying an β₂GPI-dependent antiphospholipid antibody using a polypeptide(s) or mimetic(s) of the invention. The invention also provides methods using the polypeptides polynucleotides, and/or mimetics of this invention to induce tolerance.

Detection of β₂GPI-Dependent Antiphospholipid Antibody

In one embodiment, the invention provides methods of detecting an antibody that specifically binds to a domain 1 β₂GPI polypeptide(s), preferably a β₂GPI-dependent antiphospholipid antibody, in a biological sample. These methods are 1.4 generally applicable in the clinical setting, for example, for diagnosing and/or monitoring β₂GPI-dependent antiphospholipid antibody levels in an individual. These methods entail contacting (02GPI-dependent antiphospholipid) antibody in the sample with a domain 12GPI polypeptide(s) (i.e., any polypeptide of this invention) under conditions suitable to allow the formation of a stable complex between anti-domain 1 β₂GPI specific antibody (such as an β₂GPI-dependent antiphospholipid antibody) and a domain 1 β₂GPI polypeptide(s), and detecting a stable complex formed, if any. The domain 1 β₂GPI polypeptide(s) of the invention render these methods particularly useful, as no generally convenient or suitable assay for these antibodies has yet been developed. A number of immunoassay methods are known in the art and need not be described in detail. Suitable samples in which to measure β₂GPI-dependent antiphospholipid antibody are biological samples, including serum or plasma (preferably serum) and target tissue eluate. It is well understood in the art that detection of a complex formed may be direct (such as by measuring the amount of label associated with a complex) or indirect (such as in measuring the amount of labeled ligand which is displaced during the assay).

To use the polypeptide(s) or mimetic(s) of this invention in the detection of such antibodies in an individual, an immunoassay is conducted. The polypeptide(s) or mimetic(s) is provided as a reagent, and the antibody is the target in the biological sample. For example, human IgG antibody molecules present in a serum sample may be captured with solid-phase protein A, and then overlaid with the labeled polypeptide reagent. The amount of antibody would then be proportional to the label attached to the solid phase. Alternatively, cells or tissue sections expressing the polypeptide may be overlaid first with the test sample containing the antibody, and then with a detecting reagent such as labeled anti-immunoglobulin. The amount of antibody would then be proportional to the label attached to the cells. The amount of antibody detected in the sample would be compared with the amount detected in a control sample.

In the methods of the invention, domain 1 β₂GPI polypeptide or mimetic will typically be immobilized, by known techniques, onto a suitable solid phase, such as affinity column packing material, or a plastic surface such as a microtiter plate or a dipstick. Appropriate affinity column packing materials include, for example, a beaded agarose matrix, polyacrylamide, glass, cellulose or cross-linked dextran. Suitable plastic surfaces include polymethacrylate, polystyrene, polyethylene, polyterepthalate, ethylene glycol, polyester, polypropylene, and the like. Generally, any standard microtiter plate may be used. Alternatively, the solid phase may be in the form of a gel or matrix into which the domain 1 β₂GPI polypeptide or mimetic is incorporated.

For further illustration, a test sample potentially containing an antibody that specifically binds to a domain 1 β₂GPI polypeptide(s) (such as β₂GPI-dependent antiphospholipid antibody) can be mixed with a pre-determined non-limiting amount of the domain 1 β₂GPI polypeptide(s) which is generally detectably labeled (such as with a radioisotope or enzyme). In a liquid phase assay, unreacted reagents are removed by a separation technique, such as filtration or chromatography. In these immunoassay techniques, the amount of label associated with the complex positively correlates with the amount of β₂GPI-dependent antiphospholipid antibody present in the sample. Similar assays can be designed in which β₂GPI-dependent antiphospholipid antibody in the test sample compete with labeled antibody for binding to a limiting amount of the domain 1 β₂GPI polypeptide(s). Here, the amount of label negatively correlates with the amount of β₂GPI-dependent antiphospholipid antibody in the sample.

In some embodiments, the biological sample is a tissue sample, or a tissue eluate, and the amount of β₂GPI-dependent antiphospholipid antibody associated with the tissue sample is measured by, for example, a competitive binding assay. These methods may be especially useful in those contexts in which a particular tissue should be tested and/or monitored for presence and/or amount of β₂GPI-dependent antiphospholipid antibody. This type of assay may indicate, for example, whether a particular disease (or risk of disease) may be indicated (such as a particular form of thrombosis or clotting disorder). Such an assay may also be useful in providing more precise and sensitive determination of localization of β₂GPI-dependent antiphospholipid antibody for diagnostic and/or monitoring purposes. Further, localization information about β₂GPI-dependent antiphospholipid may also provide a clinician with indication about suitable treatment options.

It is understood that these detection methods are applicable in a variety of clinical contexts. For instance, detection may be used to identify individuals who show risk of developing β₂GPI-dependent antiphospholipid-associated conditions or disorders (which may in turn arise from being able to distinguish antibodies associated with pathology and those not associated with pathology). Detection may also be used to monitor treatment (such as administration of any of the compositions described above). Detection may also assist in distinguishing between pathogenic antibodies from non-pathogenic antibodies. Detection may also assist the clinician in deciding the best treatment options and/or prognosis.

As discussed above, a domain 1 β₂GPI polypeptide(s) (and/or mimetic(s)) may also be used as a diagnostic component in a coagulation assay, specifically an assay in which $\beta_2$GPI-dependent antiphospholipid antibodies can modify the outcome of a specific coagulation assay. For example, if the presence of a domain 1 $\beta_2$GPI polypeptide(s) (and/or mimetic(s)) alters the outcome of a coagulation assay (when compared to the results of such an assay in the absence of a domain 1 $\beta_2$GPI polypeptide(s) (and/or mimetic(s)), $\beta_2$GPI-dependent antiphospholipid antibodies are implicated in the clotting pathway. Because domain 1 $\beta_2$GPI polypeptide(s) (and/or mimetic(s)) may be useful in discriminating $\beta_2$GPI-dependent antiphospholipid antibody-mediated effects from other mechanisms in coagulation (such as thrombosis), the invention includes methods of detecting participation (mediation) of a $\beta_2$GPI-dependent antiphospholipid antibody in coagulation (such as thrombosis), comprising (a) performing a coagulation assay using a suitable biological sample from an individual, using a domain 1 $\beta_2$GPI polypeptide(s) (and/or mimetic(s)); (b) performing a coagulation assay using a suitable biological sample from an individual, without using a domain 1 $\beta_2$GPI polypeptide(s) (and/or mimetic(s)); (c) compare the results of (a) and (b), wherein a difference in result indicates participation of a $\beta_2$GPI-dependent antiphospholipid antibody in coagulation. These methods can also be used to monitor a patient's status in terms of mediation of an $\beta_2$GPI-dependent antiphospholipid antibodies in coagulation, as well as initial detection. These methods also indicate, or detect, a coagulation abnormality involving (i.e., mediated by) $\beta_2$GPI-dependent antiphospholipid antibodies.

For these methods, plasma or serum may be used. Alternatively, the IgG fraction, isolated using standard methods in the art, is used. An example of a coagulation detection system is provided in Example 11. In some embodiments, activated factor V (Va) levels are determined, generally by measuring time to clot. Assays, equipment, and kits to detect coagulation are known in the art and are commercially available.

Purification of $\beta_2$GPI-dependent antiphospholipid antibodies

The invention also includes methods of purifying an antibody which specifically binds to a domain 1$\beta_2$GPI polypeptide(s) (such as a $\beta_2$GPI-dependent antiphospholipid antibody) comprising contacting a biological sample containing $\beta_2$GPI-dependent antiphospholipid antibody with a domain 1$\beta_2$GPI polypeptide(s) or a mimetic of a domain 1$\beta_2$GPI polypeptide(s) under conditions that permit formation of a stable antigen-antibody complex, and obtaining a complex formed, if any. Typically, the domain 1$\beta_2$GPI polypeptide(s) or mimetic(s) is coupled to an affinity matrix for affinity column purification. Such methods are routine in the art and need not be described in detail herein. Example 1 also describes affinity purification of $\beta_2$GPI-dependent antiphospholipid antibody.

Methods of Inducing Tolerance

Also included in this invention of methods of inducing tolerance (i.e., a toleragenic state), comprising administering to an individual an effective amount of a domain 1 $\beta_2$GPI polypeptide(s) (or a polypeptide which comprises a domain 1 $\beta_2$GPI polypeptide(s)) or a mimetic of a domain 1 $\beta_2$GPI polypeptide(s), all of which also lack(s) a detectable T cell epitope. Preferably, the domain 1 $\beta_2$GPI polypeptide(s) (or any polypeptide comprising the domain 1 $\beta_2$GPI polypeptide(s)) or mimetic(s) is also conjugated to a suitable platform molecule, as described above. It is understood that, for purposes of this invention, that the immune response to be reduced (and/or eliminated, stabilized, and/or rate of increase reduced, via inducing tolerance, is an immune response to $\beta_2$GPI. Accordingly, the tolerance induced is antigen specific, wherein the antigen is $\beta_2$GPI, and the tolerance is achieved in an individual who has been determined to have (at least before administration of the polypeptide(s) and/or mimetic(s) of this invention) $\beta_2$GPI dependent antiphospholipid antibodies.

The appropriate polypeptides of this invention (that is, polypeptides comprising a domain 1 $\beta_2$GPI polypeptide(s) or mimetic(s) which lacks a T cell epitope) may be used alone or in conjunction with other agents which promote the desired activity/objective. As discussed above, various polypeptides may also be used in various combinations with each other. Various formulations and means of administration have been discussed above.

Determination of whether tolerance has been induced can be achieved by any means known in the art. In general, tolerance is determined by measuring the immune response to a domain 1 $\beta_2$GPI polypeptide(s). An immune response to a domain 1 $\beta_2$GPI polypeptide(s) can be measured using standard assays, including, for example, measuring levels of antibody which bind to domain 1 $\beta_2$GPI polypeptide(s) or mimetic(s); measuring cytokine production following immunization with a domain $\beta_2$GPI polypeptide(s); performing in vitro analyses of T-cell response to a domain 1 $\beta_2$GPI polypeptide(s) after administration of a $\beta_2$GPI polypeptide(s) or mimetic(s) of the invention using T cells from the individual receiving such administration (i.e., an individual with $\beta_2$GPI-dependent antiphospholipid antibodies), including, for example, standard assays $^3$H-thymidine uptake to measure proliferation of T cells when presented with a domain 1 $\beta_2$GPI polypeptide(s) in the context of an antigen-presenting cell, standard $^{51}$Cr release assays to measure killing by cytotoxic T-cells of a cell presenting a domain 1 $\beta_2$GPI polypeptide(s), and the like.

The following examples are provided to illustrate but not limit the present invention.

EXAMPLES

Example 1

Domain 1 of $\beta_2$GPI is Immunoreactive with $\beta_2$GPI-Dependent Antiphospholipid Antibodies Materials and Methods Construction of Domain Deletion Mutants $\beta_2$GPI is comprised of 5 "sushi" domains. To determine the antigenic region(s) of $\beta_2$GPI, we selectively removed one or more domains from $\beta_2$GPI. This approach was employed by Igarashi et al ((1996) *Blood* 87:3262–3270) in which they made deletions of human $\beta_2$GPI which contained domain 4 and 5, domains 3 through 5, domains 2 through 5, domains 1 through 4, and domains 1 through 3. In addition to the domain deletion mutants described by Igarashi et al., we constructed human $\beta_2$GPI mutants containing only domains 1 and 2.

The starting point for the construction of these deletion mutants was the full length cDNA of human $\beta_2$GPI (Steinkasserer et al. (1991) *Biochem. J.* 277:387–391) cloned into pBacPAK9 (Clontech), a gift from S. Krilis. The initial step was to introduce a GlyHis$_6$ at the C-terminus. In the process, a unique Msc 1 restriction site (TGGCCA) was created by changing the C-terminal Cys codon from TGC to TGT followed by Gly (GGC) and His (CAC). The purpose of the His$_6$ tag was to allow for facile purification of the mutant proteins by Ni chelation chromatography.

The GlyHis$_6$ was introduced by single stranded DNA site directed mutagenesis. The method employed closely followed the published procedures of Kunkel et al. *Methods in Enzymology* (1987) 154:367–382. When cells containing phagemid pBacPAK9 into which the cDNA for human β₂GPI has been inserted were infected by a helper phage, M13K07, the phage particles collected from the growth media predominantly contained a single stranded DNA version of the pBacPAK9. Further, if the cells employed were of the dut 1, ung 1 genotype such as CJ236, some thymidine in the DNA was replaced by uridine. The single stranded DNA was purified from the phage by phenol extraction and ethanol precipitation.

The oligonucleotide, ApoH-G6H, with the sequence 5' AAACCACCTTAATGGTGATGGTGATGGTGGCCAC ATGGCTTTACA 3' (SEQ ID NO: 13) which is complementary to regions on either side of the C-terminal Cys and encodes GlyHis₆ was annealed to the single stranded DNA of pBacPAK9 containing the gene for human β₂GPI which had been grown in E. coli, CJ236. The method of Kunkel was used to elongate the complementary oligonucleotide resulting in double stranded DNA. The reaction was transformed into E. coli K91. Strain K91 does not contain the dut 1, ung 1 genotype with the result that uridine containing DNA will be degraded. The newly synthesized strand encoding the GlyHis₆ should be enriched. Clones were analyzed by DNA sequence using either the T7 sequenase kit or the thermo sequenase kit (Amersham Life Sciences).

The following oligonucleotides were used in the above described manner to generate domain deletion mutants of human β₂GPI:

B2del3-60
5' GAC ATA CTC TGG GTG TCC GTC CTG CAA TAG C 3' (SEQ ID NO:14)

B2del3-120
5' TGG AGG GCA GAT GAT CCG TCC TGC AAT AGC 3' (SEQ ID NO: 15)

B2del3-182
5' GAA TGG GCA TTT TAC TTC CCG TCC TGC AAT AGC 3' (SEQ ID NO: 16)

B2del3-242
5' AGG TAA TTT ACA AGA TGC CCG TCC TGC AAT AGC 3' (SEQ ID NO: 17)

B2del242-326
5' ATG GTG ATG GTG GCC ACA ACT TGG CAT GGC 3' (SEQ ID NO:18)

B2del 182-326
5' ATG GTG ATG GTG GCC GCA TTC TGG TAA TTT AG 3' (SEQ ID NO: 19)

The numbers in the oligonucleotides refer to the amino acids of human β₂GPI. For example, B2del3-60 refers to amino acids 3–60 being deleted from β₂GPI. The resulting protein contains domains 2–5.

A summary of the constructions follows.

| Domain(s) | Construction | Expected protein sequence | SEQ ID NO: |
|---|---|---|---|
| 2,3,4,5 | B2del3-60 | GRTPR | 20 |
| 3,4,5 | B2del3-120 | GRIIC | 21 |
| 4,5 | B2del3-182 | GREVK | 22 |
| 5 | B2del3-242 | GRASC | 23 |
| 1,2,3,4 | B2del242-326 | GRTCP | 24 |
| 1,2,3 | B2del182-326 | GRTCP | 24 |

PCR was used to generate other mutants. The template for the reaction was the pBacPAK9 containing the cDNA for human β₂GPI. The oligonucleotide, pBacPac9 PCR 1270, 1297, which has the sequence 5' CTA TAA ATA CGG ATC CCG GGA ATT CG 3' (SEQ ID NO:25) and primes upstream of the multicloning region in pBacPAK9 was used as the 5' primer. To construct clones with only domain 1, the oligonucleotide Domain 1 PCR (64) Msc1, with the sequence 5' GCA GCT GGC CAA CTC TGG GTG TAC ATT TCA GAG TG 3' (SEQ ID NO:26) was used as the 3' primer. Similarly, to generate a mutant containing domains 1 and 2 the oligonucleotide, Domain 1, 2 PCR (122) Msc 1, with the sequence 5' GCA GCT GGC CAA TGA TGG GAG CAC AGA GAGOGAA G 3' (SEQ ID NO:27) was used as the 0.3° primer. Twenty five rounds of PCR were performed. The product was phenol extracted and ethanol precipitated. The fragments were digested at the 5' end with Bam H1 and Msc 1 at the 3' end. The digested DNA fragments were gel purified and ligated into pBacPAK9 from which the full length β₂GPI had been excised with the same restriction enzymes. The ligations were transformed into E. Coli XL1-blue and clones were characterized by DNA sequencing. The results follow:

| Domain(s) | Construction | Expected protein sequence | SEQ ID NO: |
|---|---|---|---|
| 1 | B2del165-326 | GRTCP | 24 |
| 1,2 | B2del123-326 | GRTCP | 24 |

All deletion mutants of β₂GPI were purified from the media of infected insect cells. In general, cells were removed by centrifugation and the media dialyzed against at least 10 volumes of phosphate buffered saline (PBS; 137 mM NaCl, 2.7 mM KCl, 4.3 mM Na₂HPO₄. 7H2O, 1.4 mM KH₂PO₄) for 18 hours at 4° C. The next day, any precipitate was removed by centrifugation. The dialyzed media was made 50 mM NaPO₄, pH 7.5, 0.5 M NaCl and Ni-NTA resin was added to the dialyzed media with gentle mixing. After 1 hour at 4° C., the resin was collected with a Buchner funnel and packed into a water jacketed column kept at 4 degrees. The column was washed extensively with 50 mM NaPO₄ pH7.5, 0.5 M NaCl until no protein was detectable. The column was eluted sequentially with the same buffer containing 20 mM, 35 mM or 100 mM imidazole. Analysis was by sodium dodecyl sulfate-polyacrylamide gel electrophoresis (SDS PAGE). Appropriate fractions were pooled and protein was concentrated and dialyzed against Tris-buffered-saline (TBS; 50 mM TrisCl pH 7.5, 150 mM NaCl).

Affinity Purified β₂GPI-Dependent Antiphospholipid Antibodies

To isolate β₂GPI-dependent antiphospholipid antibodies, multilamellar, cardiolipin-containing lipid dispersions (also containing cholesterol and dicetylphosphate) are incubated with β₂GPI-dependent antiphospholipid plasma (or serum). These liposomes are pelleted from the serum by centrifugation. After washing, the liposome mixture is disrupted by 2% octylglucoside detergent and applied to a protein A-agarose column. Following extensive washings to first remove lipids and then to remove non-IgG components, IgG ₂GPI-dependent antiphospholipid antibody is eluted from protein A with mild acid, neutralized, buffer-exchanged, and tested in the ACA ELISA. This procedure yields aPL antibody enriched up to 10,000-fold that is devoid of any contaminating β₂-GPI as shown by Western blotting with rabbit IgG anti-human β₂-GPI antisera. A specific example of this procedure follows.

β$_2$GPI-Dependent Antiphospholipid Antibody Purification From Serum

Antibodies from various patients was purified from serum from patients of various ages exhibiting various symptoms including: SLE, APS (including various manifestations of APS, including venous thrombosis, miscarriage, thrombocytopenia, CVA (cerebrovascular accident, i.e., stroke), TIA (transient ischemic attacks)), and arterial occlusion).

In a 25 mL round-bottom flask (Kontes Scientific Co., Vineland, N.J.) a mixture of 1.2 mL cardiolipin (Sigma Chemical, St. Louis, Mo., #C-1649), 0.464 mL cholesterol (Sigma Diag., St. Louis, Mo., #965-25), 0.088 mL of 5 mg dicetylphosphate (Sigma Chemical, St. Louis, Mo., D-263 1) per mL chloroform was dried for approximately 5 minutes in a Rotavap (Buchi, Switzerland). Following the removal of solvent, 2 mL of 0.96,% (wt./vol.) NaCl (J. T. Baker, Inc., Phillipsburg, N.J.) was added and mixed in a Vortex Genie Mixer (Scientific Industries, Inc., Bohemia, N.Y.) for 11 minutes. The liposome suspension was incubated for 1 hour at 37° C. Meanwhile, serum 6501 was spun at 600×g in a Sorvall RT 6000 centrifuge (Dupont Co. Wilmington, Del.) for 10 minutes at 8° C. Four mL of the supernatant was placed in a 25 mL round-bottom flask with 1 mL of the prepared liposome suspension and the mixture was incubated with agitation at medium speed in an orbital shaker, Tektator V (Scientific Products, McGraw Park, Ill.) for 48 hours at 4° C., and an additional 2 hours at 37° C. Twenty mL of cold TBS was added and the mixture was transferred into a 50 mL polycarbonate centrifuge tube (Nalge Co., Rochester, N.Y.) and centrifuged at 27,000×g for 15 minutes at 4° C. in an RC3 centrifuge in a SS-34 rotor (Sorvall-Dupont, Wilmington, Del.). The precipitate was washed 3 times with 25 mL of cold 0.96% NaCl using the RC3 centrifuge. The pellet was dissolved in 1 mL of 2% (wt/vol) solution of n-octyl-β-D-glucopyranoside (Calbiochem, La Jolla, Calif.) in TBS and applied to a 0.6 mL protein A/crosslinked agarose (Repligen Corporation, Cambridge, Mass.) column which had been pre-washed with 15 times bed volume of 1 M acetic acid and equilibrated with 15 times bed volumes of TBS. The antibody-protein A/agarose column was washed with 40 times bed volume of 2% octylglucopyranoside to remove lipids, followed by extensive washings with TBS until the optical density of the eluate at 280 nm approached the baseline. The bound antibody was eluted with 1 M acetic acid. One mL fractions were collected, neutralized immediately with 0.34 mL 3M Tris (Bio-Rad, electrophoresis grade) per fraction and kept in an ice bath. The optical density of each fraction was determined at 280 nm in a spectrophotometer (Hewlett-Packard, 8452A Diode Array Spectrophotometer, Palo Alto, Calif.). Fractions containing antibody were pooled, concentrated and washed 4 times with TBS in Centricon-30 concentrators (Amicon Division, W. R. Grace & Co., Beverly, Mass.) per manufacturer's protocol. The final yield of purified antibody from 4 mL of serum 6501 was determined by reading the optical density at 280 run of an aliquot from the concentration, where 1 mg=1.34 $A_{280mm}$. The average yield obtained was 750 μg antibody from 4 mL of serum 6501. The purified antibody was tested for ACA activity and checked for purity with Laemmli SDS-PAGE.

Cardiolipin Based ELISA

Microtiter plates (Immulon 1 #3350 from Dynex Technologies) were coated with 30 μl of a 50 μg/ml solution of cardiolipin in ethanol, dried overnight at 4° C., washed three times with PBS, pH 7.2, and blocked for one hour at room temperature with 75 μl of 5% (wt/v) fish gelatin, (Hipure Liquid Gelatin, Norland Products Inc. 695 Joyce Kilmer Ave., New Brunswick N.J., USA). The plates were washed three times with PBS, charged with 50 μl of full length recombinant β$_2$GPI at 10 μg/ml in 5% fish gelatin and incubated at 37° C. for one hour. The plates were washed three times with PBS, 50 μl of either affinity purified β$_2$GPI-dependent antiphospholipid antibodies (the concentration of each antibody used is shown in Table 2, or rabbit anti-02GPI was added to each well and incubated at 37° C. for one hour. The plates were washed three times with PBS, 50 pd of alkaline phosphatase conjugated anti-immunoglobulin (anti-human IgG, gamma chain specific, Zymed #62-8422 or anti-rabbit IgG, Zymed #362-61220 diluted appropriately in 5% fish gelatin was added and incubated at 37° C. for one hour. The plates were washed three times with PBS, 50 μl of alkaline phosphatase chromogenic substrate was added (PPMP solution; 7.8 g phenolphthalein monophosphate plus 69.5 g of 2-amino-2-methyl-1-propanol in 100 mL water stock solution diluted 1:26 with water immediately before use) and incubated for 30 minutes, at room temperature. The optical density, at 550 nm, was determined by reading the plates in a microplate autoreader (Bio-Teck Instruments, model EL311).

Competitive Inhibition ELISA

Microtiter plates (MaxiSorp™, Nalge Nunc International, Denmark) were coated with 50 μl of full length recombinant β$_2$GPI at 10 μg/ml in 0.1 M bicarbonate, pH 9.5, incubated overnight at 4° C., washed three times with 0.15 M PBS, pH 7.2, and blocked for one hour at room temperature with 75 μl of 2% Non-fat Dried Milk (Carnation, 2% NFDM). Test inhibitors were diluted in 2% NFDM and 25 μl of each dilution was added to coated wells. Affinity purified β$_2$GPI-dependent antiphospholipid antibody was diluted in 2% NFDM and 25 μl, of a constant concentration, was added to the wells, including a group of wells that had no inhibitor, which acted as the positive controls. The contents of the wells were mixed and the plates were incubated at 37° C. for one hour. The plates were washed three times with PBS, 50 μl of alkaline phosphatase conjugated anti-human IgG, gamma chain specific, (Zymed #62-8422) diluted appropriately in 2% NFDM was added and incubated at 37° C. for one hour. The plates were washed three times with PBS, 50 μl of alkaline phosphatase PPMP chromogenic substrate solution was added and incubated for 30 minutes, at room temperature. The Optical Density, at 550 nm, was determined by reading the plates in a microplate autoreader (Bio-Teck Instruments, model EL3 11). The percent inhibition was determined by dividing the OD$_{550}$ obtained in the presence of inhibitor by the mean OD$_{550}$ obtained from the wells without inhibitor and then multiplying by 100 (more particularly, [mean A$_{550}$ obtained from control wells without inhibitor less A$_{550}$ of background] minus [A$_{550}$ obtained in presence of inhibitor less A$_{550}$ of background] divided by [mean A$_{550}$ obtained from control wells without inhibitor less A$_{550}$ of background] times 100).

Direct Binding of Recombinant β$_2$GPI and Mutants, Assessed by ELISA

Nickel Chelate-coated microwell plates (NCP 010 00 Xenopore Corp. 374 Midland Ave. Saddle Brook, N.J. USA) were coated with 50 μl of serial dilutions of the various recombinant β$_2$GPI, in PBS, at room temperature for 2 hours. The plates were washed three times with PBS and blocked with 75 μl of a 1% gelatin (Sigma #G-2500) in PBS for one hour room temperature. The plates were washed three times with PBS, 50 µl of either affinity purified β$_2$GPI-dependent antiphospholipid antibody (at a concentration that had previously been shown to give about 80% of maximum binding) or rabbit anti-β$_2$GPI was added and incubated at 37° C. for one hour. The plates were washed three times with PBS, 50 µl of alkaline phosphatase conjugated anti-immunoglobulin (anti-human IgG, gamma chain specific, Zymed #62-8422) or anti-rabbit IgG (Zymed #62-

Figure 14:
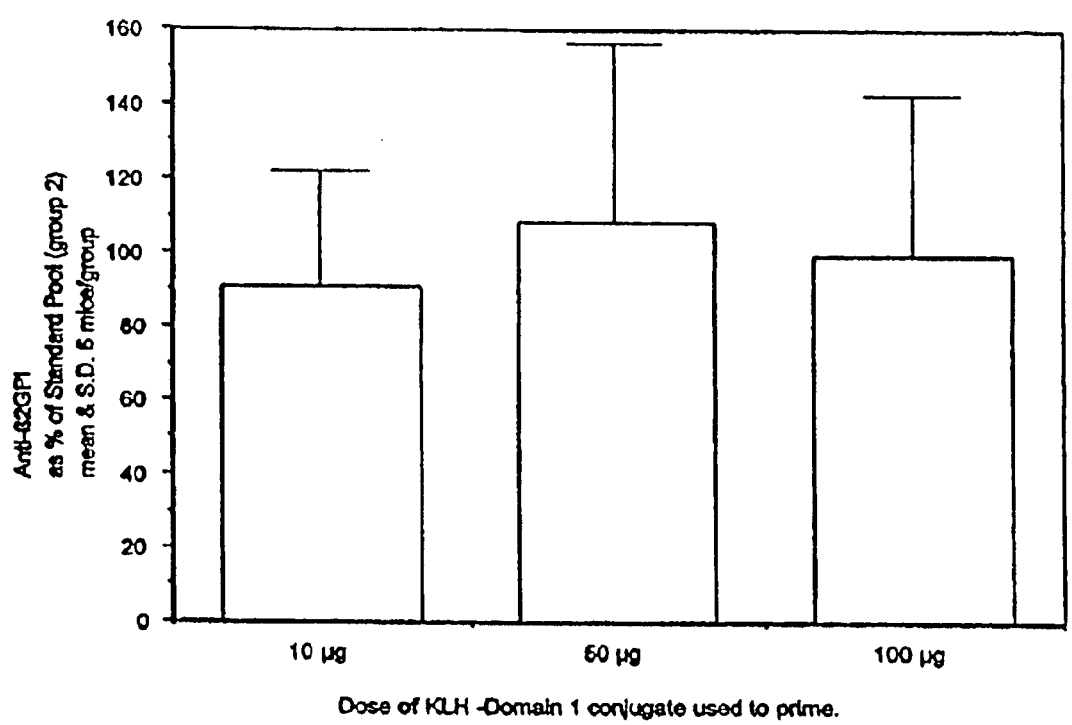
FIG. 14 is a bar graph depicting a dose response (in terms of anti-β$_2$GPI antibody) of priming with a β$_2$GPI domain 1 polypeptide-KLH conjugate (10 µg, 50 µg, and 100 µg).
Figure 15:
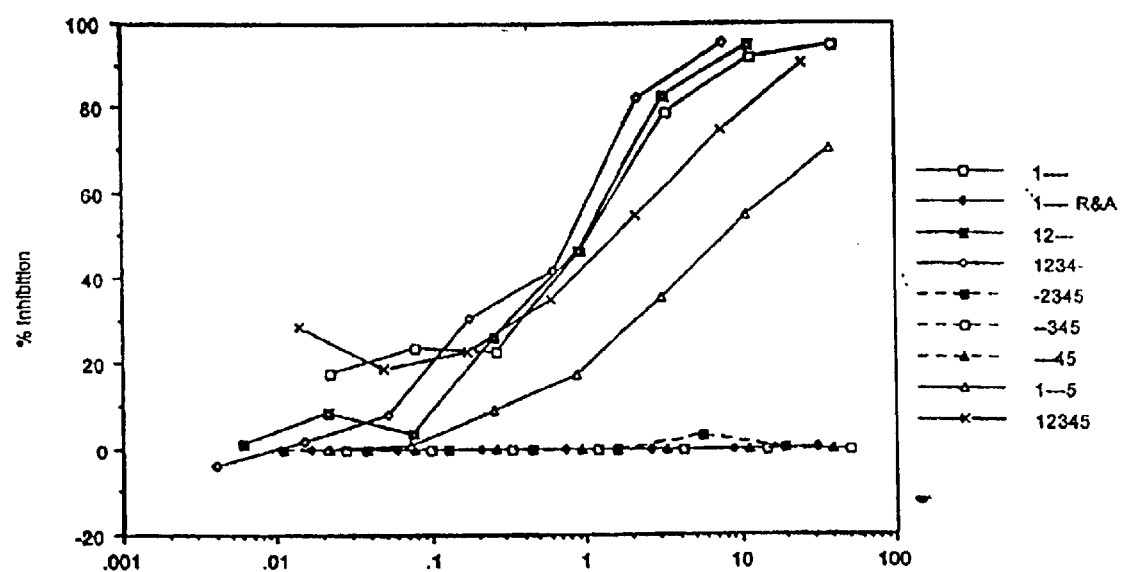
FIG. 15 is a graph depicting specificity of mouse polyclonal antibodies raised against a β$_2$GPI domain 1 polypeptide-KLH conjugate, as determined by competition assays using various β$_2$GPI domain mutants (—□—, 1 - - - - ; —◆—, 1 - - - - reduced and alkylated; —◙—, 12 - - ; —Δ—, 1234- ; - - - ■ - - - , - 2345; - - - □ - - - , - - 345; - ▼ - - , - - - 45; —Δ—, 1- - - 5; —X—, 12345).

Only those mutants that contained domain 1 inhibited the β$_2$GPI-dependent antiphospholipid antibodies from binding to the full length recombinant β$_2$GPI (FIG. 14). This was true for all 13 β$_2$GPI-dependent antiphospholipid antibody preparations (Table 2). The fact that all of the recombinant mutant β$_2$GPI proteins that contain domain 1 inhibited greater than 90% indicates that all of the detectable anti-β$_2$GPI activity of these antibodies is directed against domain 1.

TABLE 2

Summary of data from competitive inhibition assays using 13 different β$_2$GPI-dependent antiphospholipid antibody preparations versus nine recombinant β$_2$GPI proteins.
Max = maximum inhibition observed at concentrations tested. 50% = concentration (µM) to give 50% inhibition.

| | 12345 | | 1---- | | | 12--- | | 123-- | | 1234- | | -2345 | | --345 | | ---45 | | ----5 | |
|---|---|---|---|---|---|---|---|---|---|---|---|---|---|---|---|---|---|---|---|
| Ab# | Max | 50% | Max | | 50% | Max | 50% | Max | 50% | Max | 50% | Max | 50% | Max | 50% | Max | 50% | Max | 50% |
| 7104 | 90 | 0.8 | 90 | 0 | 0.8 | 90 | 1 | 98 | 1 | 90 | 0.7 | 10 | >57 | 20 | >50 | 5 | >40 | 0 | >47 |
| 6203 | 75 | 0.8 | 60 | (20) | >10 | 20 | >10 | 75 | 1 | 30 | >8 | 10 | >57 | 10 | >50 | 10 | >40 | 5 | >47 |
| 7008 | 90 | 0.2 | 70 | (40) | >10 | 40 | >10 | 80 | 0.4 | 50 | >8 | 20 | >57 | 20 | >50 | 20 | >40 | 20 | >47 |
| 6501 | 80 | 0.2 | 70 | (30) | 30 (>10) | 30 | >10 | 85 | 0.8 | 30 | >8 | 20 | >57 | 15 | >50 | 15 | >40 | 10 | >47 |
| 6626 | 80 | 0.3 | 85 | (50) | 8 (>10) | 50 | >10 | 90 | 0.8 | 40 | >8 | 18 | >57 | 20 | >50 | 15 | >40 | 10 | >47 |
| 6632 | 90 | 0.8 | 90 | (70) | 8 (3) | 70 | 3 | 90 | 0.2 | 60 | 2 | 20 | >57 | 20 | >50 | 20 | >40 | 10 | >47 |
| 6644 | 90 | 0.2 | 90 | (45) | 8 (>10) | 45 | >10 | 90 | 0.7 | 50 | 8 | 10 | >57 | 10 | >50 | 10 | >40 | 10 | >47 |
| 7015 | 90 | 0.2 | 90 | (30) | 8 (>10) | 30 | >10 | 90 | 0.7 | 50 | 8 | 10 | >57 | 10 | >50 | 10 | >40 | 10 | >47 |
| 7101 | 80 | 0.8 | 70 | (20) | 8 (>10) | 20 | >10 | 70 | 3 | 20 | >8 | 5 | >57 | 5 | >50 | 5 | >40 | 5 | >47 |
| 6652 | 95 | 0.8 | ND | | ND | ND | ND | 95 | 0.3 | 100 | 0.5 | 40 | >16 | 30 | >15 | 20 | >5 | 15 | >47 |
| 6509 | 70 | 0.1 | ND | | ND | ND | ND | 90 | 0.3 | 80 | 3 | 20 | >16 | 20 | >15 | 20 | >5 | 10 | >47 |
| 6701 | 100 | 0.1 | ND | (80) | ND (4) | ND | ND | 95 | 0.3 | 30 | >8 | 10 | >16 | 20 | >15 | 15 | >5 | 10 | >47 |
| 6641 | 96 | 0.1 | ND | (98) | ND (>10) | ND | ND | 60 | 4 | 60 | 2 | 20 | >16 | 10 | >15 | 20 | >5 | 10 | >47 |

6122) diluted appropriately in 1% gelatin was added and incubated at 37° C. for one hour. The plates were washed three times with PBS, 50 µl of alkaline phosphatase PPMP chromogenic substrate solution was added and incubated for 30 minutes at room temperature. The optical density, at 550 nm, was determined by reading the plates in a microplate autoreader (Bio-Teck Instruments, model EL311).

Results of Inhibition Studies

Figure 4:
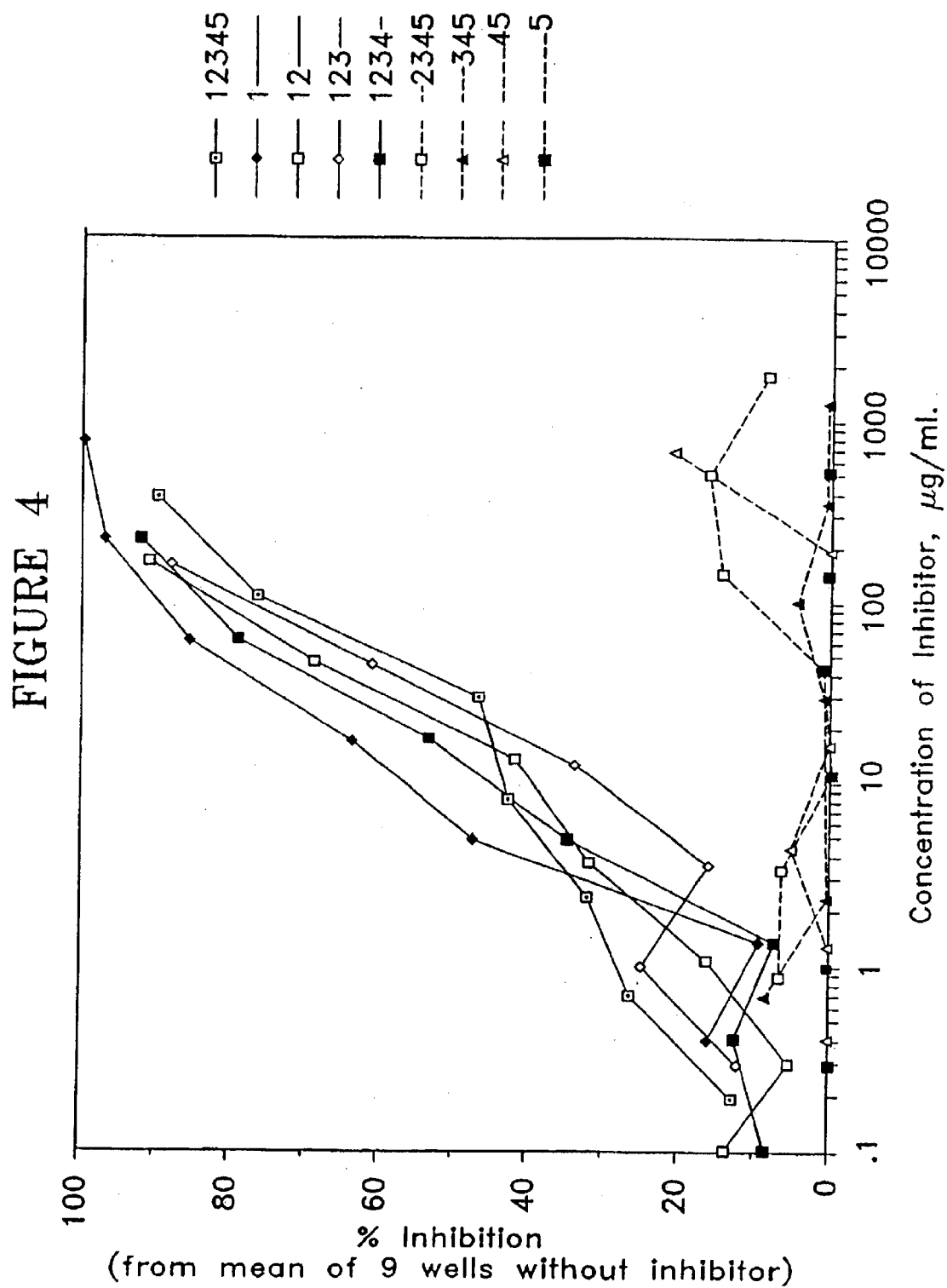
FIG. 4 is a graph depicting the results of a competitive inhibition ELISA performed on NUNC microtiter plates. Plates were coated with wild type β$_2$GPI. Antibody (from patient 7104) binding was competed with the various mutant β$_2$GPI proteins. Symbols represent recombinant β$_2$GPI proteins as follows: —□—, 12345; —□—, 1 - - - - ; —◙—, 12 - - - ; —□—, 123 - - ; —◙—, -2345; —▲—, - - 345; —□—, - - - 45; and —□—, - - - - 5. Recombinant protein designations: dashes indicate missing domains; numbers indicate domains present in the protein. For example, "'- - - 345" is a recombinant 2GPI protein lacking domains 1 and 2, but retaining domains 3, 4, and 5.

Seven to nine different recombinant β$_2$GPI mutant proteins were used to determine the antigenic specificity of affinity purified β$_2$GPI-dependent antiphospholipid antibody preparations from 13 different patients. Each mutant recombinant β$_2$GPI protein was tested, in a dose dependent fashion, for its ability to inhibit affinity purified β$_2$GPI-dependent antiphospholipid antibody from binding to full length recombinant β$_2$GPI. The results from a typical assay are shown in FIG. 4. The results from assays of all 13 affinity purified β$_2$GPI-dependent antiphospholipid antibodies are summarized in Table 2. The following values were also observed for domain 1 only recombinant protein (1 - - - - ; see Table 2 for designations):

Ab 6203, Max 20, 50%>10; Ab 7008, Max 40, 50%>10; Ab 6501, Max 30, 50%>10; Ab 6626, Max 50, 50%>10; Ab 6632, Max 70, 50% 3; Ab 6644, Max 45, 50%>10; Ab 7015, Max 30, 50%>10; Ab 7101, Max 20, 50%>10; Ab 6701, Max 80, 50% 4; Ab 6641, Max 98, 50%>10.

Figure 5:
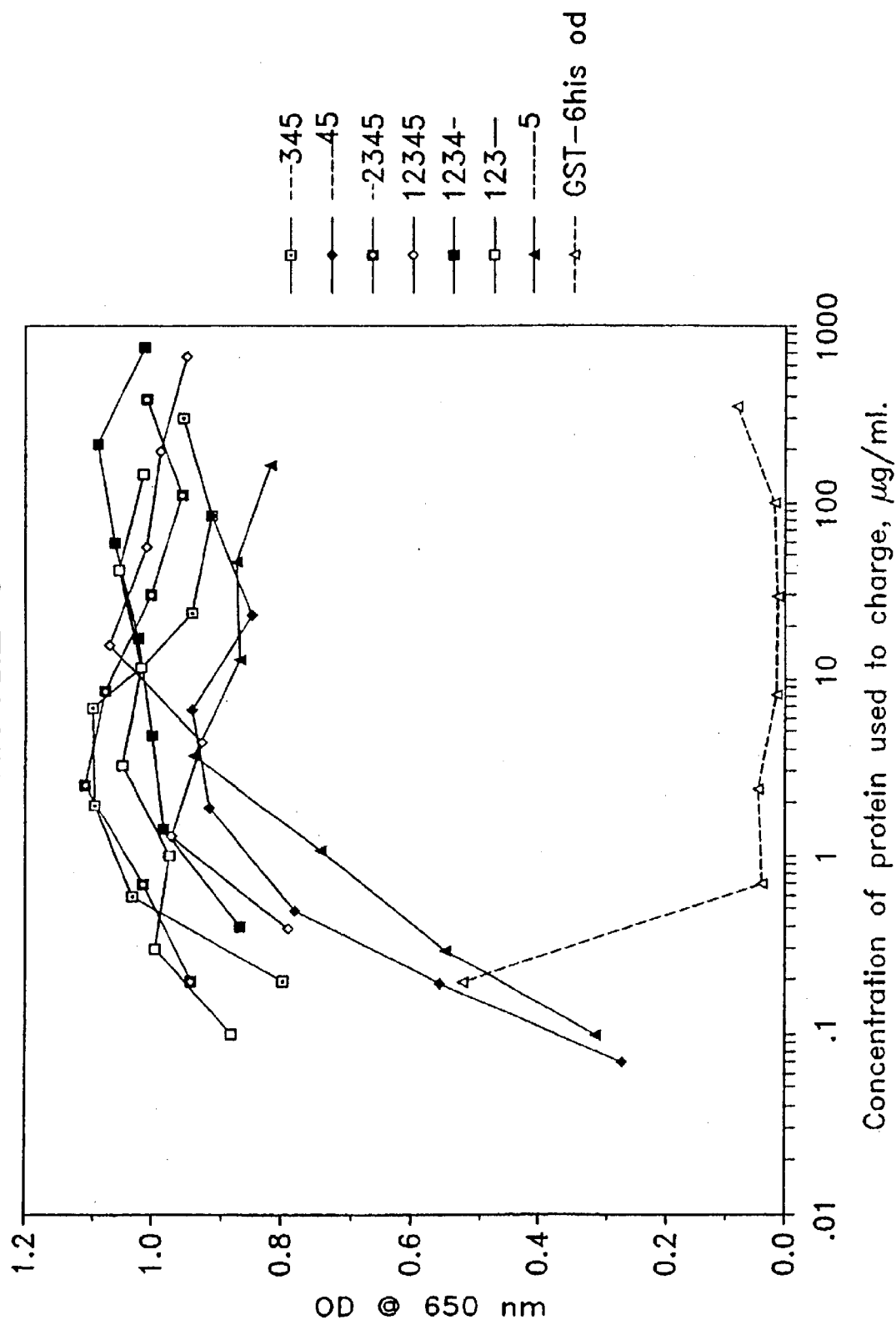
FIG. 5 is a graph depicting the results of ELISA analysis of rabbit anti-β$_2$GPI binding to various recombinant β$_2$GPI proteins. Nickel chelate coated microtiter wells were coated with the various recombinant β$_2$GPI proteins at the concentrations shown, then tested for the ability of rabbit anti-β$_2$GPI antibody to bind. Symbols represent recombinant β$_2$GPI proteins as follows: —□—, - - 345; —□—, - - - 45; —◙—, - 2345; —□—, 12345; —□—, 1234 - ; —□—, 123 - - ; —▲—, - - - - 5; and - - - □ - - - , GST-6his.
Figure 6:
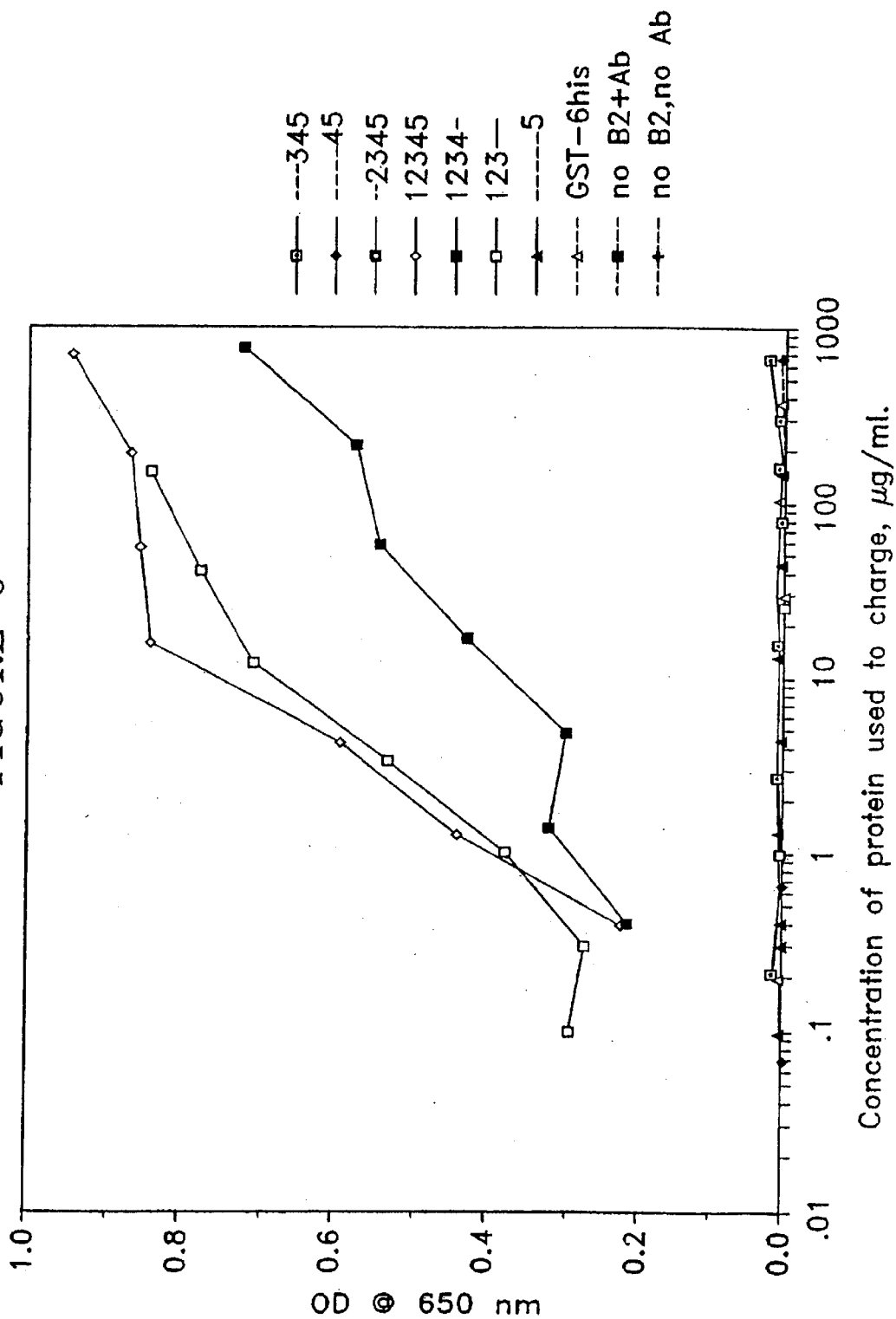
FIG. 6 is a graph depicting the results of ELISA analysis of anti-β$_2$GPI binding to various recombinant β$_2$GPI proteins. Nickel chelate coated microtiter wells were coated with the various recombinant 132GPI proteins at the concentrations shown, then tested for the ability of human anti-β$_2$GPI antibody 6701 (from patient 6701) to bind. Symbols for the recombinant β$_2$GPI are as in FIG. 5. Additional symbols are as follows: - - - ⊠ - - - , no β$_2$GPI, with antibody added; - - - + - - - , no β$_2$GPI, no antibody.

Results of Testing Direct Binding of Recombinant Mutant 62GPI Proteins by β$_2$GPI-Dependent Antiphospholipid Antibodies in the Absence of Cardiolipin Seven to nine different recombinant β$_2$GPI mutant proteins were examined to determine if they could support the direct binding of affinity purified β$_2$GPI-dependent antiphospholipid antibody preparations in the absence of anionic phospholipid. All recombinant mutant β$_2$GPI were assayed with affinity purified β$_2$GPI-dependent antiphospholipid antibody preparations from 11 different patients. Each mutant recombinant β$_2$GPI protein was tested, in a dose dependent fashion and GST-6his was included as a negative control. The recombinant mutant β$_2$GPI proteins were bound to nickel coated microtiter plates via their 6-his tail. All recombinant mutant β$_2$GPI proteins tested bound rabbit anti-β$_2$GPI showing that they were assessable by antibody (FIG. 5). The results from a typical binding experiment show that only those proteins containing domain 1 bound affinity purified β$_2$GPI-dependent antiphospholipid antibody (FIG. 6). The results from assays of all 11 affinity purified β$_2$GPI dependent antiphospholipid antibodies is summarized in Table 3. The results show that all patients' antibodies bound significantly to domain 1 containing β$_2$GPI recombinant proteins, while there was little, if any, specific binding to recombinant proteins lacking domain 1.

TABLE 3

Direct binding assays using nickel chelated wells charged with indicated recombinant
deletion-mutant $\beta_2$GPI protein versus 8 different $\beta_2$GPI-dependent
antiphospholipid antibody preparations
Maximum O.D. for each deletion-mutant:antibody combination

| Ab# | 12345 | 1---- | 12--- | 123-- | 1234- | -2345 | --345 | ---45 | ----5 |
|---|---|---|---|---|---|---|---|---|---|
| 6501 | 1.772 | 0.911 | 0.028 | 0.909 | 0.628 | 0.018 | 0.030 | 0.086 | 0.004 |
| 6626 | 1.527 | 0.560 | 0.073 | 1.250 | 0.563 | 0.008 | 0.022 | 0.086 | 0.028 |
| 6652 | 0.640 | 0.262 | ND | 0.320 | 0.135 | 0.008 | 0.016 | 0.013 | 0.012 |
| 6632 | 1.419 | 0.351 | 0.016 | 0.121 | 0.003 | 0.031 | 0.004 | 0.000 | 0.013 |
| 7008 | 1.380 | 0.195 | 0.008 | 0.360 | 0.149 | 0.019 | 0.018 | 0.030 | 0.007 |
| 6701 | 0.948 | 0.388 | ND | 0.841 | 0.715 | 0.002 | 0.002 | 0.000 | 0.000 |
| 6203 | 1.270 | 1.029 | 0.119 | 0.938 | 0.668 | 0.074 | 0.072 | 0.142 | 0.044 |
| 7015 | 1.864 | 1.102 | 0.063 | 1.160 | 0.454 | 0.114 | 0.042 | 0.167 | 0.078 |
| 6641 | 2.555 | 0.252 | — | 0.530 | 0.145 | 0.045 | 0.019 | 0.112 | 0.018 |
| 6644 | 1.848 | 0.493 | — | 1.020 | 0.768 | 0.041 | 0.048 | 0.151 | 0.017 |
| 7101 | 1.257 | 0.804 | — | 0.951 | 0.843 | 0.056 | 0.042 | 0.167 | 0.078 |
| Rabbit | 2.065 | 1.9737 | — | 1.971 | 1.708 | 1.873 | 1.993 | 1.941 | 1.663 |

Figure 7:
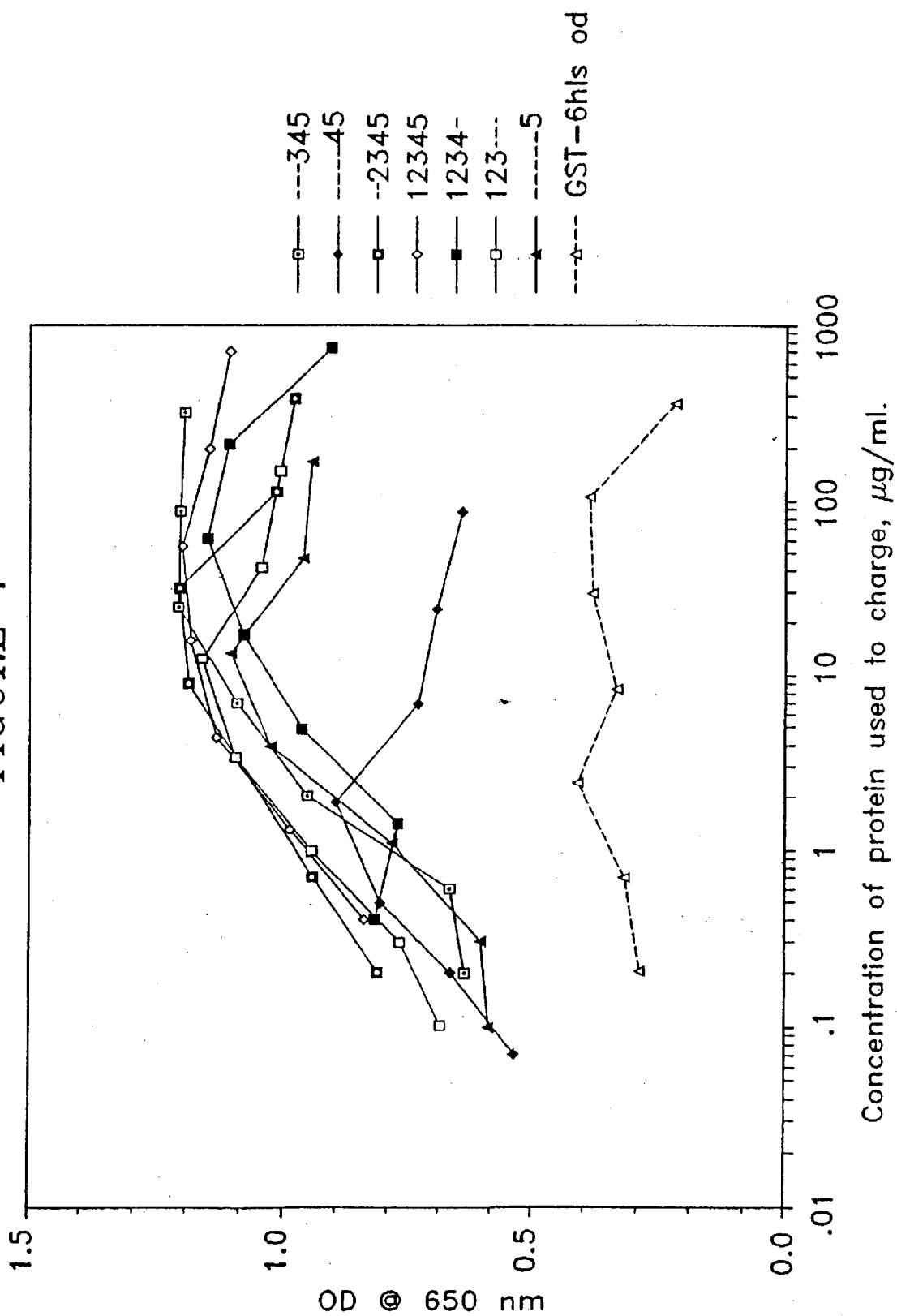
FIG. 7 is a graph depicting the results of an ELISA that measured the ability of rabbit anti-β$_2$GPI antibody to bind to various recombinant β$_2$GPI proteins which were first bound to cardiolipin (CL) coated microtiter wells. IMMULON® plates were coated with CL and then charged with the indicated concentrations of the recombinant β$_2$GPI proteins. Symbols for the recombinant β$_2$GPI are as in FIG. 5.
Figure 8:
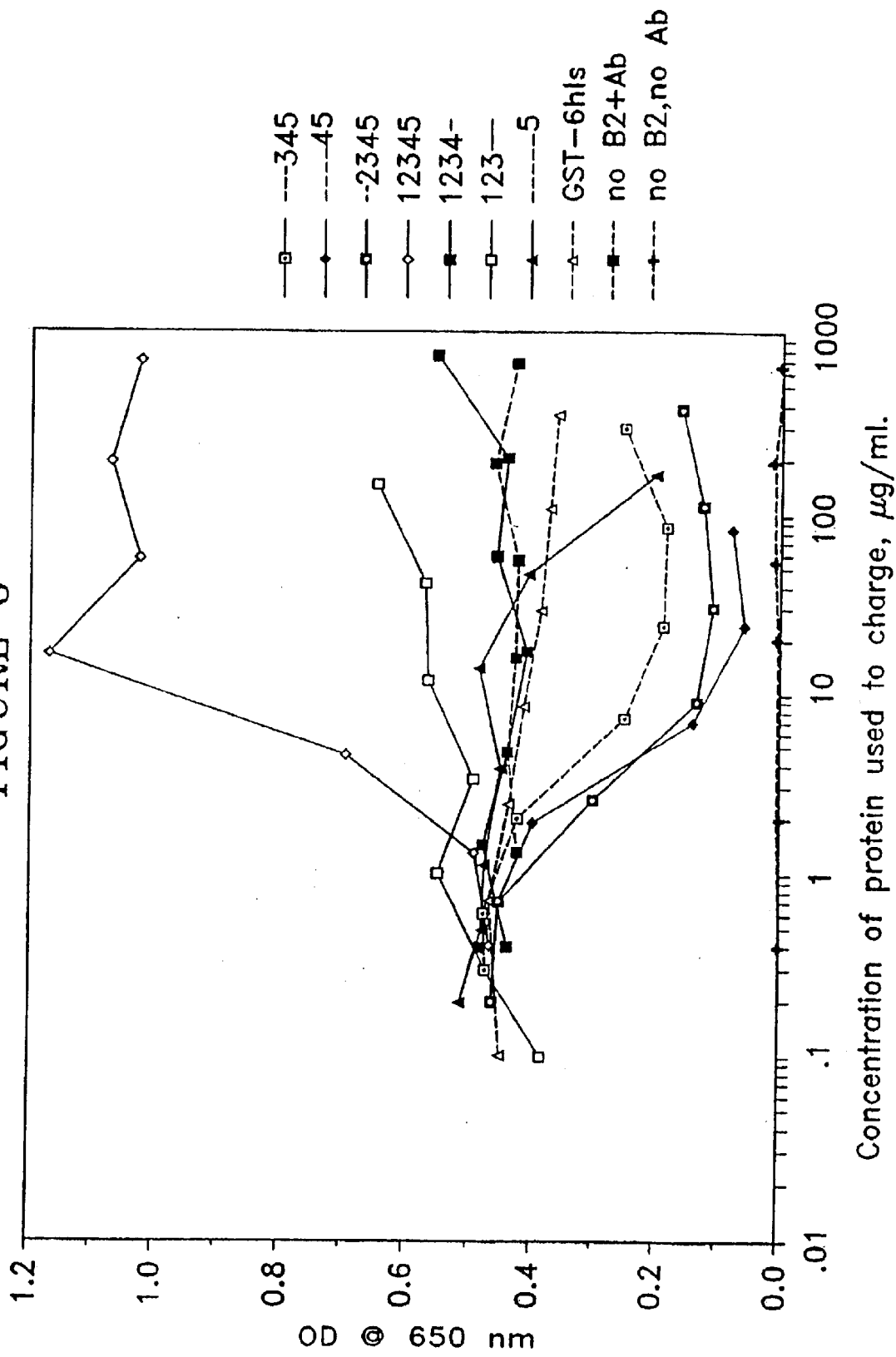
FIG. 8 is a graph depicting the results of an ELISA that measured the ability of β$_2$GPI-dependent antiphospholipid antibody preparation 6641 (from patient 6641) to bind to various recombinant β$_2$GPI proteins which were first bound to CL coated microtiter wells. IMMULON® plates were coated with CL then charged with the indicated concentrations of recombinant β$_2$GPI proteins. Symbols for the recombinant β$_2$GPI are as in FIG. 6.

Direct Binding of Recombinant Mutant $\beta_2$GPI Proteins by $\beta_2$GPI-Dependent Antiphospholipid Antibodies in the Presence of Cardiolipin Seven different recombinant $\beta_2$GPI mutant proteins were examined to determine if they could support the direct binding of affinity purified $\beta_2$GPI-dependent antiphospholipid antibody preparations in the presence of anionic phospholipid. All seven recombinant mutant $\beta_2$GPI were assayed with rabbit anti-$\beta_2$GPI and with an affinity purified $\beta_2$GPI-dependent antiphospholipid antibody preparation. Each mutant recombinant $\beta_2$GPI protein was tested, in a dose dependent fashion and GST-6his was included as a negative control. The recombinant mutant $\beta_2$GPI proteins were bound to microtiter plates that had previously been coated with cardiolipin. All seven recombinant mutant $\beta_2$GPI proteins bound rabbit anti-$\beta_2$GPI showing that they bound to cardiolipin and that they were assessable to antibody (FIG. 7). The results from a typical experiment with patient antibodies show that only those proteins containing both domain 1 and domain 5 bound affinity purified $\beta_2$GPI-dependent antiphospholipid antibody (FIG. 8).

Based on the above data in this example, we believe that under certain conditions $\beta_2$GPI is bound to solid phase supports in such a way (such as irradiated plates, cardiolipin coated plates, Nunc brand microtiter plates and nickel chelated plates in the case of the recombinant $\beta_2$GPI proteins that contain a 6-his tail) as to allow the antigenic epitope(s) on domain 1, to be freely accessible to $\beta_2$GPI-dependent antiphospholipid antibodies, but not when it is bound to other surfaces such as non-irradiated plates, many other brands of microtiter plates. These inhibition studies confirms reports by others that $\beta_2$GPI-dependent antiphospholipid can bind $\beta_2$GPI in the absence of phospholipid. Galli et al. (1990) *Lancet* 335:1544; Rouby et al (1995); Arvieux et al. (1991) *J. Immunol. Methods* 143:223. The same five recombinant mutant $\beta_2$GPI's that inhibit in the competitive inhibition assay—those that contain domain 1—are the same as those that bind $\beta_2$GPI dependent antiphospholipid antibody on the nickel chelated plates. Recombinant $\beta_2$GPI mutant proteins bound to the nickel chelated plates was confirmed by the ability of the rabbit (anti-$\beta_2$GPI to bind to all nine recombinant proteins. In contrast, only the full length recombinant $\beta_2$GPI (that is, the only recombinant protein tested that contains both domain 1 and domain 5) could be readily detected on cardiolipin coated plates. Recombinant $\beta_2$GPI mutant proteins bound to the cardiolipin coated plates was confirmed by the ability of the rabbit anti-$\beta_2$GPI to bind to all nine recombinant proteins.

Both the inhibition data (FIG. 4) and the direct binding, via nickel coated plates, data (FIG. 6) clearly show that the antigenic specificity of the 13 $\beta_2$GPI-dependent antiphospholipid antibody preparations studied are directed towards an epitope that is in domain 1 of $\beta_2$GPI.

Example 2

Specificity of Antibodies From APS Patients

Localization of the epitope binding region in the studies described in the previous Example relied on the use of affinity purified antibodies from high titer APS patients. Affinity purification of APS antibodies requires high titer patients and does not readily lend itself to studying lower titer patients or large populations of patients. Therefore, we developed an alternative approach to evaluate the antibody binding domain(s) in APS patient samples that is serum based and is amenable to evaluating a larger number of patients.

Surface plasmon resonance (SPR) provides a quantitative measurement of the interaction between immobilized protein and a soluble analyte. The current studies applied SPR to measure the interaction between immobilized $\beta_2$-GPI and domain deletion mutants of $\beta_2$-GPI with human plasma from a cohort of normal and APS patients. The studies were designed to determine if the immunodominance of $\beta_2$-GPI domain 1 could be generalized to the larger population of APS patients.

Materials and Methods

Reagents. CM5 chips, NHS and EDC and HBS-EP buffer were from BIAcore. Human haptoglobin (phenotyope 1—1), a protein containing the short consensus repeat motif found in $\beta_2$GPI, was immobilized in a separate flow cell on the chip and used as a negative control. Recombinant $\beta_2$GPI and domain-deletion mutants of $\beta_2$GPI were expressed in Tn5 cells using the baculovirus protein expression system and purified from the supernatants by nickel-chelation affinity column. Iverson et al. (1998) *Proc. Natl. Acad. Sci. USA* 95:15542–15546. Normal human plasma samples were purchased (George King Biomedical) or obtained in-house. Patient plasma samples from individuals diagnosed with either primary or secondary (to lupus) antiphospholipid antibody syndrome were obtained from a number of clinical sources.

The 55 controls used in this study were derived from a heterogenous sample. Thirty control samples (15 male; 15 female; mean age 34 yrs, range 19–45 yrs) purchased from George King Bio-Medical (Overland Park, Kans.), 5 local volunteers (3 male, 2 female), 2 pooled commercial sources and 18 blood bank donors of unknown origin were included in the analysis. The patient samples were collected from several sources and included patients with histories of venous thrombosis, arterial occlusions, cerebrovascular occlusions, multiple miscarriages and thrombocytopenia. All patients included in the study had IgG antiphospholipid antibody level (GPL) levels>20 by internal assay.

Total IgG fraction was isolated from plasma using Immunopure Plus protein G agarose beads and Immunopure IgG binding and elution buffers according to the manufacturers recommendation (Pierce).

Surface Plasmon Resonance. All experiments were performed using a BIAcore™ 2000 instrument at 25° C. with a flow rate of 10 μL/minute. Chip equilibration and binding studies were performed with degassed HBS-EP buffer, which consists of 0.01 M HEPES pH 7.4, 0.15 M NaCl, 3 mM EDTA and 0.005% (v/v) surfactant P20. Covalent coupling of protein ligands through their free amino groups to the CM5 chip was accomplished by flowing 40 μL of 0.05 M NHS/0.2M EDC over the chip to activate the chip, followed by exposure to the appropriate protein ligand. Recombinant $\beta_2$GPI(His)$_6$, domain-deletion mutants of $\beta_2$GPI and haptoglobin were immobilized by flowing 50 μL of a 25 μg/mL solution in 10 mM acetate, (pH 4.8) over the NHS-activated CM5 chip. The excess reactive groups on the chip surface are then quenched with 40 μL of 1 M ethanoloamine, (pH 8.5). Human plasma samples (130 μL) were diluted 1:1 with HBS-EP, flowed over the $\beta_2$GPI chip, and response values were collected for 780 seconds. The chips were regenerated between sample exposures with 80 μL of 0.1 M glycine-HCl (pH 2.1), 0.1 M NaCl. Since the approach to binding equilibrium was incomplete during the measurement period, the equilibrium binding value ($R_{eq}$) was determined by fitting the association curves to the following equation using the manufacturers software (BiaEvaluation version 2.2, Uppsala, Sweden)

$$R_t = R_{eq}(1-e^{-ks(t-t0)}) + R_0$$

where $R_t$ is the measured BIAcore response at time t, $R_{eq}$ is the equilibrium plateau response, t is time, $t_0$ is initial time, k, is an apparent association constant ($k_s=k_a C+k_{dis}$, where $k_a$ is the association constant, C is the analyte concentration and $k_{dis}$ is the dissociation constant), and $R_0$ is a response offset. In some experiments total IgG fractions from human plasma samples were obtained from binding to and acid elution from protein G. The plasma remaining after binding to protein G was remixed with fresh protein G beads and isolated as IgG-stripped plasma. Neutralized IgG preparations and IgG-stripped plasma diluted 1:1 with buffer were flowed over the $\beta_2$GPI chip as described above.

Results and Discussion

Recombinant human $\beta_2$-GPI-containing domains 1–5, 2–5, and domain 1 alone were cloned into bacluovirus expression vectors and expressed in TN5 cells. Aliquots of purified proteins were analyzed and quantitated by amino acid analysis. Each protein contained a single amino terminal and internal standards permitted accurate quantitation based on amino acid analysis.

The APS patient cohort was obtained from multiple centers and consisted of 106 patients with GPL≧20 that had been diagnosed with symptoms of antiphospholipid antibody syndrome (APS). Patient histories were not complete, but available histories included venous thrombosis, arterial thrombosis, cerebrovascular accidents, multiple miscarriages, premature deliveries and thrombocytopenia. GPL values ranged from 20–807 (413+161, mean±SD) with a median value of 77. The normal control population consisted of 55 samples obtained from internal donors, commercial sources or the San Diego blood bank.

Serum from APS patients and controls was diluted 1:1 in buffer and evaluated for binding to immobilized $\beta_2$-GPI (D1–5). The magnitude of the interaction with $\beta_2$-GPI (D1–5) is shown in Table 4. The mean Req for $\beta_2$-GPI (D1–5) was 730 and 328 with a median value of 635 and 201 for the 106 APS patients and 55 control patients, respectively. The difference between the patients and the control group was statistically significant (p<0.01, Student's t-test). The magnitude of the interaction of APS and control serum with $\beta_2$-GPI(D2–5) was not different between these groups (Table 4).

TABLE 4

Binding of Serum from patients

|  | Patients (GPL ≧ 20) | Controls |
|---|---|---|
| Number of subjects | 106 | 55 |
| $R_{eq}$D1-5 (mean ± sem) | 730 ± 42 | 328 ± 52 |
| $R_{eq}$D2-5 (mean ± sem) | 158 ± 36 | 160 ± 26 |
| Median $R_{eq}$D1-5 | 635 | 201 |
| Median $R_{eq}$D2-5 | 24 | 103 |
| % D1 selective | 88% | 12% |

A selectivity ratio was calculated to describe the relative binding of serum samples to $\beta_2$-GPI domain deletion mutants that differ only by the presence of domain 1. This selectivity ratio was calculated by dividing the binding ($R_{eq}$) to $\beta_2$-GPI(D1–5) by binding to $\beta_2$-GPI(D2–5). A factor of 3 or greater was arbitrarily selected to define those patients exhibiting preferential interaction with the native protein containing domain 1. The magnitude of interaction with both $\beta_2$-GPI(D1–5) and $\beta_2$-GPI(D2–5) was low in the control group and the majority of the control patients exhibited no selectivity for either immobilized protein (Table 4). In contrast, 88% of the APS patients exhibited≧3-fold selectivity for $\beta_2$-GPI containing domain 1. Forty-one percent (43/106) of the APS patients had negligible interaction with $\beta_2$-GPI(D2–5) ($Re_q$<9), resulting in very high selectivity ratios.

Serum from 10 patients with selectivity ratios 3 were further characterized to determine if the interactions observed in the serum could be attributed to the IgG fraction. The binding interactions of whole plasma, IgG stripped plasma and total IgG with $\beta_2$-GPI(D1–5) is shown in Table 5. Removing the IgG from serum with protein G removed essentially all of the specific binding interactions with the immobilized proteins. The IgG fraction was acid eluted from the protein G fraction and tested for interaction with the proteins (denoted "Total IgG" in Table 5; subsequent neutralization diluted the IgG fraction by 50% relative to the whole plasma and IgG-stripped plasma). The IgG fraction only showed interaction with $\beta_2$-GPI(D1–5) and produced responses that were similar in magnitude to the original serum interaction with $\beta_2$-GPI(D1–5) (note the dilution difference). Thus, the binding of domain 1 selective patient serum to $\beta_2$-GPI can be accounted for by the IgG fraction this assay system.

TABLE 5

BIAcore $R_{eq}$ Values for "D1-Selective" APS Patient Plasma Samples

| Patient | Whole Plasma (1:2) | | IgG-stripped Plasma (1:2) | | Total IgG (1:4) | |
|---|---|---|---|---|---|---|
| | (d2-5) | (d1-5) | (d2-5) | (d1-5) | (d2-5) | (d1-5) |
| 6501 | 333 | 1526 | 0 | 0 | 0 | 732 |
| 6701 | 199 | 952 | 0 | 0 | 0 | 460 |
| 6626 | 37 | 1622 | 0 | 49 | 0 | 1132 |
| 6515 | 259 | 1024 | 0 | 0 | 0 | 440 |
| 6207 | 19 | 1450 | 0 | 0 | 0 | 480 |
| 6642 | 8 | 811 | 0 | 48 | 0 | 480 |
| 7015 | 158 | 2092 | 0 | 0 | 0 | 864 |
| 6703 | 65 | 1001 | 0 | 0 | 0 | 556 |
| 6601 | 84 | 792 | 0 | 0 | 0 | 266 |
| 7201 | 0 | 603 | 0 | 0 | 0 | 292 |

A subgroup of the non-selective APS patients (selectivity ratio<3) were further evaluated to determine if their binding could be attributable to the IgG fraction. The results are shown in Table 6. As in the case of the domain 1 selective patients, all of the interaction with either immobilized protein could be removed by treating the serum with protein G to deplete the IgG fraction. The IgG fraction from patients appeared to reflect the binding observed in the original serum sample (Table 6).

TABLE 6

BIAcore $R_{eq}$ Values for "Non-selective" APS Patient Plasma Samples

| Patient | Whole Plasma (1:2) | | IgG-stripped Plasma (1:2) | | Total IgG (1:4) | |
|---|---|---|---|---|---|---|
| | (d2-5) | (d1-5) | (d2-5) | (d1-5) | (d2-5) | (d1-5) |
| 6117 | 386 | 324 | 0 | 0 | 79 | 120 |
| 6194 | 3197 | 2046 | 0 | 0 | 688 | 470 |
| 6649 | 553 | 758 | 0 | 0 | 127 | 253 |
| 6627 | 549 | 324 | 0 | 0 | 182 | 132 |
| 7013 | 167 | 241 | 0 | 0 | 75 | 115 |
| 6611 | 1002 | 892 | 0 | 0 | 177 | 251 |

The present study employed surface plasmon resonance to localize the antibody binding domain in a large, cross-sectional population of APS patients (n=106; GPL≧20). APS patient serum exhibited significantly greater binding to $\beta_2$-GPI than non-APS controls. In addition, the majority of patients' sera bound native $\beta_2$-GPI(D1–5) to a greater extent than a domain deletion mutant of $\beta_2$-GPI containing all domains except domain 1. Eighty eight percent of patients showed three or more fold specificity for $\beta_2$-GPI containing domain 1 relative to a domain deletion mutant that lacked domain 1. The domain 1 binding activity in APS patient serum was completely removed by depletion of the IgG component and the binding activity could be fully reconstituted in the IgG fraction. These results indicate that the immundominant binding epitopes in the majority of APS patients are localized to the amino terminal domain of $\beta_2$-GPI.

Example 3

Testing Domain 1 Fragments for Immunoreactivity to $\beta_2$GPI-Dependent Antiphospholipid Antibodies Hexapeptide Synthesis N-α-Fmoc protected amino acid attached to Wang resin was suspended twice (5 in 20% piperidine in dimethylformamide (DMF) for a total reaction time of 30 minutes to deprotect the amine. Hexapeptides with C-terminal proline were made with unprotected proline attached to chlorotrityl resin instead of Wang resin to prevent diketopiperazine formation.

The resin was rinsed two times each with DMF and methyl alcohol. A solution of N-hydroxybenzotriazole (6 equiv.), 1,3-diisopropylcarbodiimide (6 equiv.), and the second amino acid (6 equiv.) plus indicator in DMF was added to the resin. The reaction mixture was agitated for a minimum of 1.5 hours at room temperature. The resin was then rinsed two times each with DMF and methyl alcohol. The Kaiser test (2 drops 5% ninhydrin in ethyl alcohol+1 drop pyridine+1 drop 80% phenol in ethyl alcohol) was performed on a small portion of the rinsed resin to verify the absence of free amine.

The deprotection and amino acid addition steps were repeated to finish the sequence. The final amino acid was deprotected as above to yield the free amine.

The peptides were cleaved from the resin with a solution of 7.5% (by wt.) phenol, 2.5% (by vol.) ethanedithiol, 5.0% (by vol.) water, and 5.0% (by vol.) thioanisole in trifluoroacetic acid (TFA). The mixture was agitated for a minimum of three hours. The TFA was removed using vacuum and the peptide precipitated and washed twice with ether. The solid was dissolved in 1:1 acetonitrile/water for analysis. The peptides were characterized by LCMS on a 1.0×150 mm C18 (5µ, 150 Å) column (A: 0.1% TFA, 2% acetonitrile in water; B:0.08% TFA, 2% water in acetonitrile).

The acetonitrile and water were removed under vacuum or by lyophilization and the peptides were stored at 0° C.

Peptides showing activity were remade on a larger scale and purified using on a C18 column (A: 0.1% TFA in water; B: 0.08% TFA in Acetonitrile).

Competitive Inhibition ELISA

Microtiter plates (MaxiSorp™, Nalge Nunc International, Denmark) were coated with 50 pi of full length recombinant $\beta_2$GPI at 10 µg/ml in 0.1 M bicarbonate, pH 9.5, incubated overnight at 4° C., washed three times with 0.15 M PBS, pH 7.2, and blocked for one hour at room temperature with 75 µl of 2% Non-fat Dried Milk (Carnation, 2% NFDM). Test inhibitors were diluted in 2% NFDM and 25 µl of each dilution was added to coated wells. Affinity purified $\beta_2$GPI-dependent antiphospholipid antibody was diluted in 2% NFDM and 25 µl, of a constant concentration, was added to the wells, including a group of 11 wells that had no inhibitor, which acted as the positive controls. The contents of the wells were mixed and the plates were incubated at 37° C. for one hour. The plates were washed three times with PBS and 50 p! of alkaline phosphatase conjugated anti-human IgG, gamma chain specific, (Zymed #62-8422) diluted appropriately in 2% NFDM was added and incubated at 37° C. for one hour. The plates were washed three times with PBS, 50 µl of alkaline phosphatase PPMP chromogenic substrate solution was added and incubated for 30 minutes, at room temperature. The Optical Density, at 550 run, was determined by reading the plates in a microplate autoreader (Bio-Teck Instruments, model EL3 11). The percent inhibition was determined by dividing the $OD^{550}$ obtained in the presence of inhibitor by the mean $OD^{550}$ obtained from 11 wells without inhibitor and then multiplying by 100.

Inhibition Studies

Seventy four peptides were synthesized and screened in the competitive inhibition ELISA. Briefly, the 'crude' peptides, that is they were not purified, were screened at a dilution of 1:2 against three different affinity purified anti-cardiolipin antibodies. Peptides that were positive, at a dilution of 1:2, were then rescreened at further doubling dilution's. Twenty-eight peptides, that inhibited at high dilution, were re-synthesized and purified. These purified peptides were then assayed in the competitive inhibition assay. Recombinant $\beta_2$GPI was also assayed as a positive control.

Figure 9:
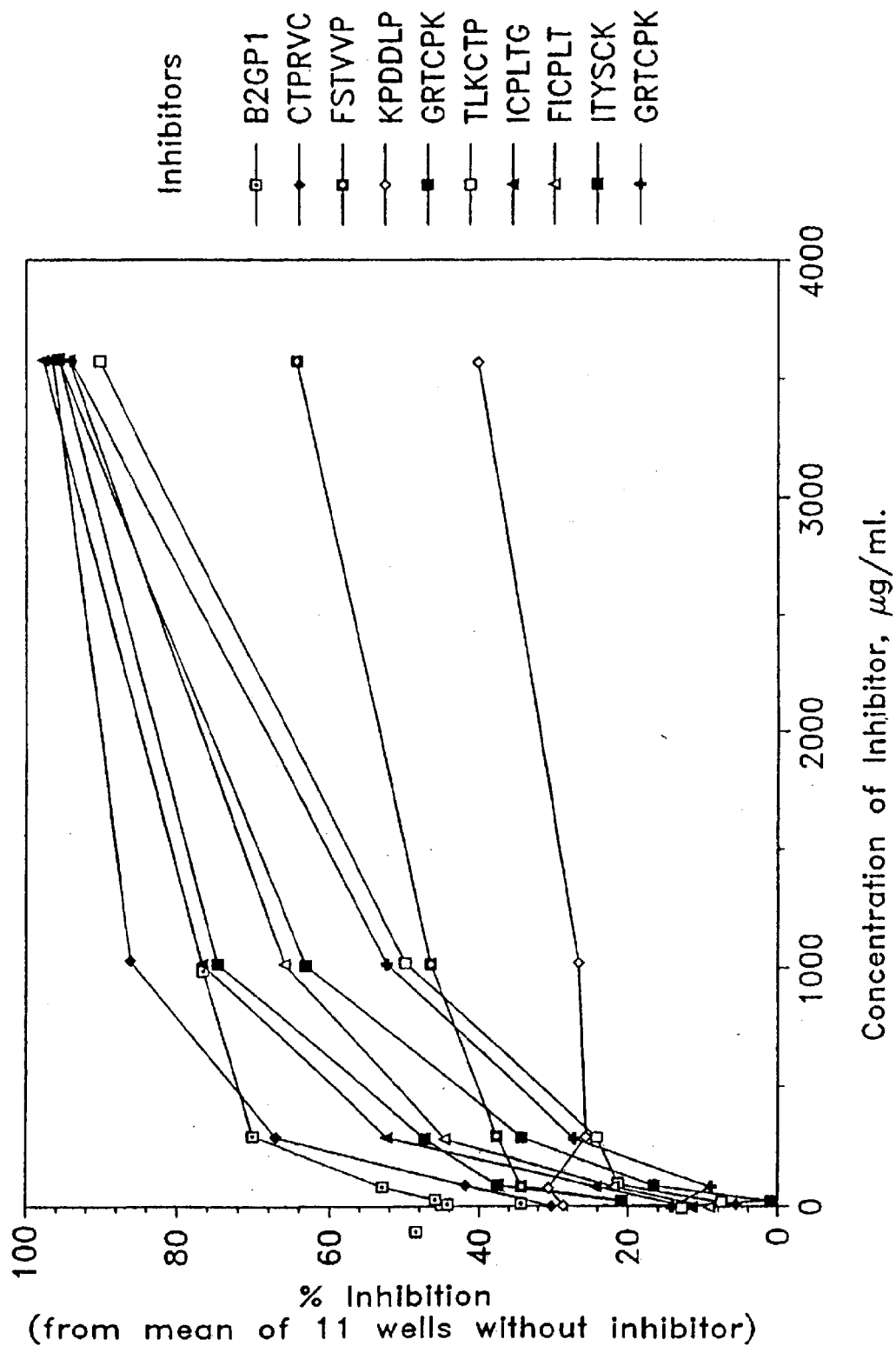
FIG. 9 is a graph depicting the results of a competitive inhibition ELISA in lid which various peptides were tested for their ability to compete with wild-type 132GPI from binding to β$_2$GPI-dependent antiphospholipid antibody. Symbols for the peptides are as follows: —□—, β$_2$GPI; —□—, CTPRVC; —◙—, FSTVVP; —□—, KPDDLP; —□—, GRTCPK; —□—, TLKCTP; —▲—, ICPLTG; —□—, FICPLT; —□—, ITYSCK; —+—, GRTCPK.

The results, shown in FIG. 9, show that some of the peptides can inhibit the binding of anti-cardiolipin antibodies from binding to $\beta_2$GPI. The majority of the peptides tested did not inhibit, thus conferring a degree of specificity to those that do inhibit. All but two of the positive peptides are clustered around the two sets of disulfide linked cysteines present in domain 1. The two peptides that are not so clustered are also the poorest at inhibiting. These disulfide linked cysteines may create structures that are recognized by $\beta_2$GPI-dependent antiphospholipid antibodies.

Example 4

Mutagenesis and Micropanning Data to Determine Critical Amino Acid Residues in Domain 1 for Binding to $\beta_2$ GPI Dependent Antiphospholipid Antibody Error-Prone PCR Error prone PCR was carried out as follows. Domain 1 of human $\beta_2$GPI was amplified by PCR under conditions that enhance the error rate of Taq polymerase. The primers were such that amino acids 1–64 were amplified. A Sfc 1 restriction site was incorporated as part of amino acid 1. At the 3' end a Sal 1 restriction site was incorporated after amino acid 64. The PCR reaction was done as described by Leung et al. (1989) *Technique* 1:11, using 0.25 mM $MnCl_2$. The PCR product was digested with Sfc 1 and Sal 1 and cloned into fd-tet-DOG2 that had been digested with Apal 1 and Sal 1. This positions domain 1 at the N-terminus of pill immediately after the pill signal sequence. The ligation reaction was electroporated in *E. coli* K91. Phage were harvested and titered by standard methods. Resulting phage clones were assayed using a micropanning technique.

Micropanning

Immulon type 2 plates were coated with protein G. Protein G was prepared at 5 $\mu$g/mL in 0.1 M $NaHCO_3$ and 100 $\mu$L per well was added to the wells of microtitration plates and incubated overnight at 4° C. After discarding excess protein G solution from plates, each well was blocked with 200 $\mu$L 2YT for 1 hour at RT with agitation on an oscillating platform. Tris-buffered saline, pH 7.4/0.5% Tween 20 (TBS/Tween), was used with an automatic plate washer to wash the wells 4 times with 200 $\mu$L. One hundred $\mu$L human $\beta_2$GPI-dependent antiphospholipid 6626, 6501, 6701, rabbit $\beta_2$GPI-dependent antiphospholipid, or control normal IgG, diluted to 2.5 $\mu$g/mL with 2YT, was added to washed wells. The plate was incubated for 1 hour at room temperature on a rotating platform.

Phage to be tested by micropanning were obtained from the agar plates generated by biopanning. Each clone to be tested was transferred using sterile toothpicks to a separate well of a round-bottom 96-well microtitration plate (Corning, Corning, N.Y.) containing 200 $\mu$L 2YT/Tet per well and cultured overnight at 30° C. Following overnight incubation, phage cultures were centrifuged using a microtitration plate holder at 1300×g for 10 minutes at room temperature. Supernatants constituted the source of "neat" phage. The neat phage were diluted 1: 100–1:1000 and 100 $\mu$L was added to the plate containing protein G-bound $\beta_2$GPI-dependent antiphospholipid antibody-6501 and normal IgG prepared as described above. The incubation of dilute phage with aPL antibody or control IgG was carried out for 2 hours at room temperature on a flat rotator. After 9 washes with TBS/Tween in an automated plate washer, the IgG-bound phage was eluted with 20 $\mu$L of 0.2 N HCl-glycine/0.1% BSA, pH 2.2. The elution incubation continued for 10 minutes at RT, during which time a new Corning microtitration plate was prepared containing 20 $\mu$L of freshly starved E. coli per well and kept chilled. One hundred forty $\mu$L of 29 mM Tris was added to the plate containing the phage eluates in order to neutralize the pH, following which 20 $\mu$L of phage suspension was transferred from each well to the corresponding well in the plate containing starved *E. coli*. After a 10 minute incubation at 37° C., 200 $\mu$L 2YT was added and incubation carried out an additional 30 minutes at 37° C. Using multichannel pipettors, 8 $\mu$L from each well was spotted on a large 2YT/Tet agar plate while retaining the original 8×12 well pattern and orientation from the last microtitration plate. After allowing the spots to dry for 30 minutes, the plate was incubated overnight at 30° C. The following day, colonies were semiquantitatively scored from 0 to 4+, with 0 symbolizing <10 colonies; 1+=10–30; 2+=30 colonies to 70% confluent; 3+=70%–90% confluent; 4+=confluent.

The results are shown in Tables 7A and 7B. For Table 7A, the rabbit anti-human $\beta_2$GPI was performed on two separate occasions. Mutations are listed with the original amino acid, the position number, and the identity of the amino acid at that position in the mutant. For example, S31F indicates that the Ser at position 31 was mutated to a Phe. Non-mutated domain 1 have a score of 3+, while domain 5 phage gave a score of –. Silent mutations are not shown. The clones begin at the N terminus and go toward the C terminus.

Table 7B represents an expansion of the mutational analysis, showing additional mutants tested against additional antibodies. The final four phage clones have mutations denoted by an asterisk, indicating that the phage have multiple mutations (3A4:D8A, S13T; 3F123: L10I, P17Q, Y22C; 3G1:R2W, S38T; 4D1:N56T, R63G).

The results indicate, inter alia (see below), that (a) the assay is consistent; (b) not all antibodies react the same; (c) different mutations at the same position can have very different effects (see Met 42, for example).

The overall results are depicted in the model of the tertiary structure of domain 1 shown in FIG. 3. It appears that amino acids 55–58 (ile, asn, leu), amino acids 40–45 (including amino acids 43–45, namely, arg, lys, phe) and amino acid 19 (lys) are important for binding to aCL antibody.

TABLE 7A

Micropans of mutant domain 1 phage

| Clone | Mutation | 6626 | 6501 | 6701 | Rabbit |
|---|---|---|---|---|---|
| | | μpan score | | | |
| 2D9 | T3P | 2 | 3 | 3 | 2 |
| A4 | D8A | 2 | 3 | 2 | 3, 3 |
| A10 | D8G | 2 | 2 | 2 | 2, 2 |
| H9 | F12L | 2 | 2 | 2 | 3 |
| D1 | T14A | 2 | 2 | 3 | 3, 3 |
| B6 | K19E | ND | 1 | 1 | 2, 3 |
| C4 | K19L | — | ND | ND | 1 |
| E3 | T20L | 2 | ND | ND | 4 |
| 2A1 | T20S | 3 | 3 | 3 | 3 |
| H1 | K33E | 3 | ND | ND | 4 |
| 2B2 | V37E | 3 | 3 | 3 | 3 |
| B11 | M42K | 3 | 3 | 3 | 3, 4 |
| 2D4 | M42T | 1 | 2 | 3 | 3 |
| A6 | M42V | ND | 2 | 2 | 3, 3 |
| C1 | R43G | 1 | ND | ND | 3 |

TABLE 7A-continued

Micropans of mutant domain 1 phage

| | | μpan score | | | |
|---|---|---|---|---|---|
| Clone | Mutation | 6626 | 6501 | 6701 | Rabbit |
| A1 | R43T | 3 | 2 | — | 2, 3 |
| 2D12 | F45L | 2 | 3 | 2 | 3 |
| C3 | F45S | — | ND | ND | 4 |
| A7 | L52Q | 3 | 3 | 3 | 3, 3 |
| 2C3 | P54S | 1 | 1 | 1 | 3 |
| D11 | N56D | — | ND | — | 2, 3 |
| B1 | N56T | 4 | 3 | — | 2, 3 |
| B2 | L58N | 1 | ND | ND | 3 |

TABLE 7

Micropans of Mutant Domain 1 Phage

| Clone | Mutation | Rabbit | Rabbit | Rabbit | Rabbit | Rabbit | 6226 | 6501 | 6701 | 6644 | 7008 | 6632 |
|---|---|---|---|---|---|---|---|---|---|---|---|---|
| 2D9 | T3P | 4 | 4 | 4 | 4 | | 4 | 4 | 4 | 4 | 4 | 3 |
| 4A6 | D8G | | | | | 4 | 2 | 2 | 2 | 3 | 2 | 2 |
| A4 | D8A | 4 | 4 | 4 | 4 | | 4 | 4 | 4 | 4 | 4 | 4 |
| 4G8 | P11L | | | | | 4 | 2 | 2 | 2 | 3 | 3 | 2 |
| H9 | F12L | 4 | 3 | 4 | 4 | | 3 | 4 | 3 | 3 | 4 | 3 |
| D1 | T14A | 3 | 4 | 4 | 4 | | 3 | 4 | 4 | 3 | 4 | 3 |
| B6 | K19E | 3 | 3 | 4 | 4 | | 1 | 1 | 1 | 2 | 0 | 0 |
| C4 | K19I | 3 | 3 | 3 | 3 | | 1 | 1 | 0 | 1 | 1 | 1 |
| SE3 | T20I | 4 | 4 | 4 | 4 | | 3 | 3 | 3 | 3 | 4 | 3 |
| 2A1 | T20S | 4 | 4 | 4 | 4 | | 4 | 4 | 4 | 4 | 4 | 4 |
| 4G1 | S31P | | | | | 4 | 2 | 2 | 2 | 2 | 2 | 2 |
| SH1 | K33E | 4 | 4 | 4 | 4 | | 4 | 4 | 4 | 4 | 4 | 4 |
| 2B2 | V37E | 4 | 4 | 4 | 4 | | 4 | 4 | 4 | 4 | 4 | 4 |
| 3B4 | S38T | | | | | 4 | 2 | 3 | 2 | 3 | 2 | 2 |
| 3E11 | G40E | | | | | 4 | 2 | 1 | 2 | 3 | 3 | 2 |
| B11 | M42K | 4 | 4 | 4 | 4 | | 4 | 4 | 4 | 4 | 4 | 4 |
| 2D4 | M42T | 4 | 4 | 4 | 4 | | 3 | 4 | 4 | 4 | 4 | 4 |
| A6 | M42V | 2 | 2 | 3 | 3 | | 1 | 2 | 2 | 2 | 3 | 2 |
| C1 | R43G | 4 | 4 | 4 | 4 | | 3 | 1 | 0 | 4 | 4 | 2 |
| A1 | R43T | 4 | 4 | 4 | 4 | | 4 | 4 | 0 | 4 | 3 | 3 |
| 3F6 | K44E | | | | | 4 | 0 | 0 | 0 | 1 | 2 | 0 |
| 2D12 | F45L | 4 | 4 | 4 | 4 | | 4 | 4 | 2 | 4 | 4 | 4 |
| SC3 | F45S | 4 | 4 | 4 | 4 | | 3 | 1 | 0 | 4 | 4 | 4 |
| 3F8 | T50A | | | | | | 2 | 2 | 2 | 3 | 3 | 2 |
| 4B12 | T50P | | | | | 4 | 1 | 1 | 1 | 1 | 1 | 1 |
| A7 | L52Q | 4 | 4 | 4 | 4 | 4 | 4 | 4 | 4 | 4 | 4 | 4 |
| 3C3 | L52P | | | | | 4 | 1 | 1 | 1 | 1 | 1 | 0 |
| 2C3 | P54S | 2 | 4 | 4 | 4 | | 2 | 2 | 2 | 3 | 3 | 3 |
| SC10 | N56D | 4 | 4 | 4 | 4 | | 3 | 3 | 3 | 3 | 4 | 3 |
| B1 | N56T | 4 | 4 | 4 | 4 | | 4 | 4 | 0 | 4 | 4 | 4 |
| 3C4 | N56- | | | | | 4 | 1 | 2 | 1 | 2 | 2 | 2 |
| B2 | L58N | 4 | 4 | 4 | 4 | | 2 | 2 | 3 | 4 | 3 | 3 |
| 3A4 | * | | | | | 4 | 3 | 3 | 3 | 4 | 3 | 3 |
| 3F12 | * | | | | | 4 | 1 | 1 | 1 | 1 | 1 | 1 |
| 3G1 | * | | | | | 4 | 1 | 1 | 1 | 1 | 1 | 1 |
| 4D1 | * | | | | | 4 | 4 | 2 | 4 | 4 | 2 | 3 |
| Dom1 | WT | 4 | 4 | 4 | 4 | 4 | 4 | 4 | 4 | 4 | 4 | 4 |
| Dom5 | WT | 4 | 4 | 4 | 4 | 0 | 0 | 0 | 0 | 0 | 0 | 0 |

Example 5

Domain 1 β₂GPI Polypeptide(s) Conjugated to Platforms

Synthesis of the Tetravalent Platform BA/PIZ/IDA/TEG (BA/PITG)

Compound 1: To a solution of 1.02 g (4.37 mmol) of N-(t-butoxycarbonyl)-iminodiacetic acid (compound 5 in U.S. Pat. No. 5,552,391, Chemically-Defined Non-Polymeric Valency Platform Molecules and Conjugates Thereof) and 1.01 g (8.75 mmol) of N-hydroxysuccinimide in 50 mL of dry THF, cooled to 0°, was added 2.26 g (10.94 mmol) of dicyclohexylcarbodiimide. The mixture was stirred for 16 h allowing to slowly warm to room temperature, and a solution of 2.22 g (10.1 mmol) of mono-CBZ-piperazine in 25 mL of THF was added to the mixture followed by 1.22 mL (887 mg, 8.75 mmol) of $Et_3N$. The mixture was stirred for 7 h at room temperature, and filtered. The filtrate was concentrated and the residue was dissolved in 125 mL of EtOAc and shaken with 2×125 mL portions of 1 N HCl, 125 mL of sat $NaHCO_3$ solution, dried ($MgSO_4$), filtered, and concentrated to give 2.39 g of a sticky solid. Purification by silica gel chromatography (95/5 $CH_2Cl_2$/MeOH) gave 1.85 g (66%) of 1.

Compound 2: To a solution of 1.74 g (2.74 mmol) of compound 1 in 10 mL of $CH_2Cl_2$ was added 10 mL of trifluoroacetic acid, and the mixture was stirred for 3 h at room temperature. The mixture was concentrated, and the residue was dissolved in 5 mL of $CH_2Cl_2$. The mixture was cooled to 0° and 100 mL of sat $NaHCO_3$ was added. The mixture was then extracted with four 100 mL portions of $CH_2Cl_2$. The $CH_2Cl_2$ layers were combined, dried ($MgSO_4$), filtered, and concentrated to give 1.46 g (99%) of 2 as a sticky hygroscopic solid which was used directly in the next step.

Compound 3: To a solution of 0.7 g (1.3 mmol) of compound 2 and 226 uL (168 mg, 1.30 mmol) of diisopropylethylamine at 0° was added a solution of 127 uL of triethyleneglycol bis-chloroformate in 4 mL of $CH_2Cl_2$, and the mixture was stirred for 3 h at room temperature. The mixture was partitioned between 80 mL of $CH_2Cl_2$ and 80 mL of 1 N HCl. The $CH_2Cl_2$ layer was washed with two 80 mL portions of water, dried ($MgSO_4$), filtered, and concentrated to give 736 mg (93%) of compound 3 as a crystalline solid.

Compound 5: Compound 3 (61 mg, 0.48 mmol) was dissolved in 3 mL of 30% HBr/HOAc and the resulting mixture was stirred at room temperature for 1 h at which time 5 mL of $Et_2O$ was added. The mixture was placed in the freezer for 1 h and centrifuged. The resulting pellet was washed with $Et_2O$ and dried to give the tetrahydrobromide salt 4 which was dissolved in 1 mL of $H_2O$. To the mixture is added 49 mg (0.58 mmol) of $NaHCO_3$ and 3 mL of dioxane. More $NaHCO_3$ is added, if needed, to make the mixture basic. The mixture is cooled to 0°, and 748 mg (2.89 mmol) of bromoacetic anhydride is added. The mixture is stirred for 2 h and partitioned between 20 mL of 1 N $H_2SO_4$ and 20 mL of 80/20 $CH_2Cl_2$/MeOH. The organic layer is dried ($Na_2SO_4$), filtered and concentrated to give crude 5 which is purified by silica gel chromatography ($CH_2Cl_2$/MeOH) to give 5.

Synthesis of AOA/PITG Tetrameric Platform and $\beta_2$GPI Domain 1 Polypeptide Conjugate Compound 44

Transamination of Domain 1 (TA/D I): Water and sodium acetate buffer were sparged with helium before use. Domain 1 (10.55 mg, 1.49 μmol) was dissolved in 0.5 mL of H20 in a polypropylene tube, and 4.0 mL of 2 M pH 5.5 NaOAc buffer was added. A solution of 3.73 mg (14.9 μmol) of $CuSO_4$ in 0.5 mL of $H_2O$ was added to the mixture, followed by a solution of 2.75 mg (29.9 μmol) of glyoxylic acid in 0.5 mL of 2 M pH 5.5 NaOAc buffer. The mixture was kept under nitrogen atmosphere and agitated gently for 18 h at which time the reaction appeared complete by analytical HPLC using a 4.6 mm×250 mm, 300 Å, 5 μm, diphenyl column (Vydac) with detection at 280 nm (1 mL/min; gradient 25%–45% B, 0–20 min, A=0.1% TFA/$H_2O$, B=0.1% TFA/$CH_3CN$). Approximate retention times are as follows: D, 13.2 min; TA/D1, 13.7 min; oxidized TA/D1, 13.4 min). The mixture was diluted to a volume of 20 mL with $H_2O$, filtered, and purified by HPLC (22.4 mm×250 mm, 300 Å, 10 μm, diphenyl column (Vydac, Hesperia, Calif.) (12 mL/min; gradient 25%40% B, 0–40 min, A=0.1%

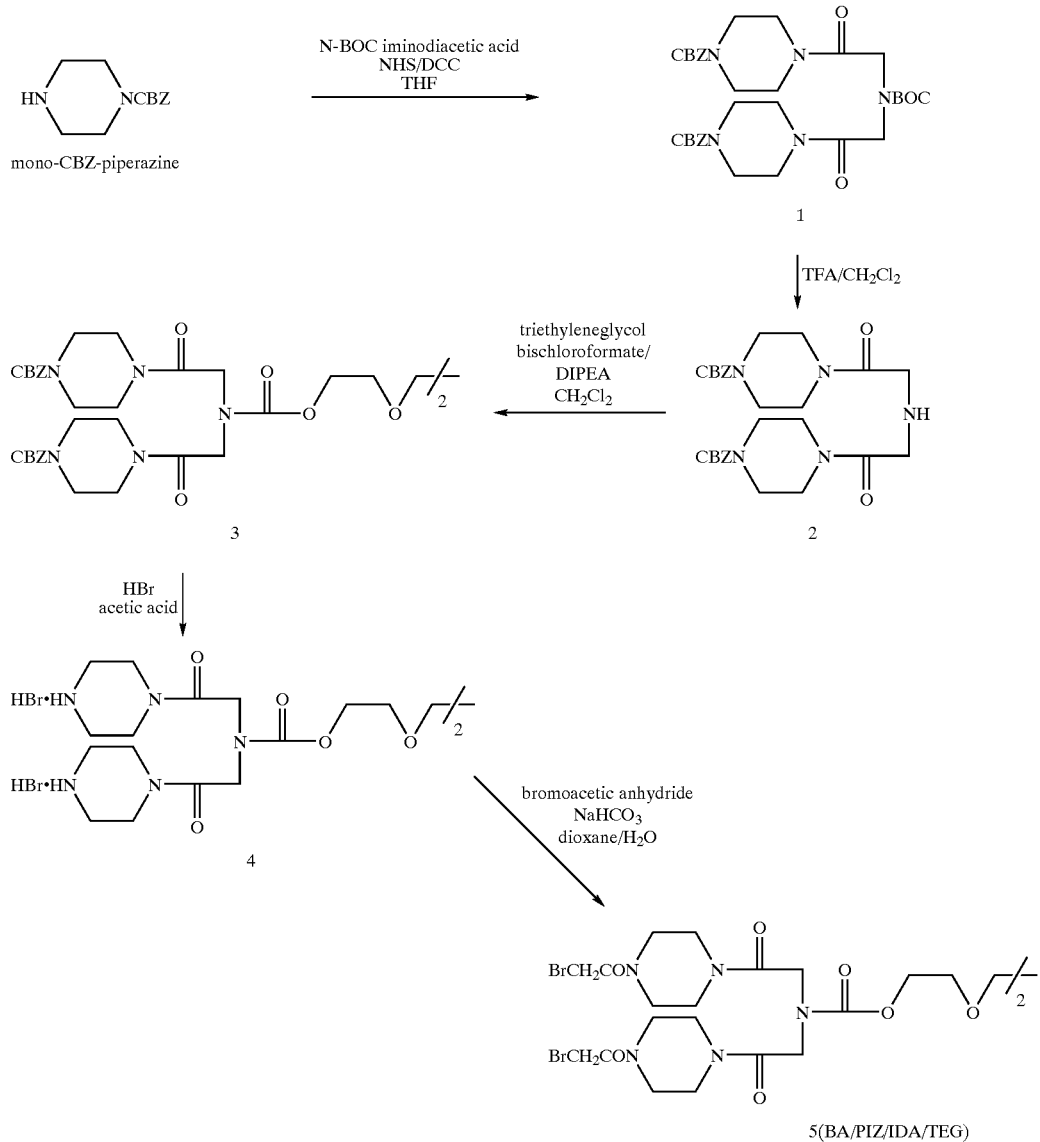

TFA/H$_2$O, B=0.1% TFA/CH$_3$CN). Fractions containing pure TA/D 1, as evidenced by analytical HPLC, were pooled and lyophilized to provide 5.0 mg (48%) of TA/D1.

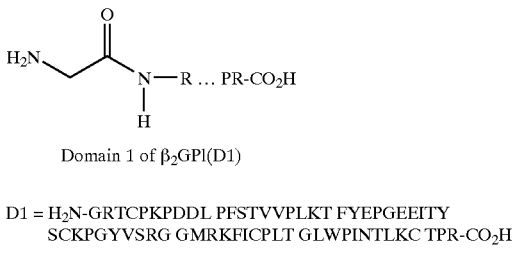

Domain 1 of β$_2$GPl(D1)

D1 = H$_2$N-GRTCPKPDDL PFSTVVPLKT FYEPGEEITY
SCKPGYVSRG GMRKFICPLT GLWPINTLKC TPR-CO$_2$H (SEQ ID NO:28)

pH 5.5
1-2 M NaOAc
CuSO$_4$
glycoxylic acid

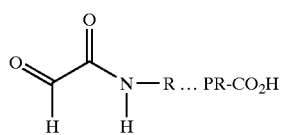

Transaminated Domain 1 (TA/D1)

TA/D1 = glyoxyl-HN-RTCPKPDDL PFSTVVPLKT FYEPGEEITY
SCKPGYVSRG GMRKFICPLT GLWPINTLKC TPR-CO$_2$H (SEQ ID NO:29)

Synthesis of Aminooxyacetyl (AOA)/PITG Platform

4-Nitrophenyl-N-(tert-butyloxycarbonyl) aminooxyacetate, 2': To a stirred solution of 1.5 g (7.85 mmol) of N-(tert-butyloxycarbonyl)aminooxyacetic acid (Aldrich Chemical Co., St. Louis, Mo.), compound 1', in 35 mL of anhydrous THF at 0° C. was added 1.09 g (7.85 mmol) of 4-nitrophenol followed by 1.62 g (7.85 mmol) of DCC. The mixture was stirred under a nitrogen atmosphere for 0.5 h at 0° C. and at room temperature for 18 h. The mixture was filtered to remove dicyclohexylurea, and the filtrate was concentrated and purified by silica gel chromatography (95/5 CHCl$_3$/isopropyl alcohol) to give 2.30 g (94%) of compound 2' as a white solid: $^1$H NMR (CDCl$_3$) δ 1.51 (s, 9H), 4.73 (s, 2H), 7.36 (d, 2H), 7.73 (s, 1H), 8.32 (d, 2H).

Synthesis of BOC-protected AOA/PITG Platform, 4': Compound 3 (300 mg, 0.235 mmol,) was treated with 1.5 mL of a 30% solution of HBr in acetic acid for 30 min. The HBr salt of the resulting tetra-amine was precipitated by addition of diethyl ether. The mixture was centrifuged, and the supernatant was removed and discarded. The remaining solid was washed with ether, dried under vacuum, and dissolved in 9 mL of DMF. To the resulting mixture was added 294 μL (1.69 mmol) of diisopropylethylamine followed by a solution of 410 mg (1.31 mmol) of compound 2 in 3 mL of DMF. The mixture was stirred under nitrogen atmosphere for 4 h and partitioned between 15/1 CHCl$_3$/MeOH and brine. The aqueous layer was washed twice with 15/1 CHCl$_3$/MeOH, and the combined organic layers were dried (Na$_2$SO$_4$) and concentrated to give 680 mg of an oil. Purification by silica gel chromatography (step gradient 95/5 to 75/25 CHCl$_3$/MeOH) gave 215 mg (65%) of compound 4' as a white solid: $^1$H NMR (CDCl$_3$) δ 1.49 (s, 36H), 3.40–3.73 (m, 40H), 4.24(m, 12H), 4.59 (overlapping singlets, 8H), 8.21 (s, 2H), 8.32 (s, 2H).

AOA/PITG Platform, Compound 5': HCl gas was bubbled through a stirred solution of 67 mg (0.047 mmol) of compound 4' in 10/1/1 EtOAc/CHCl$_3$/MeOH for 15 min, and the mixture was stirred for an additional 15 min. The mixture was concentrated under vacuum and kept under vacuum for 16 h to provide 43 mg (78%) of compound 5' as a white solid: $^1$H NMR (DMSO) δ 3.33–3.67 (m, 40H), 4.08 (m, 4H), 4.18 (s, 8H), 4.90 (s, 8H); mass spectrum (ES) m/z calculated for C$_{40}$H$_{69}$N$_{14}$O$_{18}$: 1033. Found: 1033.

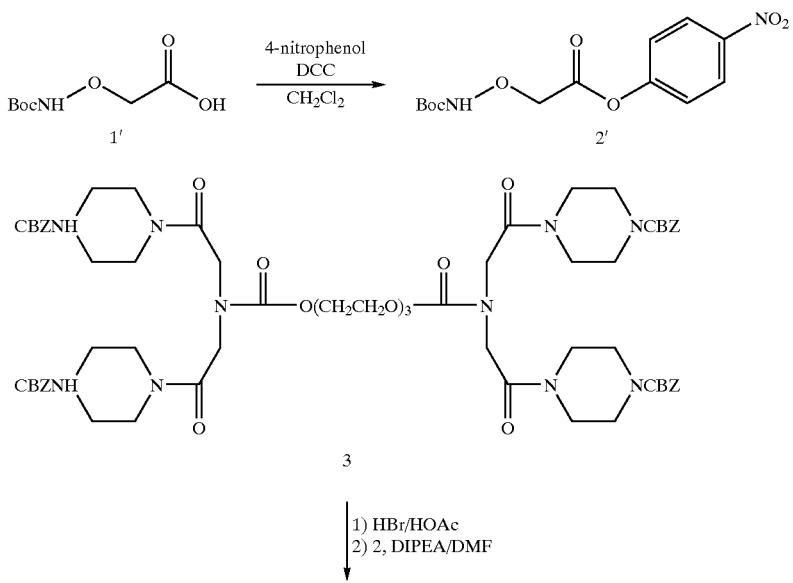

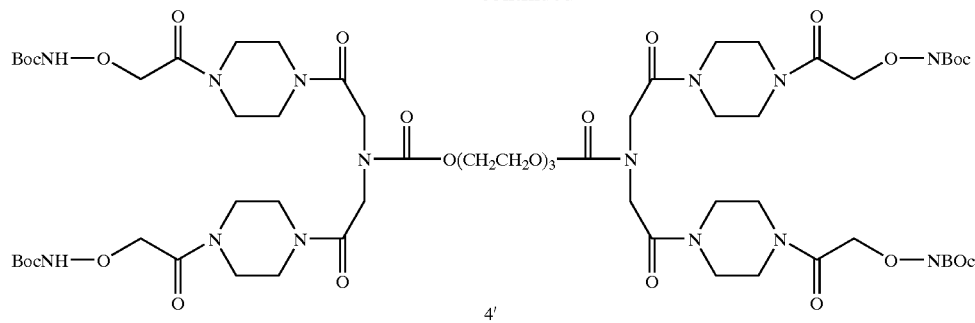

4'

| HCl/EtOAc

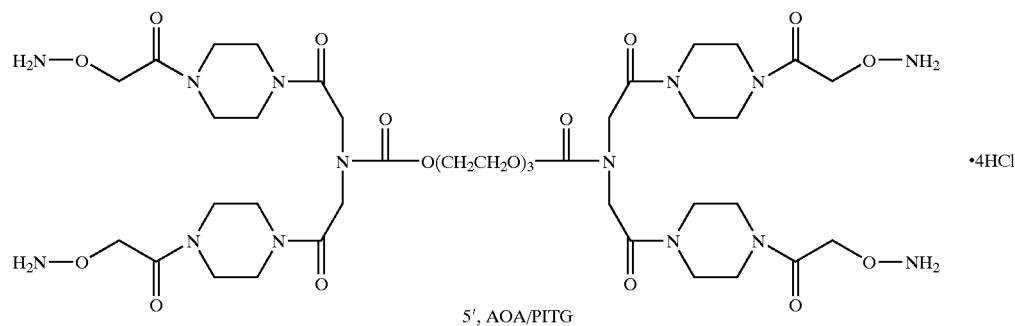

5', AOA/PITG

Synthesis of Tetravalent D1 Conjugate Compound 44: TA/D1 (0.90 mg, $1.28 \times 10^{-7}$ mol) was dissolved in 250 μL of 0.1 M sodium acetate pH 4.60 buffer in a polypropylene tube. To the mixture was added 16.6 μL (18.9 μg, $1.60 \times 10^{-8}$ mol) of a 0.97 μmol/mL solution of AOA/PITG platform, compound 5', in 0.1 M sodium acetate pH 4.60 buffer. The mixture was agitated gently under nitrogen for 6 days at which time the reaction appeared to be complete by analytical HPLC using a 4.6 mm×250 mm, 300 Å, 5 μm, diphenyl column (Vydac) with detection at 280 nm (1 mL/min; gradient 25%–45% B, 0–20 min, A=0.1% TFA/$H_2O$, B=0.1% TFA/$CH_3CN$). Approximate retention times are as follows: TA/D1, 13.7 min; compound 44, 17.2 min). The mixture was diluted with 95/5 water/acetonitrile to a volume of 1 mL and purified by HPLC (10 mm×250 mm, 300 Å, 5 μm, diphenyl column (Vydac) (3 mL/min; gradient 25%–45% B, 0–40 min, A=0.1% TFA/$H_2O$, B=0.1% TFA/$CH_3CN$). Fractions containing pure conjugate compound 44, as evidenced by analytical HPLC, were pooled and lyophilized to provide 0.4 mg (25%) of compound 44: mass spectrum (ES, average m/z) calculated for $C_{1320}H_{2032}N_{338}O_{370}S_{20}$: 29,198. Found: 29,218.

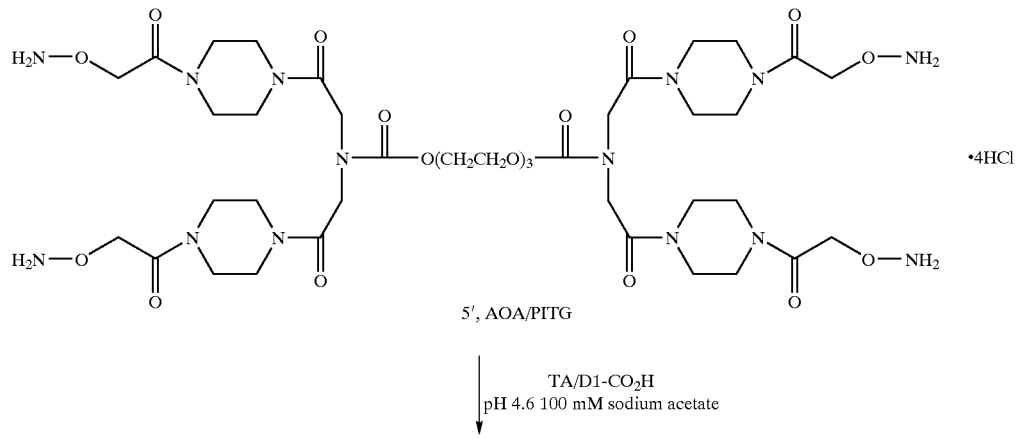

5', AOA/PITG

| TA/D1-$CO_2H$
| pH 4.6 100 mM sodium acetate

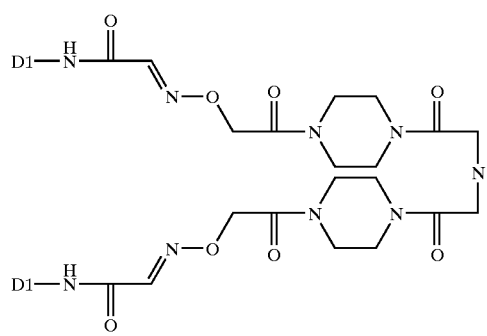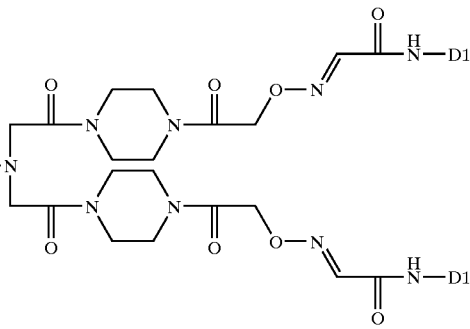
44
Synthesis of Tetrameric AOTEG/DEA/DEG Platform and β₂GPI Domain 1 Polypeptide Conjug give an orange oil. Purification by silica gel chromatography (step gradient, 10/90 EtOAc/hexanes to 15/85 EtOAc/hexanes) to provide 17.8 g (90%) of an orange oil: $^1$H NMR (CDCl$_3$) δ 3.28 (t, 4H), 3.67 (s, 4H), 3.78 (t, 4H); $^{13}$C NMR (CDCl$_3$) δ 3.6, 70.5, 72.2.

Compound 13: DBU (284 µL, 290 mg, 1.90 mol) was added to a mixture of 266 mg (2.0 mmol) of N-(tert-butyloxycarbonyl)hydroxylamine (Aldrich Chemical Co.) and 2.96 g (8.0 mmol) of compound 12, and the mixture was capped and shaken until homogeneous. After 15 minutes the mixture solidified, and it was allowed to stand for 45 minutes. To the mixture was added 5 mL of CH$_2$Cl$_2$, and the mixture was shaken again to dissolve solids. The resulting solution was added to 200 mL of EtOAc. An additional 50 mL of EtOAc was added, and the mixture was filtered to remove solids. The filtrate was concentrated to give an oil which was partitioned between 100 mL of EtOAc and 3×50 mL of 1 N HCl solution. The EtOAc layer was washed with 2×50 mL of 1 N NaOH followed by 2×50 mL of 5% sodium bisulfite solution and concentrated to provide 2.6 g of yellow oil. Purification by silica gel chromatography (step gradient, 20/80 to 45/55 EtOAc/hexanes) gave 515 mg (69%) of compound 13 as a yellow oil: $^1$H NMR(CDCl$_3$) δ 1.50 (s, 9H), 3.28 (t, 2H), 3.68 (s, 4H), 3.72 (m, 4H), 4.02 (t, 2H), 7.72 (s, 1H); $^{13}$C NMR (CDCl$_3$) δ 2.9, 28.3, 68.9, 69.4, 70.2, 70.6, 72.0, 75.4, 81.6, 156.9.

Diethyleneglycol bis-4-nitrophenylcarbonate, Compound 60: Pyridine (30.5 mL, 377 mmol) was slowly added to a 0° C. solution of 5.0 g (47.11 mmol) of diethylene glycol and 23.74 g (118 mmol) of 4-nitrophenylchloroformate in 500 mL of THF. The cooling bath was removed, and the mixture was stirred for 18 hours at room temperature. The mixture was cooled back to 0° C., acidified with 6 N HCl, and partitioned between 400 mL of 1 N HCl and 2×400 mL of CH$_2$Cl$_2$. The combined organic layers were dried (MgSO$_4$), filtered, and concentrated to give 24.3 g of a white solid. Crystallization from hexanes/EtOAc gave 16.0 g (78%) of compound 37 as a white powder: mp 110° C.; $^1$H NMR (CDCl$_3$) δ 3.89 (t, 4H), 4.50 (t, 4H), 7.40 (d, 4H), 8.26 (d, 4H).

Compound 61: A solution of 2.5 g (5.73 mmol) of compound 37 in 17 mL of pyridine was added to a 0° C. solution of 1.8 g (17.2 mmol) of diethanolamine in 3 mL of pyridine. The cooling bath was removed, and the mixture was stirred for 5 hours at room temperature to yield compound 38, which was not isolated but was used as is in the next step.

Compound 14: The mixture from the previous step was cooled back to 0° C., 40 mL of CH$_2$Cl$_2$ was added followed by a solution of 11.55 g (57.3 mmol) of 4-nitrophenylchloroformate in 60 mL of CH$_2$Cl$_2$, and the mixture was stirred for 20 hours at room temperature. The mixture was cooled back to 0° C., acidified with 1 N HCl, and partitioned between 300 mL of 1 N HCl and 2×200 mL of CH$_2$Cl$_2$. The combined organic layers were dried (MgSO$_4$), filtered, and concentrated to give 13.6 g of yellow solid. Purification by silica gel chromatography (CH$_2$Cl$_2$/MeOH and EtOAc/hexanes) provided 4.91 g (83%) of compound 39 as a sticky amorphous solid: $^1$H NMR (CDCl$_3$) δ 3.72 (m, 12H), 4.31 (t, 4H), 4.48 (m, 8H), 7.40 (m, 8H), 8.29 (m, 8H).

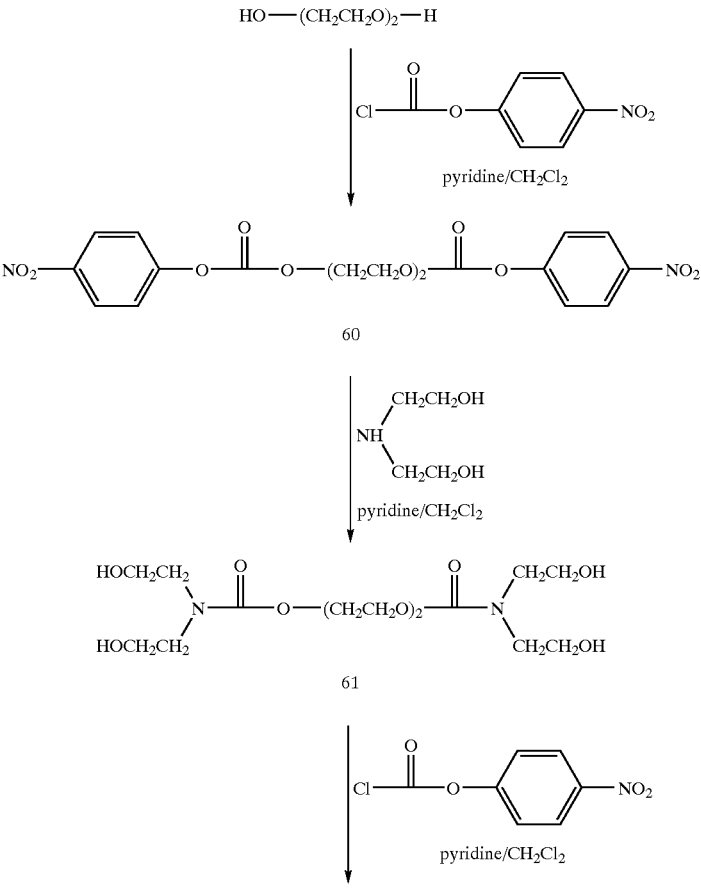

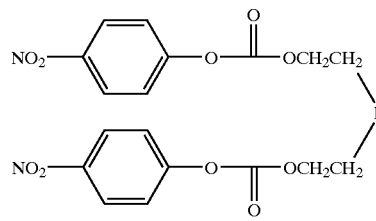 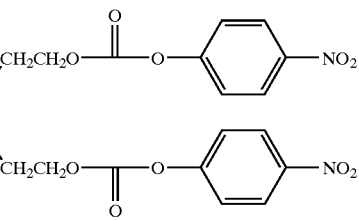

14

BOC-Protected AOTEG/DEA/DEG Platform, Compound 15: Triethylamine (157 μL, 114 mg, 1.13 mmol) added to a stirred solution of 193 mg (0.188 mmol) of compound 14 (prepared as described above and in U.S. Serial No. 60/111,641, filed Dec. 9, 1998) followed by 298 mg (1.13 mmol) of compound 11. The mixture was allowed to come to room temperature and was stirred overnight. The mixture was cooled to 0° C., acidified with 1 N HCl, and partitioned between 20 mL of 1 N HCl and 4×20 mL of $CH_2Cl_2$. The combined organic layers were washed with saturated $NaHCO_3$ solution, dried ($MgSO_4$), filtered, and concentrated to give 279 mg of yellow oil. Purification by silica gel chromatography (97/3 $CH_2Cl_2$/MeOH) provided 138 mg (48%) of 15 as an oil: $^1$H NMR ($CDCl_3$) δ 1.49 (s, 36H), 3.35 (m, 8H), 3.46–3.78 (m, 44H), 4.04 (t, 8H), 4.21 (m, 12H), 5.80 (m, 4H), 7.91 (s, 4H); mass spectrum (ES) m/z calculated for $C_{62}H_{117}N_{10}O_{33}$ (M+H)$^+$: 1528.8. Found: 1528.5.

Compound 16: Compound 15 (60 mg, 39.2 μmol) was dissolved in 10 mL of ⅑ trifluoroacetic acid/$CH_2Cl_2$, and the mixture was kept at room temperature for 3 h. Gentle stream of nitrogen was used to evaporate the solvent, and the residue was dissolved in a minimal amount of chromatography solvent (5/7.5/87.5 con $NH_4OH/H_2O/CH_3CN$) which was used to load the mixture onto a silica gel column. Purification by silica gel chromatography (step gradient, 5/7.5/87.5 to May 10, 1985 con $NH_4OH/H_2O/CH_3CN$) provided 36 mg (82%) of 16 as a colorless oil: $^1$H NMR ($CDCl_3$) δ 3.37 (m, 8H), 3.58 (m, 16H), 3.67 (s, 16H), 3.71 (m, 12H), 3.86 (m, 8H), 4.17–4.29 (m, 12H), 4.93 (brd, 8H), 5.91 (m, 4H); $^{13}$C NMR ($CDCl_3$) δ 40.9, 47.7, 48.2, 62.9, 64.7, 69.4, 69.6, 70.2, 70.3, 70.5, 74.8, 156.1, 156.6; mass spectrum (ES) m/z calculated for $C_{42}H_{85}N_{10}O_{25}$ (M+H): 1129. Found: 1129.

For the purpose of checking purity by analytical HPLC, the tetra-acetone oxime was prepared as follows. Compound 16 (0.38 mg, 0.34 μmol) was dissolved in 240 μL of 0.1 M NaOAc buffer in an HPLC sample vial. To the solution was added 10 μL of a solution of 49 μL of acetone in 2.0 mL of 0.1 M NaOAc buffer. The mixture was allowed to stand for 1 h and an aliquot was analyzed by HPLC (4.6 mm $C_{18}$ column, 1 mL/min, 210 nm detection, gradient, 10–60% B over 20 min, A=0.1% TFA/$H_2O$, B=0.1% TFA/$CH_3CN$, $t_R$=19 min); mass spectrum of collected eluent (ES) m/z calculated for $C_{54}H_{101}N_{10}O_{25}$ (M+H): 1289. Found: 1289.

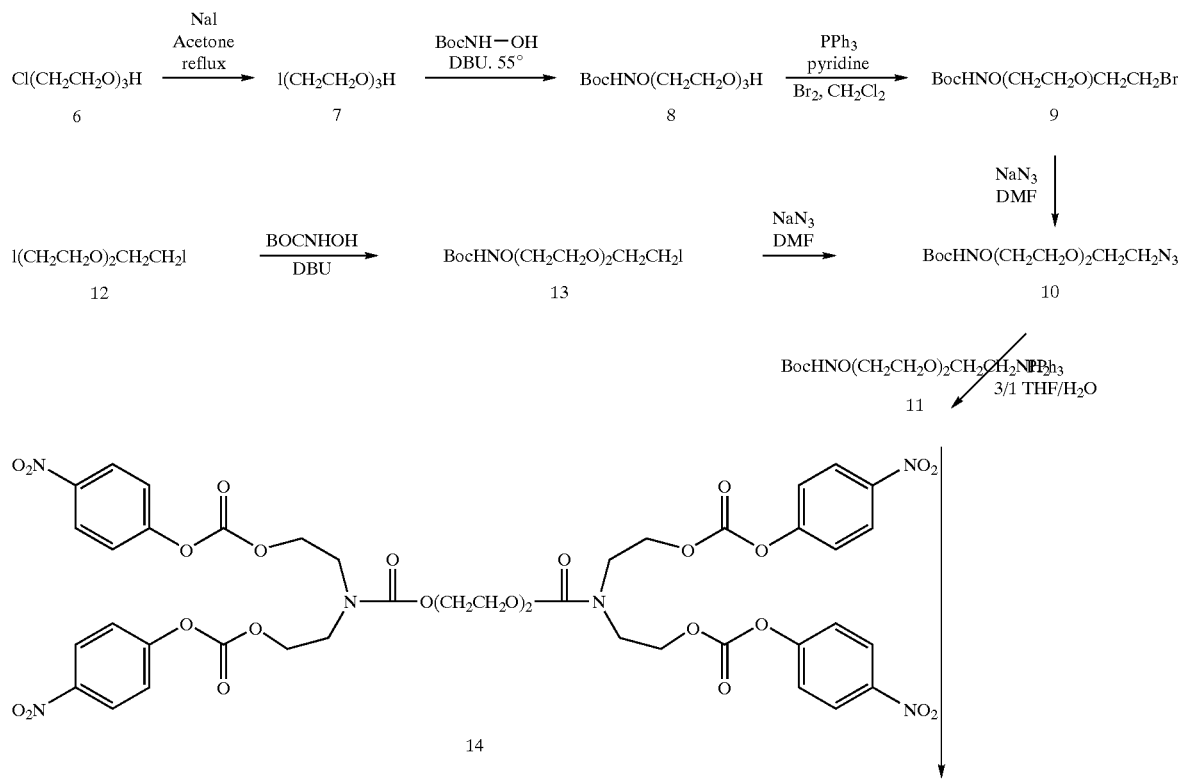

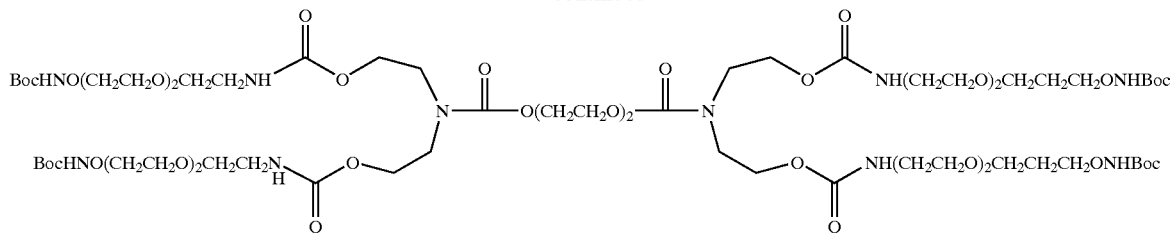

15

↓ 10% TFA/CH$_2$Cl$_2$

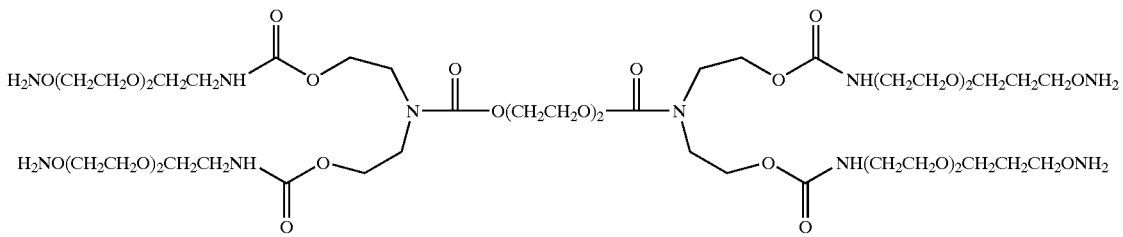

16

Synthesis of Tetravalent D1 Conjugate Compound 45: TA/D1 (5.20 mg, 7.37×10$^{-7}$ mol) was dissolved in 2.0 mL of He sparged 0.1 M sodium acetate pH 4.60 buffer in a polypropylene tube. To the mixture was added 15.07 μL (139 μg, 1.23×10$^{-7}$ mol) of a 8.147 μmol/mL solution of AOTEG/DEA/DEG platform, compound 16, in 0.1 M sodium acetate pH 4.60 buffer. The mixture was agitated gently under nitrogen for 23 hours at which time the reaction appeared to be complete by analytical HPLC using a 4.6 mm×250 mm, 300 Å, 5 μm, diphenyl column (Vydac) with detection at 280 nm (1 mL/min; gradient 25%–45% B, 0–20 min, A=0.1% TFA/H$_2$O, B=0.1% TFA/CH$_3$CN). Approximate retention times are as follows: TA/D1, 13.7 min; conjugate compound 45, 17.2 min). The mixture was diluted with water to a volume of 5 mL and purified by HPLC (10 mm×250 mm, 300 Å, 5 μm, TFA/H$_2$O, B 0.1% TFA/CH$_3$CN). Fractions containing pure conjugate compound 45, as evidenced by analytical HPLC, were pooled and lyophilized to provide 1.73 mg (48%) of conjugate compound 45: mass spectrum (ES, average m/z) calculated for C$_{1322}$H$_{2048}$N$_{334}$O$_{377}$S$_{20}$: 29,294. Found: 29,294.

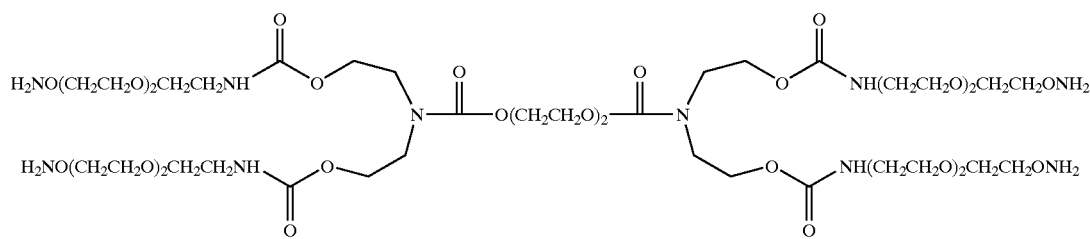

Compound 16, AOTEG/DEA/DEG Platform

↓ TA/D1-CO$_2$H
pH 4.6 100 mM sodium acetate

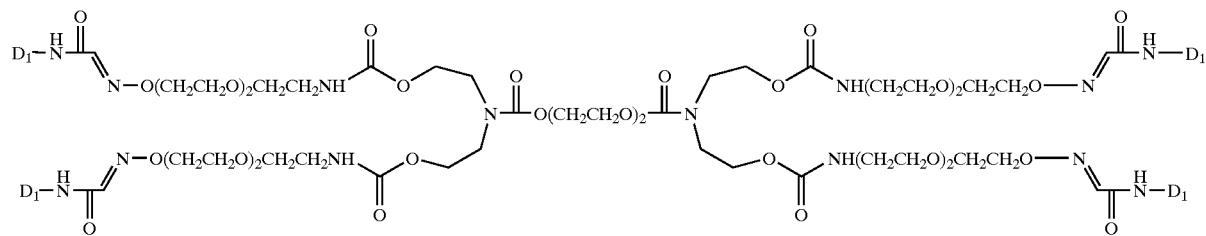

45

Preparation of Tetravalent D1 Conjugate via Alkylation of Fifth-Cys with an Alkylhalide Platform, Compound 65: Domain 1 has four cysteines which are in oxidized form, and properly folded domain 1 has two disulfide bonds. A fifth cysteine can be included at any position at the N-terminus or C-terminus outside of the native cysteines. In this example a fifth cysteine is included which is native to the second domain of $\beta_2$GPI. A fifth cysteine can be used, by virtue of its free sulfhydryl group, to react with a platform designed to react with sulfhydryl groups. One such platform is a haloacetyl platform such as compound 23.

Fifth-Cys D1 (four equivalents) is dissolved in helium sparged 100 mM pH 8.0 sodium borate buffer. The solution is kept under nitrogen atmosphere, and a solution of bromoacetylated platform, compound 23 (one equivalent), is added. The mixture is stirred until the reaction is complete, and purification of the mixture by preparative HPLC provides tetravalent conjugate, compound 65.

mixture was cooled to 0° C. and acidified with IN aqueous HCl. The resulting mixture was partitioned between 100 mL of 1 N aqueous HCl and 3×100 mL of $CH_2Cl_2$. The combined organic layers were dried ($MgSO_4$), filtered, and concentrated to give 1.05 g of a sticky solid. Purification by silica gel chromatography (6/4 hexanes/EtOAc) gave 505 mg (62%) of compound 17 as a slightly yellow oil: $^1$H NMR ($CDCl_3$) δ 1.47 (s, 9H), 3.67–3.78 (m, 6H), 3.80 (m, 2H), 4.02 (m, 2H), 4.48 (m, 2H), 7.40 (d, 2H), 7.50 (s, 1H), 8.29 (d, 2H); mass spectrum (ES) m/z calculated for $C_{18}H_{26}N_2O_{10}Na$ (M+Na): 453.1. Found: 453.0.

BOC-protected AOTEG/PIZ/DEA/DEG platform, compound 19: To a solution of compound 18 (prepared as described in U.S. Serial No. 60/111,641, filed Dec. 9, 1998) in a mixture of aqueous sodium bicarbonate and dioxane is added a solution of four equivalents of compound 17 in dioxane. Upon completion of the reaction, the mixture is partitioned between water and $CH_2Cl_2$. The $CH_2Cl_2$ layer is 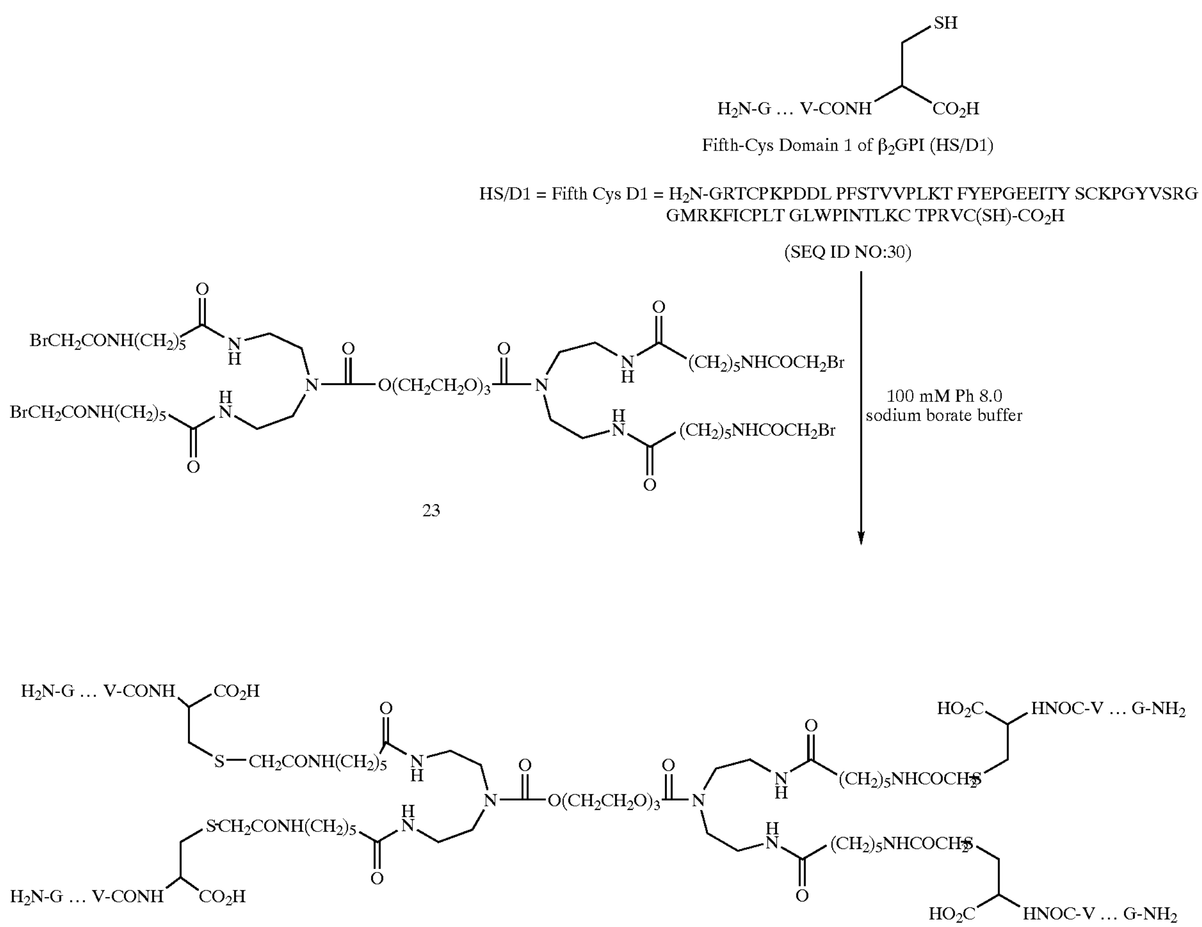 Fifth-Cys Domain 1 of $\beta_2$GPI (HS/D1)

HS/D1 = Fifth Cys D1 = $H_2$N-GRTCPKPDDL PFSTVVPLKT FYEPGEEITY SCKPGYVSRG GMRKFICPLT GLWPINTLKC TPRVC(SH)-$CO_2$H (SEQ ID NO:30)

23

65

Synthesis of AOTEG/PIZ/DEA/DEG Platform, Compound 17: Pyridine (610 μL, 596 mg, 7.54 mmol) was added slowly to a stirred solution of 500 mg (1.88 mmol) of compound 8 and 760 mg (3.77 mmol) of p-nitrophenylchloroformate in 14 mL of $CH_2Cl_2$, and the mixture was stirred at room temperature for 18 hours. The concentrated, dried, and purified by silica gel chromatography to provide compound 19.

AOTEG/PIZ/DEA/DEG platform, compound 20: The BOC-protecting groups are removed from compound 19 in a manner essentially similar to that described for the preparation of compound 16 to provide compound 20.

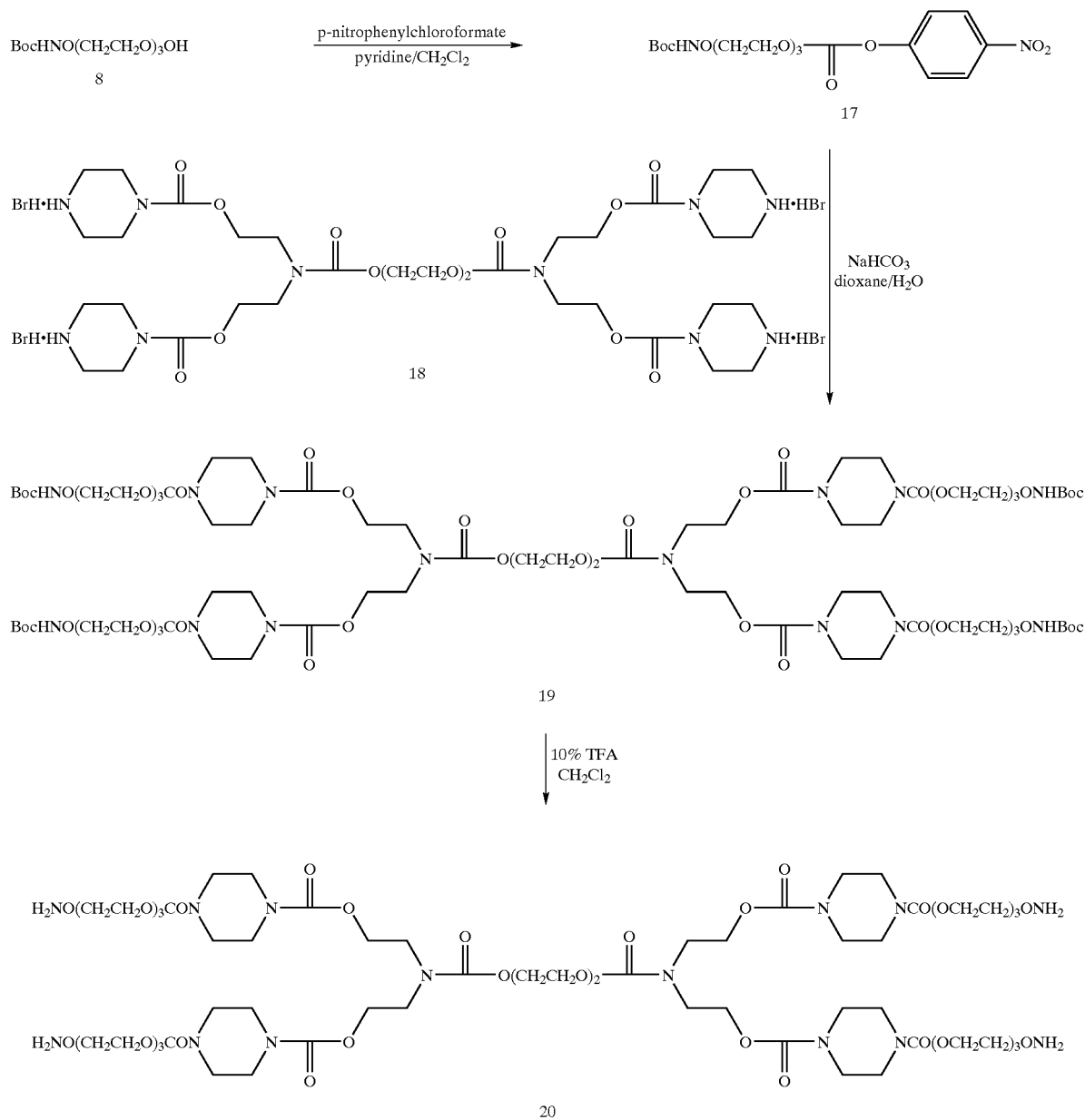

Synthesis of AOTEG/SA/AHAB/TEG Platform, S-acetyl-2-[2-(2-N-tert-butyloxycarbonylaminooxyethyoxy)ethoxy]-ethylmercaptan, Compound 21a: To a solution of 500 mg (1.52 mmol) of compound 9a in 30 mL of acetone was added 191 mg (1.68 mmol) of potassium thioacetate (Aldrich Chemical Co.). The mixture was stirred at room temperature for 18 hours, and the resulting precipitate was removed by filtration. The filtrate was concentrated and partitioned between 300 mL of EtOAc and 2×80 mL of brine. The EtOAc layer was dried (NaSO$_4$), filtered, and concentrated to give 460 mg (93%) of compound 21a as a light brown oil: $^1$H NMR (CDCl$_3$) δ 1.48 (s, 9H), 2.35 (s, 3H), 3.12 (t, 2H), 3.61 (t, 2H), 3.64 (m, 4H), 3.73 (m, 2H), 4.02 (m, 2H), 5.52 (s, 1H); $^{13}$C NMR (CDCl$_3$) δ 28.3, 28.8, 30.6, 69.3, 69.8, 70.2, 70.5, 75.3, 81.5, 156.8, 195.3.

2-[2-(2-N-tert-butyloxycarbonylaminooxyethyoxy)ethoxy]ethylmercaptan, Compound 22a: Compound 21 a is treated with a nitrogen sparged solution of 4/1 6N NH$_4$OH/CH$_3$CN in a nitrogen atmosphere for 1 hour at room temperature. The mixture is concentrated under vacuum to provide compound 22a which can be used without further purification.

BOC-protected AOTEG/SA/AHAB/TEG platform, 24a: Compound 23 (prepared as described; Jones et al. J. Med. Chem. 1995, 38, 2138–2144.) is added to a solution of four equivalents of compound 22a in nitrogen sparged 10/90H$_2$O/CH$_3$CN. To the resulting solution is added four equivalents of diisopropylethylamine. Upon completion of the reaction, the mixture is partitioned between water and CH$_2$Cl$_2$. The CH$_2$Cl$_2$ layer is concentrated, dried, and purified by silica gel chromatography to provide compound 24a.

AOTEG/SA/AHAB/TEG platform, 25a: The BOC-protecting groups are removed from compound 24a in a manner essentially similar to that described for the preparation of compound 16 to provide compound 25a.

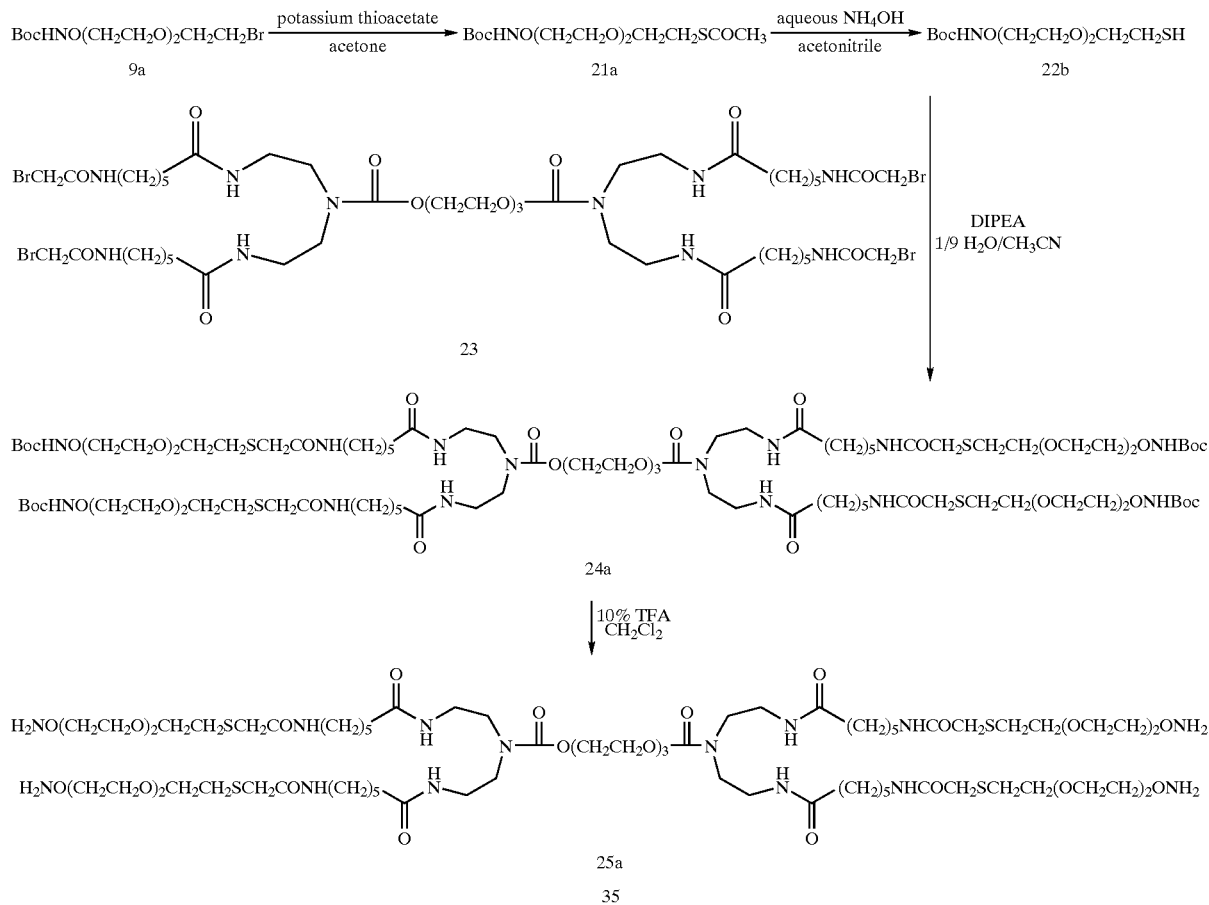

Synthesis of AOHEX/SA/AHAB/TEG Platform, 1-Iodo-6-(N-tert-butyloxycarbonyl)aminooxyhexane, compound 9b: To a heterogeneous mixture of 140 mg (1.05 mmol) of N-(tert-butyloxycarbonyl)hydroxylamine (Aldrich Chemical Co.) and 658 µL (1.35 mg, 4.0 mmol) of compound 12 was added 149 µL (152 mg, 1.0 mmol) of DBU. The mixture was stirred at room temperature for 30 seconds at which time the reaction mixture solidified. The solid mass was allowed to stand overnight and was dissolved in 50 mL of $CH_2Cl_2$. The solution was washed with 2×25 mL of 1 N NaOH and 3×25 mL of 1 N HCl. The combined basic aqueous layers were extracted with 25 mL of $CH_2Cl_2$, and the combined acidic aqueous layers were extracted with 25 mL of $CH_2Cl_2$. The combined $CH_2Cl_2$ layers were dried ($Na_2SO_4$), filtered, and concentrated to give a yhellow oil. Purification by silica gel chromatography (step gradient; 1/99/0.1 to 15/85/0.1 EtOAc/hexanes/MeOH) provided 216 mg (68%) of 9b as a yellow oil: $^1$H NMR (CDCl$_3$) δ 1.40 (m, 4H), 1.48 (s, 9H), 1.62 (m, 2H), 1.83 (m, 2H), 3.20 (t, 2H), 3.84 (t, 2H), 7.10 (s, 1H).

S-acetyl-6-(N-tert-butyloxycarbonyl)aminooxyhexan-1-thiol, Compound 21b: Compound 9b (209 mg (0.61 mmol) was added to a solution of potassium thioacetate in 15 mL of acetone, and the mixture was stirred at room temperature for 18 hours. The acetone was removed under vacuum, and the residue was partitioned between 50 mL of $CH_2Cl_2$ and 3×25 mL of 1 N NaOH. The $CH_2Cl_2$ layer was dried ($Na_2SO_4$), filtered, and concentrated to give a brown oil. Purification by silica gel chromatography (15/85 EtOAc/hexanes) provided 166 mg (94%) of compound 21b as a colorless oil. $^1$H NMR (CDCl$_3$) δ 1.39 (m, 4H), 1.48 (s, 9H), 1.59 (m, 4H), 2.32 (s, 3H). 2.86 (t, 2H), 3.82 (t, 2H), 7.10 (s, 1H).

6-(N-tert-butyloxycarbonyl)aminooxyhexan-1-thiol, Compound 22b: A purified sample of 22b was prepared as follows. Compound 21 b (50 mg, 172 µmol) and 22 µL (17.4 mg, 85.8 µmol) of tri-n-butylphosphine was placed under nitrogen, and 2 mL of a nitrogen sparged 1 M solution of NaOH in MeOH was added to the mixture. The mixture was stirred for 18 hours at room temperature, and 172 µL (180 mg, 3 mmol) of trifluoroacetic acid was added. The mixture was partitioned between 25 mL of EtOAc and 3×25 mL of 1 N HCl. The combined aqueous layers were extracted with 25 mL of EtOAc, dried ($Na_2SO_4$), filtered, and concentrated to give an oil. Purification by silica gel chromatography (15/85/0.1 EtOAc/hexanes/MeOH) provided 28 mg of 22b as a colorless oil: $^1$H NMR(CDCl$_3$) δ 1.32 (t, 1H), 1.40 (m, 4H), 1.49 (s, 9H), 1.62 (m, 4H), 2.53 (d of t, 2H). 3.84 (t, 2H), 7.09 (s, 1H).

BOC-Protected AOHEX/SA/AHAB/TEG platform, 24b: Compound 21 b (13 mg, 45 µmol) and 6 µL (4.5 mg, 22.3 µmol) of tri-n-butylphosphine was placed under nitrogen, and 3 mL of a nitrogen sparged solution of 4/1 6 N $NH_4OH/CH_3CN$ was added to the mixture. The mixture was stirred for 1 hour at room temperature and concentrated under vacuum. The residue was dissolved in 3 mL of a nitrogen sparged solution of 10/90 water/$CH_3CN$. To the resulting solution, which was kept under nitrogen atmosphere, was added 10 mg (7.44 µmol) of compound 23 followed by 8 µL (5.77 mg, 44.6 µmol) of diisopropylethylamine. The mixture was stirred for 18 hours and concentrated under vacuum. The residue was purified by silica gel chromatography (multiple step gradient, 1/99 to 5195 to 7.5/92.5 to 10/90 to 15/85 MeOH/$CH_2Cl_2$) to provide 14 mg (93%) of 24b as a colorless oil: TLC (10/90 MeOH/

$CH_2Cl_2$), $R_f$=0.3; mass spectrum (ES) m/z calculated for $C_{92}H_{173}N_{14}O_{26}S_4$ (M+H): 2018. Found: 2018.

AOHEX/SA/AHAB/TEG platform, 25b: The BOC-protecting groups are removed from compound 24b in a manner essentially similar to that described for the preparation of compound 16.

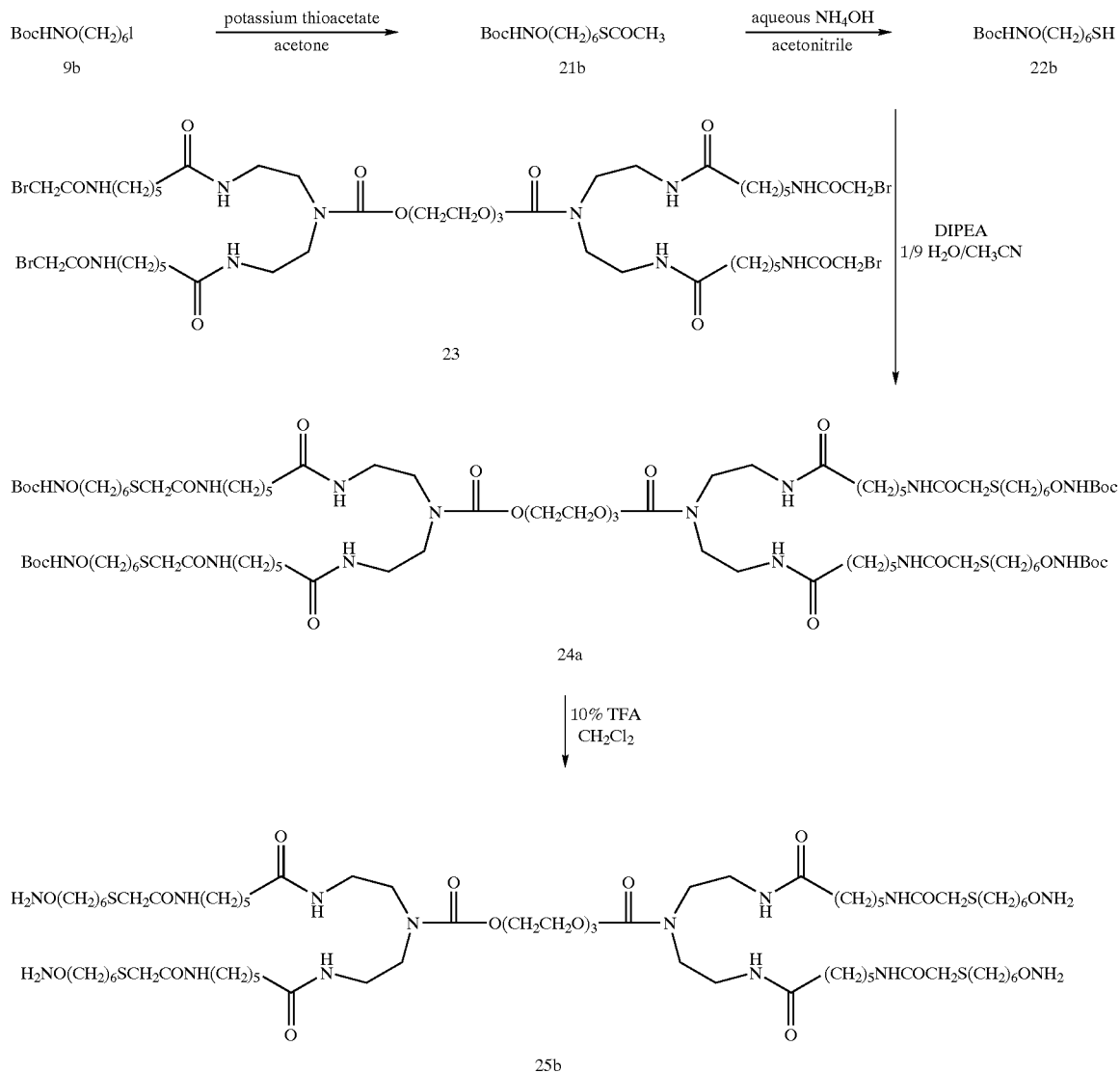

Synthesis of AOHOC/DT/TEG Platform, 6(tert-butyloxycarbonylaminooxy)hexan-1-ol, 27: To a solution of 179 µL (183 mg, 1.2 mmol) of DBU in 1 mL of $CH_2Cl_2$ was added 133 mg (1.0 mmol) of N-(tert-butyloxycarbonyl) hydroxylamine (Aldrich Chemical Co.) and 157 µL (217 mg, 1.2 mmol) of 6-bromohexan-1-ol (Aldrich Chemical Co.), and the mixture was stirred for 18 hours at room temperature. The mixture was concentrated to give a yellow oil. Purification by silica gel chromatography (35/5/65 EtOAc/MeOH/hexanes) gave 180 mg (77%) of compound 27 as a colorless oil: $^1$H NMR ($CDCl_3$) δ 1.39 (m, 4H), 1.48 (s, 9H), 1.59 (m, 4H), 3.63 (t, 2H), 3.85 (t, 2H), 7.42 (s, 1H); $^{13}$C NMR ($CDCl_3$) δ 25.6, 25.8, 28.1, 28.4, 62.8, 76.8, 81.7, 157.2.

Compound 28: To a solution of 100 mg (0.428 mmol) of compound 27 in 2 mL of $CH_2Cl_2$ at 0° C. was added 90 µL (88.1 mg, 1.11 mmol) of pyridine followed by 113 mg (0.557 mg) of p-nitrophenylchloroformate (Aldrich Chemical Co.). The mixture was stirred at room temperature for 4 hours, cooled to 0° C., acidified with 1 N HCl, and partitioned between 20 mL of 1 N HCl and 3×20 mL of $CH_2Cl_2$. The combined $CH_2Cl_2$ layers were washed with a saturated solution of $NaHCO_3$, dried ($MgSO_4$), filtered, and concentrated. Purification by silica gel chromatography to provided compound 28.

Compound 29: To a solution of diethylenetriamine in EtOAc is added two equivalents of diisopropylethylamine followed by two equivalents of compound 28. The mixture is stirred until the reaction is complete. The solvents are removed and the product, compound 29, is purified by silica gel chromatography.

BOC-protected AOHOC/DT/TEG Platform, 30: To a solution of triethylene glycol bis-chloroformate (Aldrich Chemical Co.) in pyridine is added two equivalents of compound 29. The mixture is stirred until the reaction is complete and partitioned between 1 N $HC_1$ and $CH_2Cl_2$. The $CH_2Cl_2$ layer is dried and concentrated, and the product is purified by silica gel chromatography to give compound 30.

AOHOC/DT/TEG Platform, 331: The BOC-protecting groups are removed from compound 30 in a manner essentially similar to that described for the preparation of compound 16.

Compound 33: A solution of compound 32 in THF is treated with 6 equivalents of NHS and 6 equivalents of DCC for 1 hour. To the mixture is added 4 equivalents of compound 11, and the mixture is stirred until the reaction is

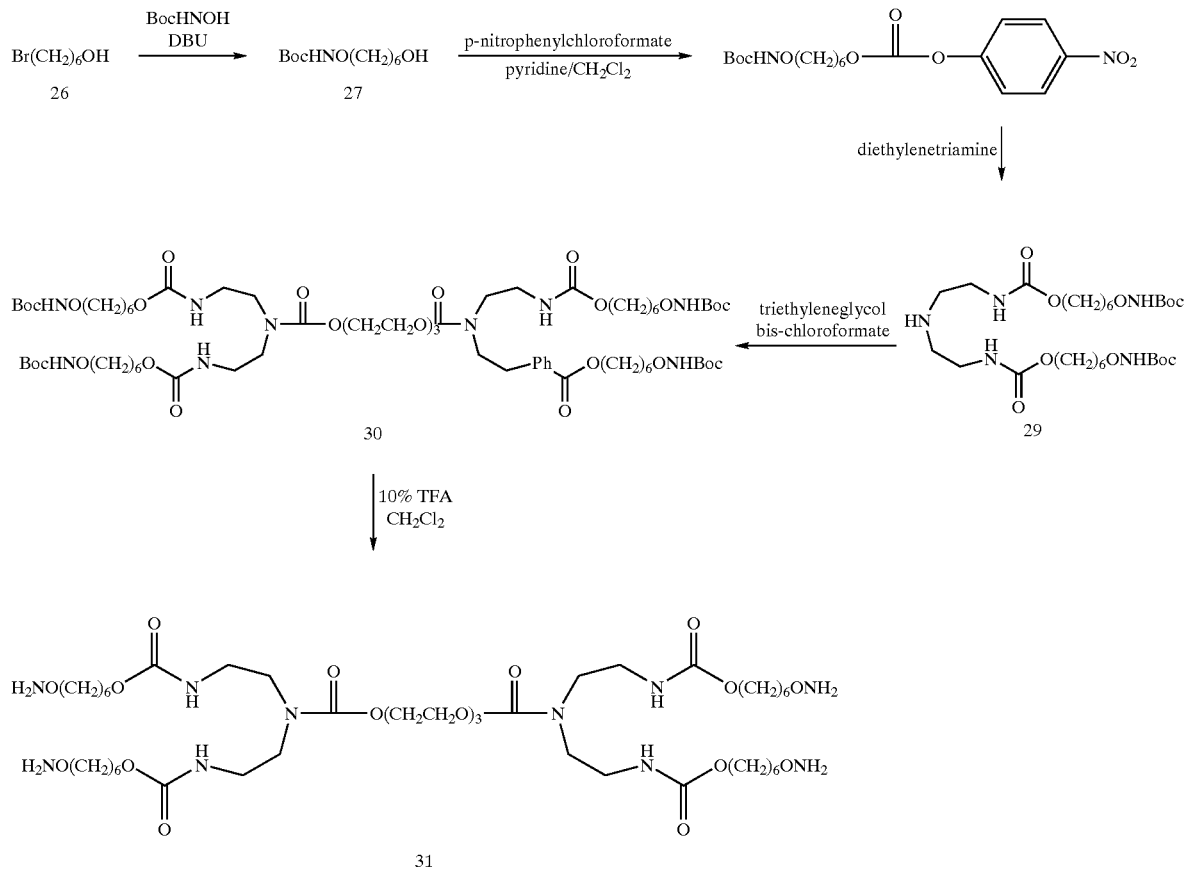

Synthesis of AOTEG/IDA/TEG Platform, Compound 32: To a solution of 7: triethylene glycol bis-chloroformate (Aldrich Chemical Co.) in pyridine is added two equivalents of iminodiacetic acid (Aldrich Chemical Co.). The mixture is stirred until the reaction is complete and partitioned between 1 N $HC_1$ and $CH_2Cl_2$. The $CH_2Cl_2$ layer is dried and concentrated, and the product is purified by silica gel chromatography to give compound 32.

complete. Acetic acid is added to quench excess DCC, and the resulting solids are removed by filtration. The filtrate is concentrated and purified by silica gel chromatography to provid compound 33.

Compound 34: The BOC-protecting groups are removed from compound 33 in a manner essentially similar to that described for the preparation of compound 16.

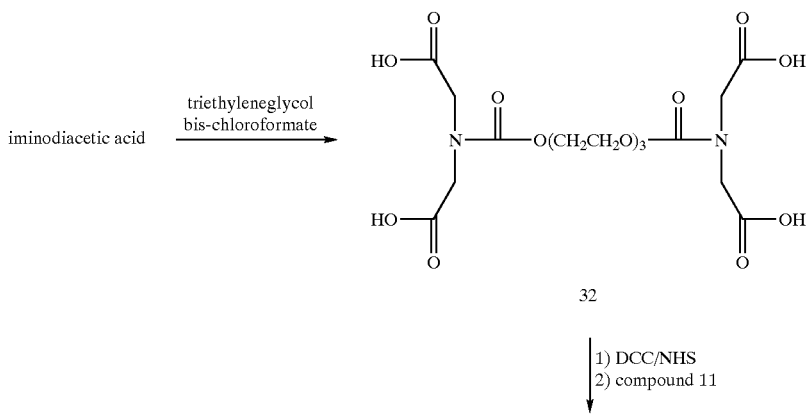

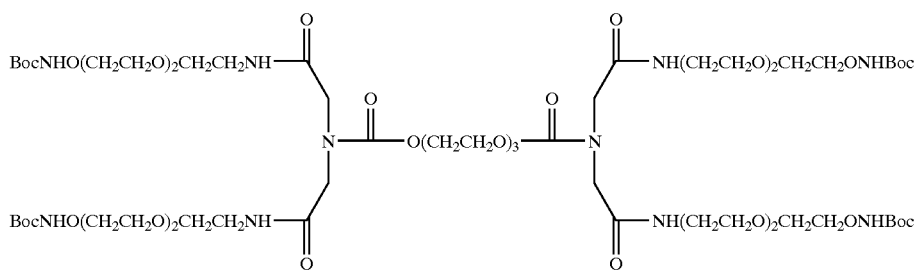

33

10% TFA
CH₂Cl₂

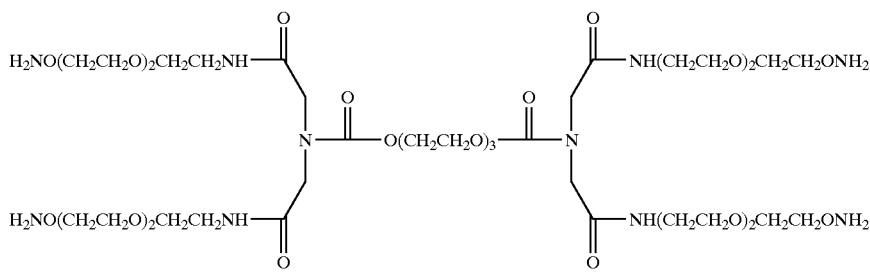

34

Synthesis of AOTEGO/LEV/PITG

Platform, p-Nitrophenyl-levulinate, 35: To a solution of 800 mg (6.89 mmol) of levulinic acid (Aldrich Chemical Co.) in 4.25 mL of pyridine was added 1.78 g (7.58 mmol) of 4-nitrophenyltrifluoroacetate (Aldrich Chemical Co.). The resulting solution was stirred for 15 minutes and partitioned between 28 mL of water and 2×28 mL of CH₂Cl₂. The combined CH₂Cl₂ layers were dried (MgSO₄), filtered, and concentrated. Purification of the concentrate by silica gel chromatography (step gradient, 25/75 to 30/70 EtOAc/hexanes) provided 1.06 g (74%) of compound 35: $^1$H NMR (CDCl₃) δ 2.28 (s, 3H), 2.87 (m, 4H), 7.29 (d, 2H), 8.28 (d, 2H).

1,2-Bis(2-(tert-butyloxycarbonyl)aminooxyethoxy)ethane, compound 36:

To 243 mg (0.66 mmol) of compound 12 was added 219 mg (1.64 mmol) of N-(tert-butyloxycarbonyl) hydroxylamine (Aldrich Chemical Co.) followed by 246 μL (250 mg, 1.64 mmol) of DBU. The mixture was stirred at room temperature until it solidified (approximately 1 hour). After standing for an additional hour, the mixture was dissolved in 2 mL of CH₂Cl₂, and the resulting solution was added to 100 mL of EtOAc to precipitate the hydrogen-iodide salt of DBU. An additional 50 mL of EtOAc was added, and the mixture was filtered. The filtrate was washed with 2×50 mL of 1 N HCl, 2×50 mL of 5% sodium bisulfite solution, and 25 mL of brine. The EtOAc layer was dried (Na₂SO₄), filtered, and concentrated to give an oil. Purification by silica gel chromatography (step gradient, 40/60 to 50/50 to 80/20 EtOAc/hexanes) to give 164 mg (65%) of compound 36 as a colorless oil: $^1$H NMR (CDCl₃) δ 1.48 (s, 18H), 3.65 (s, 4H), 3.72 (t, 4H), 4.02 (t, 4H), 7.80 (s, 2H); $^{13}$C NMR (CDCl₃) δ 28.2, 69.0, 70.3, 75.2, 81.3, 156.8.

1,2-Bis(2-aminooxyethoxy)ethane, compound 37: Compound 36 (559 mg, 1.47 mmol) was dissolved in 15 mL of of EtOAc, and HCl gas was bubbled through the solution for 30 minutes. The mixture was concentrated under vacuum to provide 72 mg (90%) of compound 37 as the HCl salt as a sticky residue: $^1$H NMR (D₂O) δ 3.75 (s, 4H), 3.87 (m, 4H), 4.27 (m, 4H); mass spectrum (ES) m/z calculated for C₆H₁₇N₂O₄ (M+H): 181.1. Found: 181.1.

Compound 38: Compound 3 is treated with a 30% Solution of HBr in acetic acid to remove the CBZ protecting groups and provide a tetra-amine hydrogen bromide salt. The tetra-amine is dissolved in a solution of sodium bicarbonate in water and dioxane, and to the resulting solution is added four equivalents of compound 35. Upon completion of the reaction, the mixture is partitioned between water and CH₂Cl₂. The CH₂Cl₂ layer is concentrated, dried, and purified by silica gel chromatography to provide compound 38.

AOTEGO/LEV/PITG Platform, compound 39: To a solution of compound 38 in 0.1 M pH 4.6 sodium acetate buffer is added twenty equivalents of compound 37. Upon completion of the reaction, the mixture is partitioned between water and CH₂Cl₂. The CH₂Cl₂ layer is concentrated, dried, and purified by silica gel chromatography to provide compound 39.

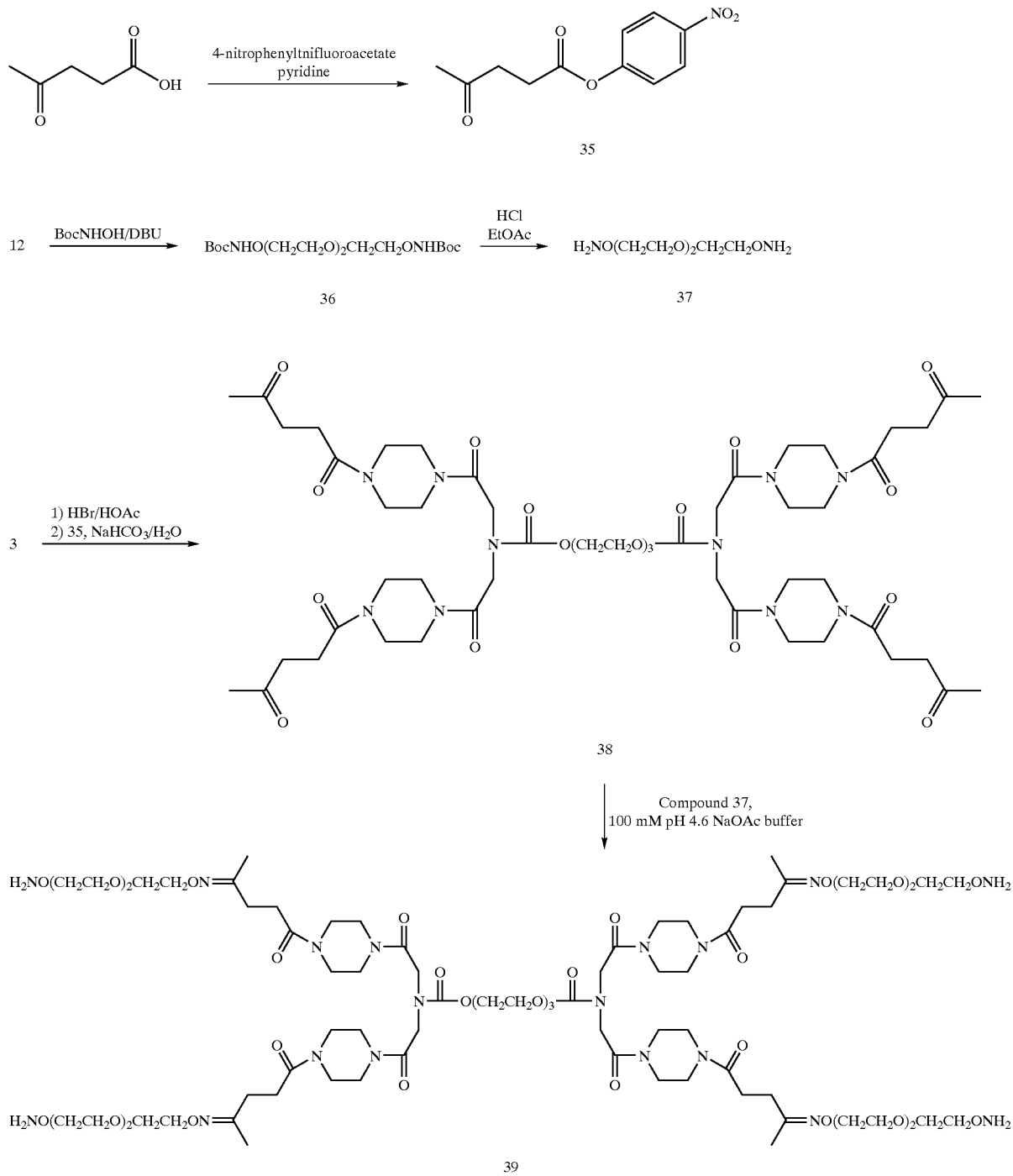

Synthesis of AO/DEGA/DEG Platform, Compound 41: Bromine (approximately six equivalents) is added dropwise to a solution of compound 40, six equivalents of triphenylphosphine, and 8 equivalents of pyridine in $CH_2Cl_2$ Until an orange color persists. The mixture is stirred at room temperature for 0.5 h or until reaction is complete, and a saturated solution of sodium bisulfite is added to destroy excess bromine. The mixture is then partitioned between $H_2O$ and EtOAc. The combined organic layers are washed with brine, dried ($Na_2SO_4$), filtered, concentrated, and purified by silica gel chromatography to provide compound 41.

Compound 42: To compound 41, is added six equivalents of N-(tert-butyloxycarbonyl)hydroxylamine (Aldrich Chemical Co.) and six equivalents of DBU. The mixture is heated as necessary for a sufficient time for the reaction to come to completion. When cool, the mixture is dissolved in $CH_2Cl_2$ and the resuting solution is added to EtOAc resulting in the formation of a precipitate which is removed by filtration, and the filtrate is concentrated. Purification by flash chromatography provides 8.

Compound 43: The BOC-protecting groups are removed from compound 42 in a manner essentially similar to that described for the preparation of compound 16.

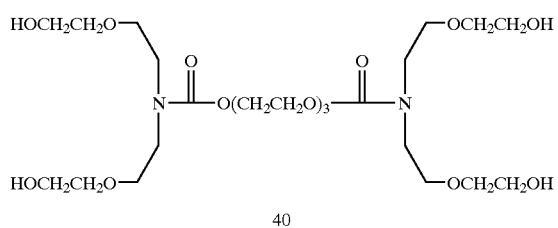
40
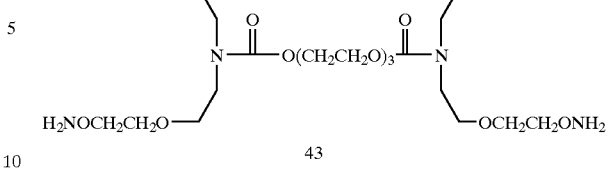
43
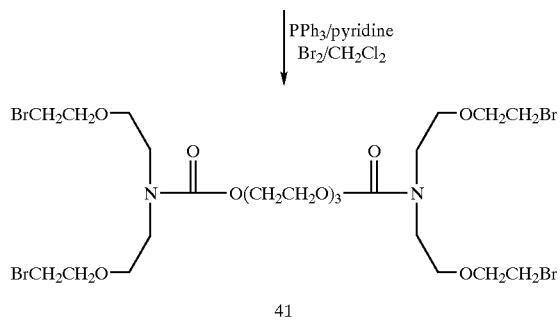
41
Alternative Method of Preparing a Tetravalent Conjugate Using Compound 37 as a Bifunctional Linker: As an alternative to reacting a transaminated domain 1 $\beta_2$GPI polypeptide directly with a tetravalent aminooxy platform, transaminated Domain 1 can be reacted with an

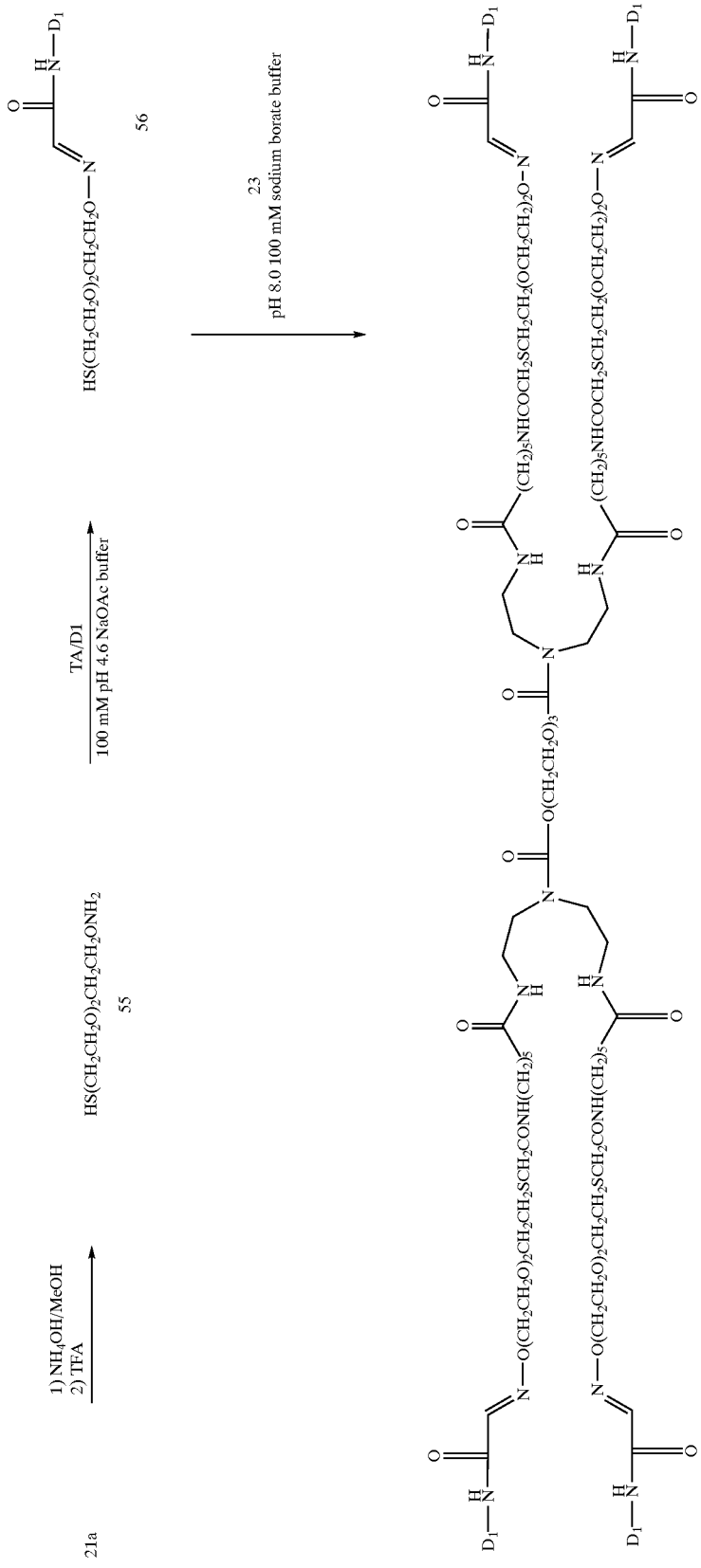

Example 6

Binding Properties of Domain 1 D₂GPI Polypeptide Tetrameric Conjugate Compound 44

Binding of tetrameric conjugate compound 44 to two affinity purified human 4/X5 anti-β₂-GPI antibodies was analyzed using surface plasmon resonance.

Materials and Methods for Kd Determinations of Tetrameric Conjugate Compound 44

Reagents. CM5 chips, NHS and EDC and HBS-EP buffer were from BIAcore. Human pooled normal IgG (Zymed) was immobilized in a separate flow cell on the chip and used as a negative control. Affinity purified 2-GPI domain 1 specific antibodies from 2 patients (6701 and 6626) were immobilized in separate flow cells.

Surface Plasmon Resonance. All experiments were done on a BIAcore™ 2000 instrument at 25° C. with a flow rate of 10 μL/minute. Chip equilibration and binding studies were performed with degassed HBS-EP buffer, which consists of 0.01 M HEPES pH 7.4, 0.15 M NaCl, 3 mM EDTA and 0.005% (v/v) surfactant $β_{20}$. Covalent coupling of protein ligands through their free amino groups to the CM5 chip was accomplished by flowing 40 μL of 0.05 M NHS/ 0.2M EDC over the chip to activate the chip, followed by exposure to the appropriate protein ligand. Affinity purified antibodies and normal IgG were immobilized by flowing 100 μL of a 100 μg/mL solution in 10 mM acetate, (pH 4.8) over the NHS activated CM5 chip. The excess reactive groups on the chip surface are then quenched with 40 μL of 1 M ethanoloamine, (pH 8.5).

Titrations. Baculovirus expressed domain 1 of β₂-GPI and the tetrameric compound 44 were diluted with HBS-EP, flowed over the chip, and response values were collected for 780 seconds. The chips were regenerated between sample exposures with 80 μL of 0.1 M glycine-HCl (pH 2.1), 0.1 M NaCl. A series of five titrations was done for each sample. Since the approach to binding equilibrium was incomplete during the measurement period, the equilibrium binding value ($R_{eq}$) was determined by fitting the association curves to the following equation using the manufacturer software (BiaEvaluation version 2.2, Uppsala, Sweden)):

$$R_t = R_{eq}(1 - e^{-ks(t-t0)}) + R_0$$

where $R_t$ is the measured BIAcore response at time t, $R_{eq}$ is the equilibrium plateau response, t is time, $t_0$ is initial time, $k_s$ is an apparent association constant ($k_s = k_a C + k_{dis}$ where $k_a$ is the association constant, C is the analyte concentration and $k_{dis}$ is the dissociation constant), and $R_0$ is a response offset, (Marquart-Levenberg algorithm).

Each titration association curve has the negative control (normal IgG) cell background for that titration subtracted. The calculated $R_{eq}$ were plotted versus concentration using GraphPad Prism software version 2.01. The data are fit to a one site binding (rectangular hyperbola: Y=Bmax* X/[Kd+ X]) and Kd values calculated in molar units. The molar concentrations of domain 1 and compound 44 were determined by absorbance at 280 nm and an extinction coefficient of 1.85.

Results and Discussion

Figure 10A:
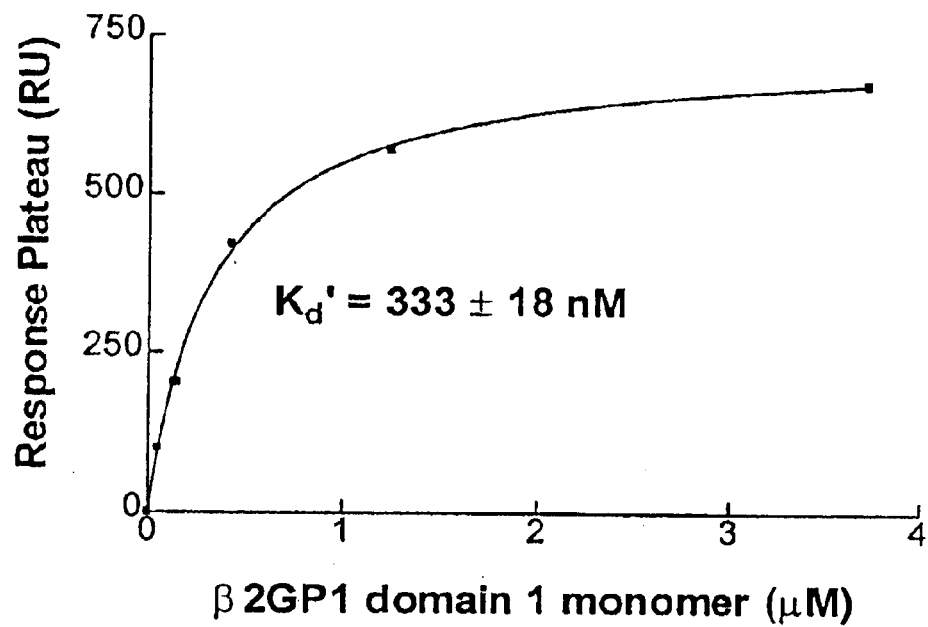
FIGS. 10A and 10B are graphs depicting apparent equilibrium binding values for various concentrations of domain 1 polypeptide (FIG. 10A) and tetrameric conjugate compound 44 (FIG. 10B) to affinity purified β$_2$GPI-dependent antiphospholipid antibodies from patient 6626. Apparent equilibrium dissociation constants are also shown.
Figure 10B:
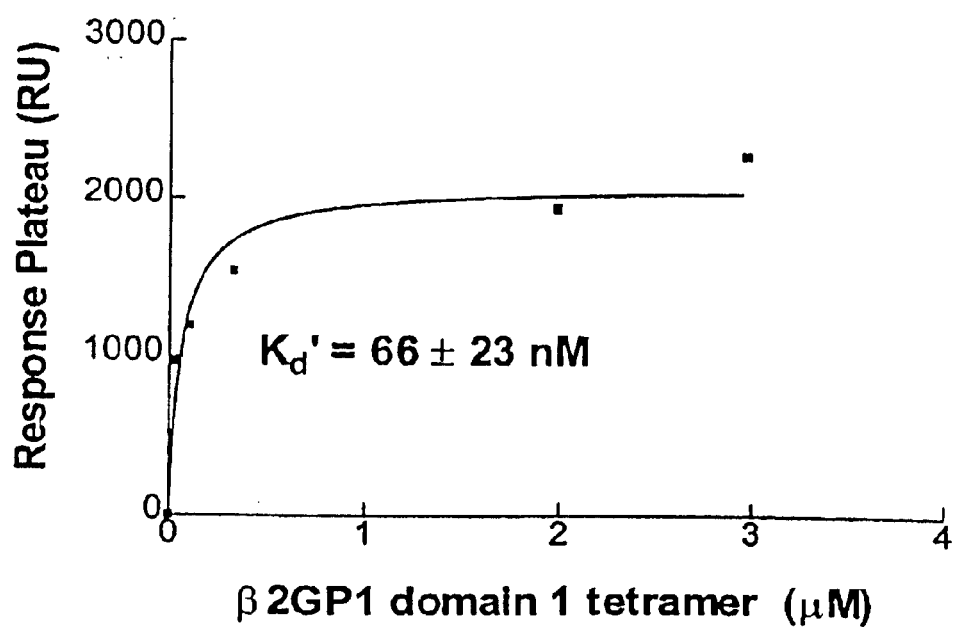
Figure 11A:
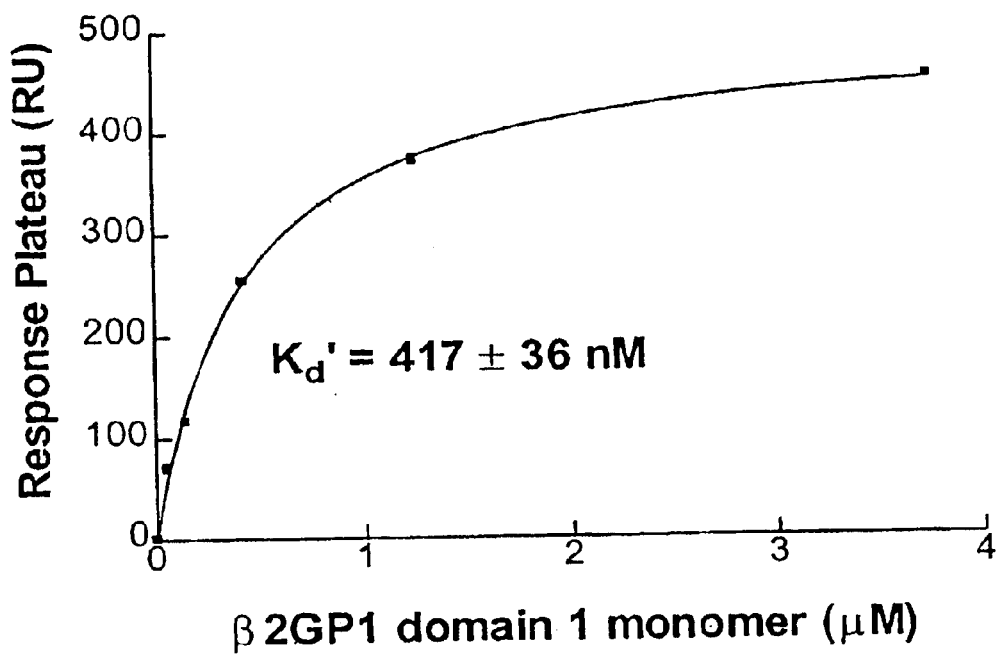
FIG. 11A and FIG. 11B are graphs depicting apparent equilibrium binding values for various concentrations of domain 1 polypeptide (FIG. 11A) and tetrameric conjugate compound 44 (FIG. 11B) to affinity purified β$_2$GPI-dependent antiphospholipid antibodies from patient 6701.
Figure 11B:
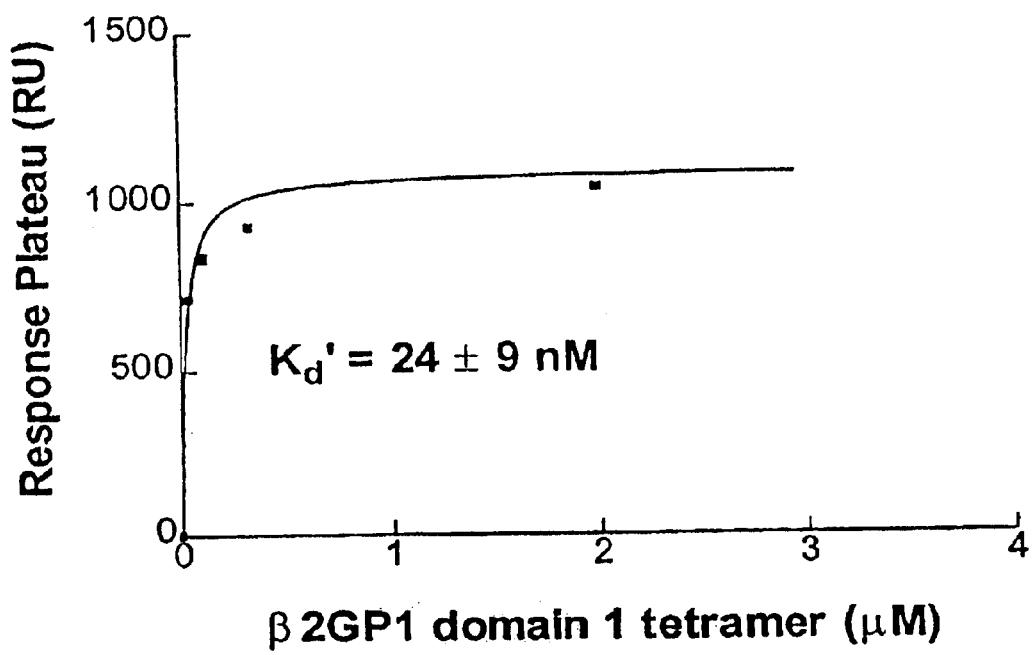
Figure 12:
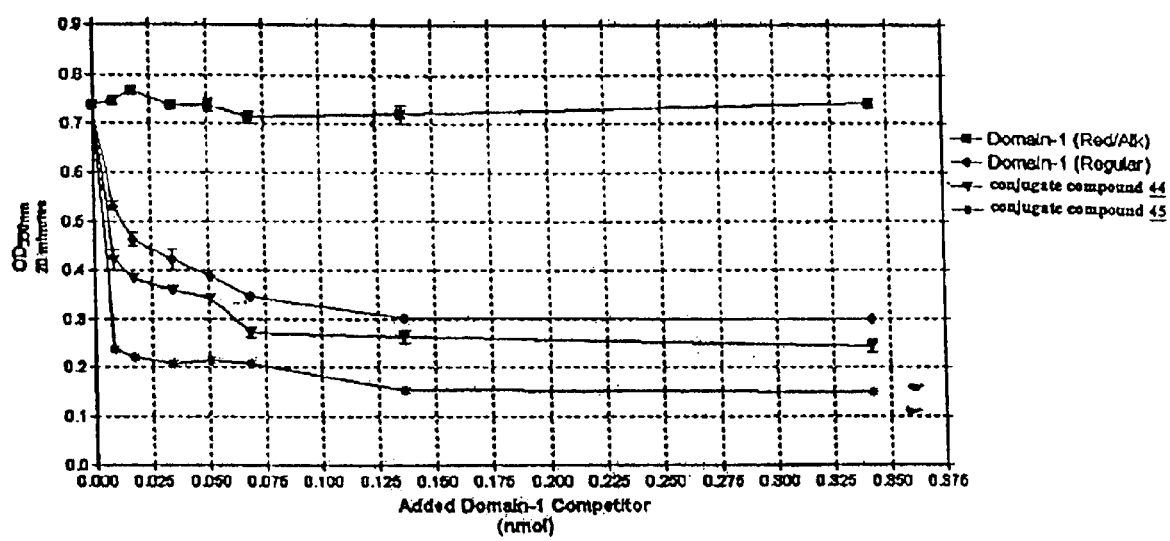
FIG. 12 is a graph depicting the results of competitive binding experiments in which a β$_2$GPI (coated on NUNC microtiter plates) was reacted with plasma from patient 6501 and variable amounts of tetrameric domain (—◇—) 1 conjugate compound 44 (—▼—), and compound 45 (—*—) as well as β$_2$GPI domain 1 polypeptide (—◆—) and β$_2$GPI domain 1 polypeptide that had been reduced and alkylated (—■—).
Figure 13:
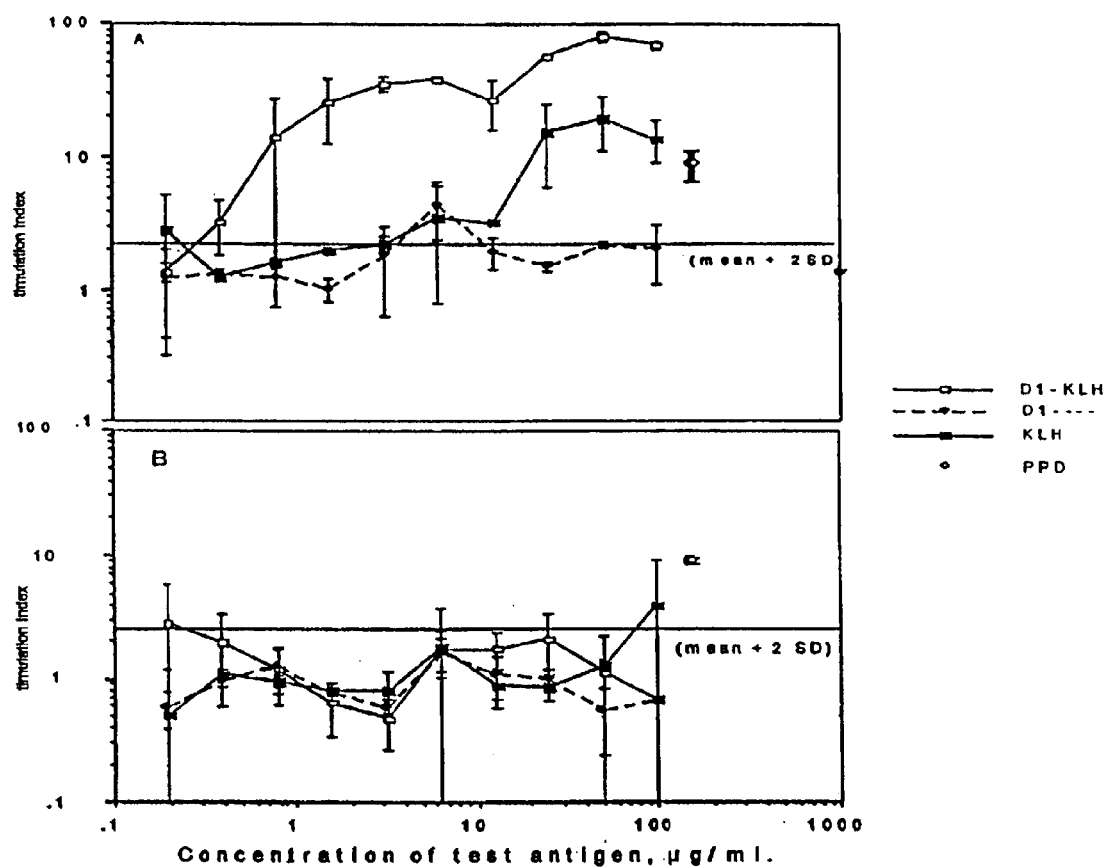
FIGS. 13A and B are graphs depicting dose response of popliteal lymph node cells from mice immunized with a β$_2$GPI domain 1 polypeptide-KLH conjugate in CFA (FIG. 13A) or CFA only (FIG. 13B). Symbols: —□—, KLH conjugate; —▼—, β$_2$GPI domain 1 polypeptide not conjugated to KLH; —■—, KLH; Δ, PPD.

Affinity purified antibodies from patients 6701 and 6626 were immobilized in separate microfluidic chambers and exposed to varying concentrations of human β₂GPI domain 1 or compound 44. The equilibrium binding value was determined for each concentration and plotted to determine the apparent equilibrium dissociation constant. The binding isotherms are shown in FIGS. 10 and 11 (extinction coefficient=1.85; 100 μg/ml immobilized antibody) and the dissociation constants are indicated in Table 8.

These experiments demonstrate that affinity purified antiphospholipid antibodies bind to domain 1 of β₂GPI. In addition, they demonstrate that tetrameric conjugates of a domain 1β₂GPI polypeptide linked to a platform are also capable of binding to these antibodies with affinities that are equivalent to or greater than the molar concentration of domain 1 present in the tetramer.

TABLE 8

Apparent equilibrium dissociation constants for domain 1 and compound 44 binding to affinity purified antiphospholipid antibodies

| Patient | Domain 1 | Compound 44 |
| --- | --- | --- |
| 6626 | 333 ± 18 nM | 66 ± 23 nM |
| 6701 | 417 ± 36 nM | 24 ± 9 |

Example 7: Testing Domain 1 β₂GPI Polypeptide Conjugates for Competitive Antibody Binding in Vitro Nunc Maxisorp microplates (Nalge Nunc International, Denmark) were coated with 100 $\mu$L/well of $\beta_2$GPI at 2.5 $\mu$g/mL in PBS, incubated for 2 hours at room temperature, and blocked for 2 hours at room temperature with 250 $\mu$l/well of 2% nonfat milk with 0.4 Tween-80 (Sigma Chemical Co.). Following five washes with TBS, to each well was added 100 $\mu$L of a solution prepared less than one hour earlier designed to deliver per well 1:200 final dilution of plasma from patient 6501 and variable amounts of tetrameric domain 1 conjugates compound 44 and compound 45 or control domain 1 monomers all in 2% nonfat milk with 0.4% Tween-80. After incubation for one hour at room temperature the plates were washed 5× with TBS. To each well was added 100 $\mu$L of alkaline phosphatase-conjugated anti-human IgG, gamma chain specific (Zymed) diluted 1:1000 in 2% nonfat milk with 0.4% Tween-80. After one hour at room temperature the plates were washed 5× with TBS. To each well was added 100 $\mu$l PPMP chromogenic substrate solution for color development at room temperature. Optical absorbance per well was determined at $A_{550nm}$ in a commercial microplate reader (Bio-Tek Instruments EL3 11). The results shown in FIG. 12 indicate that both compounds 44 and 45, effectively compete for antiphospholipid antibody present in serum (patient 6501). Reduced and alkylated domain 1 displays no such competition and is a negative control. Competitive binding is also exhibited by regular, monomeric domain 1 and is included as a positive control.

Example 8

Immunized Mouse Model to Test Domain 1 B2GPI Polypeptid Conjugates

The requirements of an immunized model to test for tolerance to domain 1 B2GPI polypeptides are: (1) the immunization must engender antibodies that recognize domain 1 and (2) the immunization must not engender T cells that recognize domain 1. Immunization with the domain 1 polypeptides-KLH conjugate engenders T cells that recognize KLH but not detectable reactivity to domain 1. To this end we have made, in the insect cell system, a domain 1 $\beta_2$GPI polypeptide that contains a fifth cysteine at the carboxyl terminus (amino acid 1 to amino acid 66 of SEQ ID NO: 1). This molecule has been covalently attached to KLH via the fifth cysteine. This conjugate has been used to immunize mice. Immunization with the domain 1-KLH conjugate engenders T cells that recognize KLH but not detectable reactivity to domain 1. On the other hand, immunization with the domain 1-KLH conjugate does result in the production of domain 1 specific antibodies.

Materials and Methods

ELISA to Detect Anti-Domain 1 Antibody

NUNC microtiter wells were coated with 50 μl of B2GPI at 5 μg/ml in 0.1 M bicarbonate (pH 9.5), overnight. The wells were washed with PBS and then blocked for one hour with 2% Nonfat dry milk (NFDM). The wells were washed and 50 μl of serial dilutions, in 2% NFDM, of individual mouse serum was added, incubated at room temperature for one hour, washed and 50 Ill of alkaline phosphatase conjugated anti-mouse IgG was added, incubated one hour at room temperature, washed and 50 μl of substrate added. The OD at 550 nm was read after 30 minutes. A pool was made of the serum from the mice that had been primed with 50 μg of the conjugate. This pool was tested in all assays and the results are expressed as a percent of this standard pool.

Competitive Inhibition ELISA

NUNC Microplates were coated with 50 μl of recombinant β2GPI at 5 μg/ml in 0.1 M bicarbonate, pH 9.5, incubated overnight at 4° C., washed three times with 0.15 M PBS (pH 7.2), and blocked for one hour at room temperature with 75 μl of 2% Non-fat dried milk in PBS (2% NFDM). Test inhibitors were diluted in 2% NFDM and 25 ill of each dilution or NFDM alone was added to coated wells. Monoclonal antibody was diluted in 2% NFDM and 25 μl of a constant concentration was added to the wells. The contents of the wells were mixed and the plates were incubated at room temperature for one hour. After the plates were washed three times with PBS, 50 μl of alkaline phosphatase conjugated anti-mouse IgG, gamma chain specific, diluted appropriately in 2% NFDM was added and incubated at 37° C. for one hour. After the plates were washed three times with PBS, 50 μl of alkaline phosphatase chromogenic substrate were added and the plates incubated for 30 minutes at 20° C. The $A_{550}$ was measured in a microplate autoreader. The percent inhibition was determined as follows: [(mean $A_{550}$ obtained from the control wells without inhibitor less $A_{550}$ of background)−($A_{550}$ to obtained in the presence of inhibitor less $A_{550}$ of background)−(mean $A_{550}$ obtained from the control wells without inhibitor less $A_{550}$ of background)] times 100.

Immunized Mouse Model for Anti-Domain 1 Antibodies

Groups of 5 C57B116 mice were primed with either 10, 50 or 100 μg of the KLH-Domain 1 conjugate adsorbed to alum plus $2\times10^9$ pertussis organisms as an adjuvant. Three weeks later all of the mice were boosted with 10 μg of the conjugate in saline. Seven days after the boost the mice were bled, serum harvested and tested for anti-domain 1 activity. The results are shown in FIG. 14. Immunization with domain 1-KLH did not generate a domain 1-specific antibody response.

Mouse Immunization and T Cell Proliferation Assay

C57B1/6 mice were injected in the hind footpad with 25 μg of domain 1 (D1)-KLH conjugate emulsified in complete Freunds adjuvant (CFA). Another group of mice was injected in the hind footpad with emulsified CFA (no antigen). Seven days later the popliteal lymph nodes were harvested from 5 mice of each group. Nodes from like immunizations were pooled and single cell suspensions made. The cells were cultured as described above for the human cells except the test antigens were D1-KLH, KLH and domain 1 (not conjugated). PPD was used as a positive control. On day 4, 25 μl of $^3$H-thymidine containing 1 μCi was added to each well. On day 5 the contents of the wells were harvested and the amount of radioactivity in each was determined. A Stimulation Index (SI) was calculated for each well by dividing the CPM of the well by the mean CPM of the negative controls. The mean (and standard deviation) SI for each of the duplicates was determined.

Results and Discussion

The specificity of the polyclonal mouse anti-KLH-Domain 1 conjugate was determined by a competitive inhibition ELISA assays. Various recombinant forms of $\beta_2$GPI were mixed with limiting amounts of antibody in wells that had been coated with $\beta_2$GPI. The amount of antibody that remained bound to the wells was then detected with an alkaline phosphatase conjugated second antibody. The percent inhibition was determined, as described in the methods section, and plotted vs. the molar concentration of the inhibitor. The results are shown in FIG. 15. Immunization with the same conjugate does generate an antibody response that is specific for domain 1 (FIG. 15).

With respect to T cell proliferation, the results shown in FIG. 13 demonstrate that the cells from domain 1-KLH primed mice proliferated in response to both domain 1-KLH and KLH as well as the positive control PPD. They did not respond to domain 1 (non-conjugated). On the other hand the cells from the CFA only primed mice did not respond to the test antigens but did respond to the positive control PPD.

For an immunized mouse model, namely, that the priming must not prime T cells that recognize a given tolerogen but must generate memory B cells that will recognize the tolerogen, both of the two basic requirements for an immunized mouse model have been accomplished in the immunized mouse model presented here.

Example 9

Testing Domain 1 $\beta_2$GPI Polypeptide as a Tolerogen in Vivo

Mice are primed with a domain 1 $\beta_2$GPI polypeptide conjugated to keyhole limpet hemocyanin (KLH) on alum plus pertussis as an adjuvant as described above. Three weeks later, the mice are treated with a range of doses of toleragen, which may or may not be conjugated to a platform. One group is not treated and acts as a control group. Five days later, all of the mice, including the control group, are boosted with 10 μg of domain 1 $\beta_2$GPI polypeptide conjugated to KLH and seven days later the mice are bled. Their sera are analyzed for anti-$\beta_2$GPI domain 1 antibodies by any known method, including, for example, ELISA as described in the preceding examples. These values are then used to determine a mean and standard deviation for all individuals of a group.

Example 10

Testing T Cell Reactivity

Establishing the lack of T cell reactivity to a domain 1 $\beta_2$GPI polypeptide would indicate that, as a toleragen, it does not supply any epitopes for a second signal to B cells from T cells. Conversely, if the toleragen provided a proliferation (activation) signal to T cells, it is possible that the toleragen would exacerbate B cell response.

To determine T cell activation, circulating lymphocytes are collected and placed in tissue culture. The domain 1 $\beta_2$GPI polypeptide(s) to be tested is added to the culture for approximately one week. At the end of the week, T cells are pulsed with $^3$H-thymidine to determine if there has been cellular proliferation. Optionally, presence of cytokines in the tissue culture supernatant is also determined.

Example 11

Anti β$_2$-GPI Antibodies Contribute to Hyperrcoagulation by Delaying the Inactivation of Factor Va Methods Activated factor V (factor Va) levels were determined in normal human plasma after the initiation of clotting in the presence and absence of affinity purified antibodies or total IgG preparations from patients diagnosed with antiphospholipid syndrome (APS). The affinity-purified antibodies were characterized as anti β$_2$-GPI domain 1. Total IgG was prepared from patient serum as described below.

Measurement of factor Va levels, was determined in a modified two-stage clotting assay using an Amelung KC4A microcoagulometer as follows. Fifty µl factor V deficient human plasma (Chromogenix) was pre-incubated for 1 minute at 37° C. in a spinning microcuvette. Samples were diluted 1:10 with pre-warmed (37° C.) Owren's Buffer (Sigma). Fifty µl of the diluted sample was added to the 50 µl of V deficient plasma. One hundred µl of 37° C. ThromboMAX plus calcium (Sigma) was added to initiate clotting. Time to clot was recorded. One unit of Va activity is defined as the time to clot for the V deficient plasma with 1:10 dilution of normal reference human plasma (Accuclot, Sigma). One unit of factor Va activity in this experimental system corresponds to a clot time of approximately 30 seconds.

To determine the amount of factor Va being generated over time in the presence or absence of antiphospholipid antibody or IgG the following system was used to generate the samples tested in the above standard assay. The following reagents were mixed and incubated at 37° C.: one part normal human reference plasma (Accuclot, Sigma), one part 25 mM CaCl$_2$ and one part consisting of phosphatidyl-serine reagent (125 µg/ml) and Tris-buffered saline (TBS) and antibody or IgG (if applicable at the desired concentration). TBS was used to correct for varying volumes of antibody or IgG. The normal plasma, phophatidyl-serine, antibody or IgG (if present) and TBS were mixed and incubated at 37° C. for 2 minutes before the addition of 37° C. CaCl$_2$ to initiate clotting and the clot was removed manually as it formed. The total volume of the sample mixture was dependent on the number of timepoints assayed. At each timepoint 12.5 VI of the incubating sample was removed, diluted 1:10 in Owren's buffer and assayed in the standard factor Va assay above. The levels of Va generated in the sample over time are reflected in a correction of the factor V deficient plasma clotting time. The peak Va levels occur at 4–5 minutes after clotting is initiated and the levels are in the range of 4–7 units of factor Va activity. This corresponds to a clot time of approximately 5–6 seconds in the standard assay for this experimental system.

In cases where APS patient IgG was added to the assay total IgG was prepared from human serum samples by combining 100 µl serum (diluted 1:1 with Pierce Immunopure IgG binding buffer) with 100 µl agarose-immobilized protein G beads (Pierce Immunopure Plus).

The mixture was slowly shaken at ambient temperature for 10 minutes. Protein G binds the F$_c$ region of all subclasses of human immunoglobulin G. After 10 minutes the mixture was centrifuged briefly to pellet the beads. The serum mixture supernatant was discarded.

The beads with bound IgG were then washed three times with 200 µl IgG binding buffer to remove adsorbed proteins. The bound IgG was then eluted from the protein G beads with three times. 100 µl of IgG elution buffer (Pierce, Immunopure IgG elution buffer). The eluted IgG was immediately neutralized with 100 µl 1M NaPO$_4$ pH 7.5, for a total final volume of 400 µl of IgG preparation from the 100 µl plasma sample. Neutralized IgG preparations are stored at 4° C. until analysis.

Protein concentration of IgG preparations was determined by standard microplate Bradford method (Bio-Rad reagent). Five µl of each sample was assayed in triplicate, with a standard curve of bovine serum albumin on each plate. Protein concentrations were calculated by KC4 software.

For analysis in the factor Va clotting assay, 100 µl of the IgG preparation was concentrated to 25 µl with a Microcon centrifugal filter device (Amicon, molecular weight cutoff of 30,000). The entire 25 µl is used for the single timepoint factor Va assay.

Results

Figure 16:
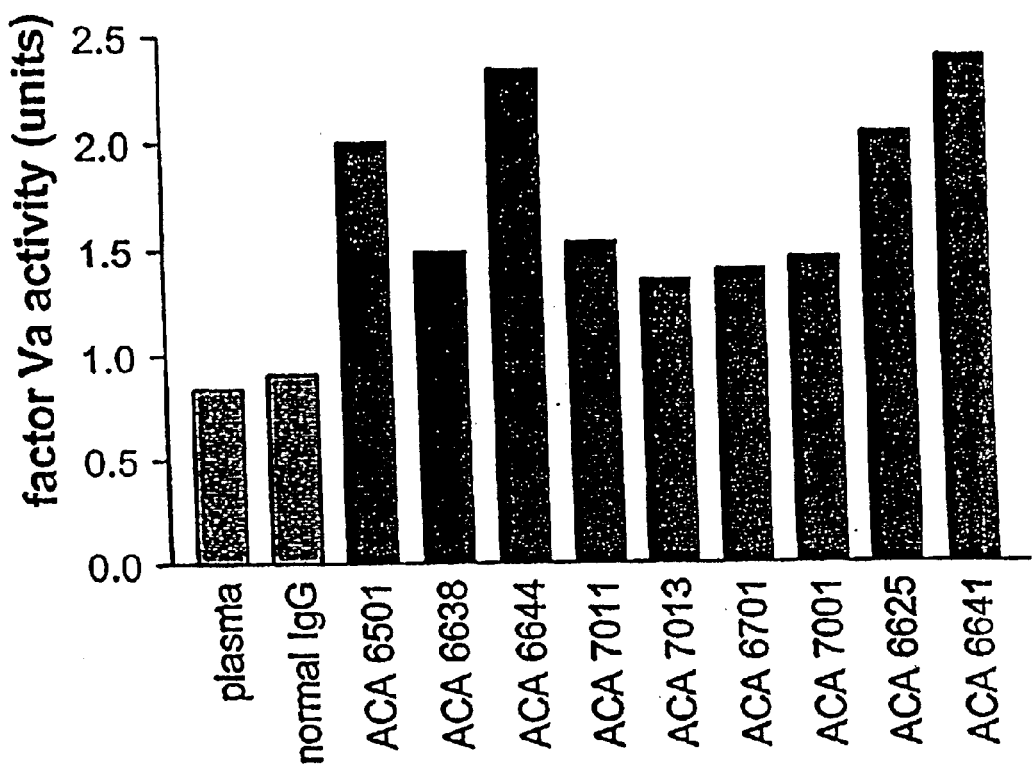
FIG. 16 is a bar graph depicting the effect of affinity purified β$_2$GPI-dependent antiphospholipid antibodies on Factor Va activity in blood from various patients (6501, 6636, 6644, 7011, 7013, 6701, 7001, 6625, 6641) as well as normal plasma and IgG.

The effect of total IgG from antiphospholipid patients and affinity purified antibodies from normal controls was compared for their ability to delay factor Va inactivation in an in vitro coagulation assay. The results for total IgG and affinity purified antibodies are shown in Table 9 and FIG. 16, respectively. IgG and affinity purified antibodies from normal control subjects did not alter the inactivation of factor Va observed at 20 minutes after initiating coagulation. In contrast, the IgG fraction from antiphospholipid patients delayed the inactivation of factor Va ($p<0.05$ by student's t-test). Similar effects on factor Va inactivation were observed for the affinity purified antibodies. These data suggest that human anti-b2-GPI antibodies can create a hypercoagulative state in part by delaying the inactivation of factor Va.

TABLE 9

| I.D. | 20" Va (Units) | IgG (mg) | activity (Units/mg) |
|---|---|---|---|
| APS Patient IgG | | | |
| 7308 | 0.98 | 0.08 | 12.25 |
| 7309 | 0.85 | 0.06 | 14.17 |
| 7310 | 0.85 | 0.06 | 14.17 |
| 7311 | 0.84 | 0.07 | 12.00 |
| 7312 | 0.92 | 0.06 | 15.33 |
| 7313 | 0.82 | 0.06 | 13.67 |
| 7314 | 1.13 | 0.06 | 18.83 |
| 7315 | 0.99 | 0.07 | 14.14 |
| 7316 | 0.87 | 0.06 | 14.50 |
| 7317 | 0.92 | 0.08 | 11.50 |
| 7318 | 0.81 | 0.08 | 10.13 |
| 7319 | 0.95 | 0.10 | 9.50 |
| 7320 | 0.83 | 0.05 | 16.60 |
| 7321 | 0.84 | 0.07 | 12.00 |
| 7322 | 0.81 | 0.06 | 13.50 |
| 7323 | 0.83 | 0.09 | 9.76 |
| 7301 | 0.83 | 0.05 | 16.60 |
| 7302 | 0.87 | 0.05 | 17.40 |
| 7303 | 1.05 | 0.08 | 13.13 |
| 7304 | 1.44 | 0.07 | 20.57 |
| 7305 | 0.79 | 0.08 | 9.88 |
| 7306 | 0.90 | 0.07 | 12.86 |
| 7307 | 1.10 | 0.07 | 15.71 |
| 6501 | 1.16 | 0.06 | 19.33 |
| 6636 | 1.21 | 0.05 | 24.20 |
| 6625 | 0.86 | 0.10 | 8.60 |
| 6646 | 0.72 | 0.05 | 14.40 |

TABLE 9-continued

| I.D. | 20" Va (Units) | IgG (mg) | activity (Units/mg) |
|---|---|---|---|
| 6623 | 1.17 | 0.07 | 16.71 |
| 6510 | 0.70 | 0.05 | 14.00 |
| mean | 0.93 | 0.07 | 14.33 |
| STD | 0.17 | 0.01 | 3.55 |
| Normal IgG | | | |
| N260F | 0.77 | 0.06 | 12.83 |
| N712M | 0.69 | 0.07 | 9.86 |
| N266F | 0.78 | 0.09 | 8.67 |
| N199F | 0.79 | 0.08 | 9.88 |
| N280M | 0.76 | 0.07 | 10.86 |
| mean | 0.76 | 0.07 | 10.42 |
| STD | 0.039623 | 0.011402 | 1.557503 |

Although the foregoing invention has been described in some detail by way of illustration and example for purposes of clarity of understanding, it will be apparent to those skilled in the art that certain changes and modifications will be practiced. Therefore, the description and examples should not be construed as limiting the scope of the invention, which is delineated by the appended claims.

We claim:

1. A polypeptide comprising a domain 1 β₂GPI polypeptide, wherein said polypeptide specifically binds to a β₂GPI-dependent antiphospholipid antibody, said polypeptide comprises at least 30 contiguous amino acids of SEQ ID NO:4, and said polypeptide is less than about 75 amino acids in length.

2. The polypeptide of claim 1; wherein the domain 1 β₂GPI polypeptide consists of the polypeptide SEQ ID NO:4.

3. The polypeptide of claim 1; wherein the domain 1 β₂GPI polypeptide consists of about amino acid 1 to about amino acid 66 of SEQ ID NO:2.

4. A kit comprising the polypeptide of claim 3.

5. The kit of claim 4, wherein the kit is for detecting coagulation.

6. The kit of claim 4, wherein the kit is for detecting an antibody that specifically binds to a domain 1 β₂GPI polypeptide.

7. The polypeptide of claim 1, wherein the domain 1 β₂GPI polypeptide comprises about amino acid 1 to about amino acid 59 of SEQ ID NO:4.

8. The polypeptide of claim 1, wherein the domain 1 β₂GPI polypeptide consists of about amino acid 2 to about amino acid 63 of SEQ ID NO:2.

9. A kit comprising the polypeptide of claim 8.

10. The polypeptide of claim 1, wherein the domain 1 β₂GPI polypeptide comprises SEQ ID NO:29.

11. A kit comprising the polypeptide of claim 10.

12. The polypeptide of claim 1, wherein the polypeptide comprises SEQ ID NO: 5, 6, 7, 8, 9, 10, 11, or 12.

13. The polypeptide of claim 1, wherein the polypeptide comprises at least 40 contiguous amino acids of SEQ ID NO:4.

14. The polypeptide of claim 1, wherein the polypeptide further comprises amino acid 40 through amino acid 45 of SEQ ID NO:4, amino acid 38 through amino acid 44 of SEQ ID NO:4, or amino acid 19 of SEQ ID NO:4.

15. The polypeptide of claim 1, wherein the polypeptide comprises at least 40 contiguous amino acids of SEQ ID NO:4.

16. The polypeptide of claim 1, wherein the polypeptide is less than about 60 amino acids in length.

17. A kit comprising the polypeptide of claim 1.

18. A polypeptide comprising a domain 1 β₂GPI polypeptide, wherein said polypeptide specifically binds to a β₂GPI-dependent antiphospholipid antibody, said polypeptide comprises SEQ ID NOS: 5, 9, 10, 11, or 12, and said polypeptide is less than about 75 amino acids in length.

19. The polypeptide of claim 18, wherein the polypeptide is less than about 50 amino acids in length.

20. The polypeptide of claim 18, wherein the polypeptide is less than about 25 amino acids in length.

21. The polypeptide of claim 18, wherein the polypeptide comprises SEQ ID NO: 5.

22. The polypeptide of claim 18, wherein the polypeptide comprises SEQ ID NO: 9.

23. The polypeptide of claim 18, wherein the polypeptide comprises SEQ ID NO: 10.

24. The polypeptide of claim 18, wherein the polypeptide comprises SEQ ID NO: 11.

25. The polypeptide of claim 18, wherein the polypeptide comprises SEQ ID NO: 12.

26. The polypeptide of claim 18, wherein the polypeptide further comprises at least 10 contiguous amino acids of SEQ ID NO:4.

27. The polypeptide of claim 18; wherein the polypeptide further comprises at least 20 contiguous amino acids of SEQ ID NO:4.

28. The polypeptide of claim 18, wherein the polypeptide further comprises amino acid 40 through amino acid 45 of SEQ ID NO:4, amino acid 38 through amino acid 44 of SEQ ID NO:4, or amino acid 19 of SEQ ID NO:4.

29. The polypeptide of claim 18, wherein the polypeptide is less than about 60 amino acids in length.

30. A kit comprising the polypeptide of claim 18.

31. A polypeptide comprising a domain 1 β₂GPI polypeptide, wherein said polypeptide specifically binds to a β₂GPI-dependent antiphospholipid antibody, said polypeptide comprises SEQ ID NO:6, SEQ ID NO:8, or SEQ ID NO:7, and said polypeptide is at least 15 amino acids in length and less than 25 amino acids in length.

32. The polypeptide of claim 31, wherein the polypeptide comprises SEQ ID NO:6.

33. The polypeptide of claim 31, wherein the polypeptide comprises SEQ ID NO:7.

34. The polypeptide of claim 31, wherein the polypeptide comprises SEQ ID NO:8.

35. The polypeptide of claim 31, wherein the polypeptide further comprises amino acid 19 of SEQ ID NO:4.

36. The polypeptide of claim 31, wherein the polypeptide comprises further at least 10 contiguous amino acids of SEQ ID NO:4.

37. A kit comprising the polypeptide of claim 31.

38. A method of detecting an antibody which specifically binds to the polypeptide of claim 1 in a sample, comprising (a) contacting antibody in the sample with the polypeptide of claim 1 under conditions that permit the formation of a stable antigen-antibody complex; and (b) detecting stable complex formed in step (a), if any.

39. The method of claim 38, wherein the antibody is a β₂GPI-dependent antiphospholipid antibody.

40. A method of purifying a β₂GPI-dependent antiphospholipid antibody, comprising contacting a biological sample with the polypeptide of claim 1 under conditions that permit the formation of a stable antigen-antibody complex, and obtaining the complex formed, if any.

41. A method of inducing tolerance in an individual, comprising administering an effective amount of a composition comprising the polypeptide of claim 1 to the individual.

42. The method of claim 41, wherein the individual is human.

43. A method for detecting β₂GPI-dependent antiphospholipid antibody mediation of coagulation, comprising the steps of:
 (a) performing a first coagulation assay using a suitable biological sample from an individual, wherein the polypeptide of claim 1 is added to the assay;
 (b) performing a second coagulation assay using a suitable biological sample from the individual in the absence of the polypeptide of claim 1;
 (c) comparing the assay results of steps (a) and (b), wherein a difference in the results indicates β₂GPI-dependent antiphospholipid antibody mediation of coagulation.

44. The polypeptide of claim 3, 8, 10, 1, 18, or 31, wherein the polypeptide lacks a T cell epitope, said T cell epitope capable of activating T cells in an individual having β₂GPI dependent antiphospholipid antibodies.

45. A composition comprising an effective amount of the polypeptide of claim 44, wherein an effective amount is an amount sufficient to induce tolerance.

46. The composition of claim 45, further comprising a pharmaceutically acceptable excipient.

47. A polymeric polypeptides comprising a plurality of the polypeptide of claim 3, 8, 10, 1, 18, or 31.

48. The polymeric polypeptide of claim 47, wherein the polypeptide lacks a T cell epitope, said T cell epitope capable of activating T cells in an individual having β₂GPI dependent antiphospholipid antibodies.

49. The polymeric polypeptide of claim 48, wherein the polymeric polypeptide is a linear polymer.

50. The polymeric polypeptide of claim 48, wherein the polymeric polypeptide is a branched polymer.

51. The polymeric polypeptide of claim 48, wherein the polymeric polypeptide comprises at least two different domain 1 β₂GPI polypeptides.

52. The polymeric polypeptide of claim 48 further comprising a polypeptide selected from the group consisting of domain 2 β₂GPI; domain 3 β₂GPI; and domain 5 β₂GPI.

53. A composition comprising the polymeric polypeptide of claim 48 and a pharmaceutically acceptable excipient.

54. A fusion polypeptide comprising the polypeptide of claim 3, 8, 10, 1, 18, or 31.

55. The fusion polypeptide of claim 54, wherein the polypeptide lacks a T cell epitope, said T cell epitope capable of activating T cells in an individual having β₂GPI dependent antiphospholipid antibodies.

56. The fusion polypeptide of claim 55, wherein the fusion polypeptide is a linear polymer.

57. The fusion polypeptide of claim 55, wherein the fusion polypeptide is a branched polymer.

58. A composition comprising the fusion polypeptide of claim 55 and a pharmaceutically acceptable excipient.

59. A composition comprising the polypeptide of claim 3, 8, 10, 1, 18 or 31 and a pharmaceutically acceptable excipient.

60. A conjugate comprising a valency platform molecule, and a polypeptide comprising a domain 1 β₂GPI polypeptide, wherein said polypeptide comprises at least 6 contiguous amino acids of SEQ ID NO:4, and wherein said polypeptide specifically binds to a β₂GPI-dependent antiphospholipid antibody.

61. The conjugate of claim 60, wherein the platform molecule is proteinaceous.

62. The conjugate of claim 60, wherein the polypeptide comprises at least 10 contiguous amino acids of SEQ ID NO:4.

63. The conjugate of claim 60, wherein the polypeptide comprises at least 20 contiguous amino acids of SEQ ID NO:4.

64. The conjugate of claim 60, wherein the polypeptide comprises at least 30 contiguous amino acids of SEQ ID NO:4.

65. The conjugate of claim 60, wherein the polypeptide comprises at least 60 contiguous amino acids of SEQ ID NO:4.

66.

NO:4, and wherein said polypeptide specifically binds to a β₂GPI-dependent antiphospholipid antibody, wherein the conjugate further comprises a label.

75. The conjugate of claim 60, 62, 63, 64, or 65 wherein the polypeptide lacks a T cell epitope, said T cell epitope capable of activating T cells in an individual having β₂GPI dependent antiphospholipid antibodies.

76. The conjugate of claim 75, wherein the polypeptide comprises SEQ ID NOS: 4, 5, 6, 7, 8, 9, 10, 11 or 12.

77. The conjugate of claim 75, wherein the valency platform molecule is non-proteinaceous.

78. The conjugate of claim 75, wherein the molecular weight of a population of valency platform molecules is homogeneous.

79. The conjugate of claim 75, wherein the platform molecule is linked to the polypeptide by a thioether bond.

80. The conjugate of claim 75, wherein the domain 1 β₂GPI polypeptide consists of about amino acid 2 through about amino acid 63 of SEQ ID NO:2.

81. The conjugate of claim 75, wherein the domain 1 β₂GPI polypeptide consists of SEQ ID NO:29.

82. The conjugate of claim 81 wherein the platform molecule comprises polyethylene glycol.

83. A composition comprising the conjugate of claim 75 and a pharmaceutically acceptable excipient.

84. The conjugate of claim 75, wherein the polypeptide further comprises amino acid 40 through amino acid 45 of SEQ ID NO:4, amino acid 38 through amino acid 44 of SEQ ID NO:4, or amino acid 19 of SEQ ID NO:4.

85. The conjugate of claim 75 wherein the valency platform molecule comprises polyethylene glycol.

86. A kit comprising the conjugate of claim 75.

87. A conjugate comprising a polypeptide comprising a domain 1 β₂GPI polypeptide, wherein said domain 1 β₂GPI polypeptide consists of about amino acid 2 through about amino acid 63 of SEQ ID NO:2, wherein said polypeptide specifically binds to a β₂GPI-dependent antiphospholipid antibody, and further wherein the polypeptide lacks a T cell epitope, said T cell epitope capable of activating T cells in an individual having β₂GPI dependent antiphospholipid antibodies.

88. The conjugate of claim 87; wherein the domain 1 β₂GPI polypeptide consists of SEQ ID NO:29.

89. A composition comprising the conjugate of claim 88 a pharmaceutically acceptable excipient.

90. A composition comprising the conjugate of claim 87 and a pharmaceutically acceptable excipient.

91. A kit comprising the conjugate of claim 87.

92. A conjugate comprising a valency platform molecule and a domain 1 β₂GPI polypeptide consisting of about amino acid 2 through about amino acid 63 of SEQ ID NO:2.

93. The conjugate of claim 92, wherein the conjugate comprises four of the domain 1 β₂GPI polypeptides.

94. A composition comprising the conjugate of claim 93 and a pharmaceutically acceptable excipient.

95. A method of inducing tolerance in an individual, comprising administering an effective amount of a composition comprising the conjugate of claim 93 to the individual.

96. The conjugate of claim 92, wherein the domain 1 β₂GPI polypeptide consists of SEQ ID NO:29.

97. The conjugate of claim 96, wherein the conjugate comprises four of the domain 1 β₂GPI polypeptides.

98. A composition comprising the conjugate of claim 97 and a pharmaceutically acceptable excipient.

99. A method of inducing tolerance in an individual, comprising administering an effective amount of a composition comprising the conjugate of claim 97 to the individual.

100. A composition comprising the conjugate of claim 96 and a pharmaceutically acceptable excipient.

101. A method of inducing tolerance in an individual, comprising administering an effective amount of a composition comprising the conjugate of claim 96 to the individual.

102. A composition comprising the conjugate of claim 92 and a pharmaceutically acceptable excipient.

103. A method of inducing tolerance in an individual, comprising administering an effective amount of a composition comprising the conjugate of claim 92 to the individual.

104. The method of claim 103, 95, 101, or 99, wherein the individual is human.

* * * * *

SEQUENCE LISTING

<160> NUMBER OF SEQ ID NOS: 30

<210> SEQ ID NO 1
<211> LENGTH: 978
<212> TYPE: DNA
<213> ORGANISM: Homo sapiens
<220> FEATURE:
<221> NAME/KEY: CDS
<222> LOCATION: (1)...(978)

<400> SEQUENCE: 1

```
gga cgg acc tgt ccc aag cca gat gat tta cca ttt tcc aca gtg gtc      48
Gly Arg Thr Cys Pro Lys Pro Asp Asp Leu Pro Phe Ser Thr Val Val
1               5                   10                  15 ccg tta aaa aca ttc tat gag cca gga gaa gag att acg tat tcc tgc      96
Pro Leu Lys Thr Phe Tyr Glu Pro Gly Glu Glu Ile Thr Tyr Ser Cys
            20                  25                  30 aag ccg ggc tat gtg tcc cga gga ggg atg aga aag ttt atc tgc cct     144
Lys Pro Gly Tyr Val Ser Arg Gly Gly Met Arg Lys Phe Ile Cys Pro
        35                  40                  45 ctc aca gga ctg tgg ccc atc aac act ctg aaa tgt aca ccc aga gta     192
Leu Thr Gly Leu Trp Pro Ile Asn Thr Leu Lys Cys Thr Pro Arg Val
    50                  55                  60 tgt cct ttt gct gga atc tta gaa aat gga gcc gta cgc tat acg act     240
Cys Pro Phe Ala Gly Ile Leu Glu Asn Gly Ala Val Arg Tyr Thr Thr
65                  70                  75                  80 ttt gaa tat ccc aac acg atc agt ttt tct tgt aac act ggg ttt tat     288
Phe Glu Tyr Pro Asn Thr Ile Ser Phe Ser Cys Asn Thr Gly Phe Tyr
                85                  90                  95 ctg aat ggc gct gat tct gcc aag tgc act gag gaa gga aaa tgg agc     336
Leu Asn Gly Ala Asp Ser Ala Lys Cys Thr Glu Glu Gly Lys Trp Ser
            100                 105                 110 ccg gag ctt cct gtc tgt gct ccc atc atc tgc cct cca tcc ata         384
Pro Glu Leu Pro Val Cys Ala Pro Ile Ile Cys Pro Pro Ser Ile
        115                 120                 125 cct acg ttt gca aca ctt cgt gtt tat aag cca tca gct gga aac aat     432
Pro Thr Phe Ala Thr Leu Arg Val Tyr Lys Pro Ser Ala Gly Asn Asn
    130                 135                 140 tcc ctc tat cgg gac aca gca gtt ttt gaa tgt ttg cca caa cat gcg     480
Ser Leu Tyr Arg Asp Thr Ala Val Phe Glu Cys Leu Pro Gln His Ala
145                 150                 155                 160 atg ttt gga aat gat aca att acc tgc acg aca cat gga aat tgg act     528
Met Phe Gly Asn Asp Thr Ile Thr Cys Thr Thr His Gly Asn Trp Thr
                165                 170                 175
```

-continued

```
aaa tta cca gaa tgc agg gaa gta aaa tgc cca ttc cca tca aga cca    576
Lys Leu Pro Glu Cys Arg Glu Val Lys Cys Pro Phe Pro Ser Arg Pro
            180                 185                 190 gac aat gga ttt gtg aac tat cct gca aaa cca aca ctt tat tac aag    624
Asp Asn Gly Phe Val Asn Tyr Pro Ala Lys Pro Thr Leu Tyr Tyr Lys
        195                 200                 205 gat aaa gcc aca ttt ggc tgc cat gat gga tat tct ctg gat ggc ccg    672
Asp Lys Ala Thr Phe Gly Cys His Asp Gly Tyr Ser Leu Asp Gly Pro
    210                 215                 220 gaa gaa ata gaa tgt acc aaa ctg gga aac tgg tct gcc atg cca agt    720
Glu Glu Ile Glu Cys Thr Lys Leu Gly Asn Trp Ser Ala Met Pro Ser
225                 230                 235                 240 tgt aaa gca tct tgt aaa tta cct gtg aaa aaa gcc act gtg gtg tac    768
Cys Lys Ala Ser Cys Lys Leu Pro Val Lys Lys Ala Thr Val Val Tyr
                245                 250                 255 caa gga gag aga gta aag att cag gaa aaa ttt aag aat gga atg cta    816
Gln Gly Glu Arg Val Lys Ile Gln Glu Lys Phe Lys Asn Gly Met Leu
            260                 265                 270 cat ggt gat aaa gtt tct ttc ttc tgc aaa aat aag gaa aag aag tgt    864
His Gly Asp Lys Val Ser Phe Phe Cys Lys Asn Lys Glu Lys Lys Cys
        275                 280                 285 agc tat aca gag gat gct cag tgt ata gat ggc act atc gaa gtc ccc    912
Ser Tyr Thr Glu Asp Ala Gln Cys Ile Asp Gly Thr Ile Glu Val Pro
    290                 295                 300 aaa tgc ttc aag gaa cac agt tct ctg gct ttt tgg aaa act gat gca    960
Lys Cys Phe Lys Glu His Ser Ser Leu Ala Phe Trp Lys Thr Asp Ala
305                 310                 315                 320 tcc gat gta aag cca tgc                                            978
Ser Asp Val Lys Pro Cys
                325
```

<210> SEQ ID NO 2
<211> LENGTH: 326
<212> TYPE: PRT
<213> ORGANISM: Homo sapiens

<400> SEQUENCE: 2

```
Gly Arg Thr Cys Pro Lys Pro Asp Asp Leu Pro Phe Ser Thr Val Val
1               5                   10                  15

Pro Leu Lys Thr Phe Tyr Glu Pro Gly Glu Glu Ile Thr Tyr Ser Cys
            20                  25                  30

Lys Pro Gly Tyr Val Ser Arg Gly Gly Met Arg Lys Phe Ile Cys Pro
        35                  40                  45

Leu Thr Gly Leu Trp Pro Ile Asn Thr Leu Lys Cys Thr Pro Arg Val
    50                  55                  60

Cys Pro Phe Ala Gly Ile Leu Glu Asn Gly Ala Val Arg Tyr Thr Thr
65                  70                  75                  80

Phe Glu Tyr Pro Asn Thr Ile Ser Phe Ser Cys Asn Thr Gly Phe Tyr
                85                  90                  95

Leu Asn Gly Ala Asp Ser Ala Lys Cys Thr Glu Glu Gly Lys Trp Ser
            100                 105                 110

Pro Glu Leu Pro Val Cys Ala Pro Ile Ile Cys Pro Pro Pro Ser Ile
        115                 120                 125

Pro Thr Phe Ala Thr Leu Arg Val Tyr Lys Pro Ser Ala Gly Asn Asn
    130                 135                 140

Ser Leu Tyr Arg Asp Thr Ala Val Phe Glu Cys Leu Pro Gln His Ala
145                 150                 155                 160

Met Phe Gly Asn Asp Thr Ile Thr Cys Thr Thr His Gly Asn Trp Thr
```

-continued

```
                  165                 170                 175
Lys Leu Pro Glu Cys Arg Glu Val Lys Cys Pro Phe Pro Ser Arg Pro
            180                 185                 190
Asp Asn Gly Phe Val Asn Tyr Pro Ala Lys Pro Thr Leu Tyr Tyr Lys
            195                 200                 205
Asp Lys Ala Thr Phe Gly Cys His Asp Gly Tyr Ser Leu Asp Gly Pro
            210                 215                 220
Glu Glu Ile Glu Cys Thr Lys Leu Gly Asn Trp Ser Ala Met Pro Ser
225                 230                 235                 240
Cys Lys Ala Ser Cys Lys Leu Pro Val Lys Ala Thr Val Val Tyr
            245                 250                 255
Gln Gly Glu Arg Val Lys Ile Gln Glu Lys Phe Lys Asn Gly Met Leu
            260                 265                 270
His Gly Asp Lys Val Ser Phe Phe Cys Lys Asn Lys Glu Lys Lys Cys
            275                 280                 285
Ser Tyr Thr Glu Asp Ala Gln Cys Ile Asp Gly Thr Ile Glu Val Pro
            290                 295                 300
Lys Cys Phe Lys Glu His Ser Ser Leu Ala Phe Trp Lys Thr Asp Ala
305                 310                 315                 320
Ser Asp Val Lys Pro Cys
                325

<210> SEQ ID NO 3
<211> LENGTH: 192
<212> TYPE: DNA
<213> ORGANISM: Homo sapiens
<220> FEATURE:
<221> NAME/KEY: CDS
<222> LOCATION: (1)...(192)

<400> SEQUENCE: 3 gga cgg acc tgt ccc aag cca gat gat tta cca ttt tcc aca gtg gtc      48
Gly Arg Thr Cys Pro Lys Pro Asp Asp Leu Pro Phe Ser Thr Val Val
 1               5                  10                  15 ccg tta aaa aca ttc tat gag cca gga gaa gag att acg tat tcc tgc      96
Pro Leu Lys Thr Phe Tyr Glu Pro Gly Glu Glu Ile Thr Tyr Ser Cys
                20                  25                  30 aag ccg ggc tat gtg tcc cga gga ggg atg aga aag ttt atc tgc cct     144
Lys Pro Gly Tyr Val Ser Arg Gly Gly Met Arg Lys Phe Ile Cys Pro
            35                  40                  45 ctc aca gga ctg tgg ccc atc aac act ctg aaa tgt aca ccc aga gta     192
Leu Thr Gly Leu Trp Pro Ile Asn Thr Leu Lys Cys Thr Pro Arg Val
        50                  55                  60

<210> SEQ ID NO 4
<211> LENGTH: 64
<212> TYPE: PRT
<213> ORGANISM: Homo sapiens

<400> SEQUENCE: 4

Gly Arg Thr Cys Pro Lys Pro Asp Asp Leu Pro Phe Ser Thr Val Val
 1               5                  10                  15

Pro Leu Lys Thr Phe Tyr Glu Pro Gly Glu Glu Ile Thr Tyr Ser Cys
                20                  25                  30

Lys Pro Gly Tyr Val Ser Arg Gly Gly Met Arg Lys Phe Ile Cys Pro
            35                  40                  45

Leu Thr Gly Leu Trp Pro Ile Asn Thr Leu Lys Cys Thr Pro Arg Val
        50                  55                  60
```

```
<210> SEQ ID NO 5
<211> LENGTH: 6
<212> TYPE: PRT
<213> ORGANISM: Homo sapiens

<400> SEQUENCE: 5

Cys Thr Pro Arg Val Cys
1               5

<210> SEQ ID NO 6
<211> LENGTH: 6
<212> TYPE: PRT
<213> ORGANISM: Homo sapiens

<400> SEQUENCE: 6

Phe Ser Thr Val Val Pro
1               5

<210> SEQ ID NO 7
<211> LENGTH: 6
<212> TYPE: PRT
<213> ORGANISM: Homo sapiens

<400> SEQUENCE: 7

Lys Pro Asp Asp Leu Pro
1               5

<210> SEQ ID NO 8
<211> LENGTH: 6
<212> TYPE: PRT
<213> ORGANISM: Homo sapiens

<400> SEQUENCE: 8

Gly Arg Thr Cys Pro Lys
1               5

<210> SEQ ID NO 9
<211> LENGTH: 6
<212> TYPE: PRT
<213> ORGANISM: Homo sapiens

<400> SEQUENCE: 9

Thr Leu Lys Cys Thr Pro
1               5

<210> SEQ ID NO 10
<211> LENGTH: 6
<212> TYPE: PRT
<213> ORGANISM: Homo sapiens

<400> SEQUENCE: 10

Ile Cys Pro Leu Thr Gly
1               5

<210> SEQ ID NO 11
<211> LENGTH: 6
<212> TYPE: PRT
<213> ORGANISM: Homo sapiens

<400> SEQUENCE: 11

Phe Ile Cys Pro Leu Thr
1               5

<210> SEQ ID NO 12
```

```
<211> LENGTH: 6
<212> TYPE: PRT
<213> ORGANISM: Homo sapiens

<400> SEQUENCE: 12

Ile Thr Tyr Ser Cys Lys
 1               5

<210> SEQ ID NO 13
<211> LENGTH: 45
<212> TYPE: DNA
<213> ORGANISM: Artificial Sequence
<220> FEATURE:
<223> OTHER INFORMATION: synthetic construct

<400> SEQUENCE: 13
aaaccacctt aatggtgatg gtgatggtgg ccacatggct ttaca                    45

<210> SEQ ID NO 14
<211> LENGTH: 31
<212> TYPE: DNA
<213> ORGANISM: Artificial Sequence
<220> FEATURE:
<223> OTHER INFORMATION: synthetic construct

<400> SEQUENCE: 14
gacatactct gggtgtccgt cctgcaatag c                                   31

<210> SEQ ID NO 15
<211> LENGTH: 30
<212> TYPE: DNA
<213> ORGANISM: Artificial Sequence
<220> FEATURE:
<223> OTHER INFORMATION: synthetic construct

<400> SEQUENCE: 15
tggagggcag atgatccgtc ctgcaatagc                                     30

<210> SEQ ID NO 16
<211> LENGTH: 33
<212> TYPE: DNA
<213> ORGANISM: Artificial Sequence
<220> FEATURE:
<223> OTHER INFORMATION: synthetic construct

<400> SEQUENCE: 16
gaatgggcat tttacttccc gtcctgcaat agc                                 33

<210> SEQ ID NO 17
<211> LENGTH: 33
<212> TYPE: DNA
<213> ORGANISM: Artificial Sequence
<220> FEATURE:
<223> OTHER INFORMATION: synthetic construct

<400> SEQUENCE: 17
aggtaattta caagatgccc gtcctgcaat agc                                 33

<210> SEQ ID NO 18
<211> LENGTH: 30
<212> TYPE: DNA
<213> ORGANISM: Artificial Sequence
<220> FEATURE:
<223> OTHER INFORMATION: synthetic construct

<400> SEQUENCE: 18
```
atggtgatgg tggccacaac ttggcatggc          30

<210> SEQ ID NO 19
<211> LENGTH: 32
<212> TYPE: DNA
<213> ORGANISM: Artificial Sequence
<220> FEATURE:
<223> OTHER INFORMATION: synthetic construct

<400> SEQUENCE: 19
atggtgatgg tggccgcatt ctggtaattt ag          32

<210> SEQ ID NO 20
<211> LENGTH: 5
<212> TYPE: PRT
<213> ORGANISM: Artificial Sequence
<220> FEATURE:
<223> OTHER INFORMATION: Amino acids 3-60 were deleted from 2GPI (SEQ ID
      NO:2)

<400> SEQUENCE: 20

Gly Arg Thr Pro Arg
1               5

<210> SEQ ID NO 21
<211> LENGTH: 5
<212> TYPE: PRT
<213> ORGANISM: Artificial Sequence
<220> FEATURE:
<223> OTHER INFORMATION: Amino acids 3-120 were deleted from  2GPI
      (SEQ ID NO:2)

<400> SEQUENCE: 21

Gly Arg Ile Ile Cys
1               5

<210> SEQ ID NO 22
<211> LENGTH: 5
<212> TYPE: PRT
<213> ORGANISM: Artificial Sequence
<220> FEATURE:
<223> OTHER INFORMATION: Amino acids 3-182 were deleted from  2GPI
      (SEQ ID NO:2)

<400> SEQUENCE: 22

Gly Arg Glu Val Lys
1               5

<210> SEQ ID NO 23
<211> LENGTH: 5
<212> TYPE: PRT
<213> ORGANISM: Artificial Sequence
<220> FEATURE:
<223> OTHER INFORMATION: Amino acids 3-242 were deleted from  2GPI
      (SEQ ID NO:2)

<400> SEQUENCE: 23

Gly Arg Ala Ser Cys
1               5

<210> SEQ ID NO 24
<211> LENGTH: 5
<212> TYPE: PRT
<213> ORGANISM: Artificial Sequence
<220> FEATURE:

```
<223> OTHER INFORMATION: Amino acids 242-326 were deleted or
      amino acids 182-326 were deleted or
      amino acids 165-326 were deleted or
      amino acids 123-326 were deleted from  2GPI (SEQ ID NO:2)

<400> SEQUENCE: 24

Gly Arg Thr Cys Pro
 1               5

<210> SEQ ID NO 25
<211> LENGTH: 26
<212> TYPE: DNA
<213> ORGANISM: Artificial Sequence
<220> FEATURE:
<223> OTHER INFORMATION: synthetic construct

<400> SEQUENCE: 25
ctataaatac ggatcccggg aattcg                                          26

<210> SEQ ID NO 26
<211> LENGTH: 35
<212> TYPE: DNA
<213> ORGANISM: Artificial Sequence
<220> FEATURE:
<223> OTHER INFORMATION: synthetic construct

<400> SEQUENCE: 26
gcagctggcc aactctgggt gtacatttca gagtg                                35

<210> SEQ ID NO 27
<211> LENGTH: 34
<212> TYPE: DNA
<213> ORGANISM: Artificial Sequence
<220> FEATURE:
<223> OTHER INFORMATION: synthetic construct

<400> SEQUENCE: 27
gcagctggcc aatgatggga gcacagagag gaag                                 34

<210> SEQ ID NO 28
<211> LENGTH: 63
<212> TYPE: PRT
<213> ORGANISM: Homo sapiens

<400> SEQUENCE: 28

Gly Arg Thr Cys Pro Lys Pro Asp Asp Leu Pro Phe Ser Thr Val Val
 1               5                  10                  15

Pro Leu Lys Thr Phe Tyr Glu Pro Gly Glu Glu Ile Thr Tyr Ser Cys
                20                  25                  30

Lys Pro Gly Tyr Val Ser Arg Gly Gly Met Arg Lys Phe Ile Cys Pro
            35                  40                  45

Leu Thr Gly Leu Trp Pro Ile Asn Thr Leu Lys Cys Thr Pro Arg
    50                  55                  60

<210> SEQ ID NO 29
<211> LENGTH: 62
<212> TYPE: PRT
<213> ORGANISM: Homo sapiens

<400> SEQUENCE: 29

Arg Thr Cys Pro Lys Pro Asp Asp Leu Pro Phe Ser Thr Val Val Pro
 1               5                  10                  15

Leu Lys Thr Phe Tyr Glu Pro Gly Glu Glu Ile Thr Tyr Ser Cys Lys
                20                  25                  30
```

```
Pro Gly Tyr Val Ser Arg Gly Gly Met Arg Lys Phe Ile Cys Pro Leu
        35                  40                  45

Thr Gly Leu Trp Pro Ile Asn Thr Leu Lys Cys Thr Pro Arg
        50                  55                  60

<210> SEQ ID NO 30
<211> LENGTH: 65
<212> TYPE: PRT
<213> ORGANISM: Artificial Sequence
<220> FEATURE:
<223> OTHER INFORMATION: synthetic construct

<400> SEQUENCE: 30

Gly Arg Thr Cys Pro Lys Pro Asp Asp Leu Pro Phe Ser Thr Val Val
1               5                   10                  15

Pro Leu Lys Thr Phe Tyr Glu Pro Gly Glu Glu Ile Thr Tyr Ser Cys
                20                  25                  30

Lys Pro Gly Tyr Val Ser Arg Gly Gly Met Arg Lys Phe Ile Cys Pro
                35                  40                  45

Leu Thr Gly Leu Trp Pro Ile Asn Thr Leu Lys Cys Thr Pro Arg Val
        50                  55                  60

Cys
65
```